US012581854B2

(12) United States Patent
Cha et al.

(10) Patent No.: US 12,581,854 B2
(45) Date of Patent: Mar. 17, 2026

(54) ORGANIC LIGHT EMITTING DIODE FOR HIGH EFFICIENCY

(71) Applicant: SFC CO., LTD., Cheongju-si (KR)

(72) Inventors: Soon-Wook Cha, Goyang (KR); Young-Hwan Park, Cheongju (KR); Seo-Yeon Yoon, Seongnam (KR); So Young Shim, Daejeon (KR)

(73) Assignee: SFC CO., LTD., Cheongju-si (KR)

( * ) Notice: Subject to any disclaimer, the term of this patent is extended or adjusted under 35 U.S.C. 154(b) by 236 days.

(21) Appl. No.: 17/185,778

(22) Filed: Feb. 25, 2021

(65) Prior Publication Data

US 2021/0184136 A1 Jun. 17, 2021

Related U.S. Application Data

(62) Division of application No. 15/202,007, filed on Jul. 5, 2016.

(30) Foreign Application Priority Data

Jul. 14, 2015 (KR) ........................ 10-2015-0099655

(51) Int. Cl.
*H01L 51/00* (2006.01)
*C07D 307/91* (2006.01)
(Continued)

(52) U.S. Cl.
CPC ....... *H10K 85/6574* (2023.02); *C07D 307/91* (2013.01); *C07D 307/93* (2013.01);
(Continued)

(58) Field of Classification Search
None
See application file for complete search history.

(56) References Cited

U.S. PATENT DOCUMENTS

2003/0165715 A1* 9/2003 Yoon .................... C07D 235/18 313/506
2004/0161633 A1* 8/2004 Seo ........................... C09B 1/00 313/506
(Continued)

FOREIGN PATENT DOCUMENTS

JP 2005-314239 A * 11/2005
JP 2010034548 A * 2/2010
(Continued)

OTHER PUBLICATIONS

Machine English Translation of Jang et al. (WO 2016/027938 A1). Jan. 31, 2023.*
Machine English Translation of Inoue et al. (JP 2005-314239 A). Jan. 31, 2023.*
Machine English translation of JP-2010034548-A. Jun. 22, 2023.*
(Continued)

*Primary Examiner* — Jay Yang
(74) *Attorney, Agent, or Firm* — STIP Law Group, LLC

(57) ABSTRACT

Disclosed herein is an organic light-emitting diode, comprising: a first electrode, a second electrode opposite the first electrode, and a light-emitting layer and an electron-density-controlling layer in that order between the first electrode and the second electrode, wherein the electron-density-controlling layer includes at least one selected from among compounds represented by Chemical Formulas A to D, and the light-emitting layer includes at least one anthracene compound represented by Chemical Formula H. The electron-density-controlling layer may be disposed between the light-emitting layer and an electron transport layer.

9 Claims, 7 Drawing Sheets

(51) Int. Cl.

| | |
|---|---|
| ***C07D 307/93*** | (2006.01) |
| ***C07D 307/94*** | (2006.01) |
| ***C09K 11/02*** | (2006.01) |
| ***C09K 11/06*** | (2006.01) |
| ***H10K 50/11*** | (2023.01) |
| ***H10K 85/60*** | (2023.01) |

(52) U.S. Cl.

CPC .......... *C07D 307/94* (2013.01); *C09K 11/025* (2013.01); *C09K 11/06* (2013.01); *H10K 50/11* (2023.02); *H10K 85/615* (2023.02); *H10K 85/622* (2023.02); *H10K 85/626* (2023.02); *H10K 85/633* (2023.02); *H10K 85/636* (2023.02); *C09K 2211/1033* (2013.01); *C09K 2211/1088* (2013.01)

(56) References Cited

U.S. PATENT DOCUMENTS

2006/0286403 A1* 12/2006 Lee .................... H01L 51/5048
313/506
2016/0351816 A1* 12/2016 Kim ...................... C09K 11/02

FOREIGN PATENT DOCUMENTS

JP 2014224047 A * 12/2014
WO WO-2015/194839 A1 * 12/2015
WO WO-2016/027938 A1 * 2/2016

OTHER PUBLICATIONS

Machine English translation of Ito et al. (JP-2014224047-A). Jul. 3, 2024.*

* cited by examiner

ORGANIC LIGHT EMITTING DIODE FOR HIGH EFFICIENCY

CROSS-REFERENCE TO RELATED APPLICATIONS

This application is a Division of application Ser. No. 15/202,007 filed on Jul. 5, 2016 which in turn claims the benefit of Korean Patent Application No. 10-2015-0099655 filed on Jul. 14, 2015, the disclosures of which are incorporated by reference into the present application.

BACKGROUND OF THE INVENTION

1. Field of the Invention

The present disclosure relates to an organic light-emitting diode. More particularly, the present disclosure relates to an organic light-emitting diode that is of high luminance efficiency and that can effectively operate at a low voltage, wherein a compound of a specific structure is used in a light-emitting layer and a compound of a specific structure is introduced into an electron-density-controlling layer.

2. Description of the Related Art

Organic light-emitting diodes, based on self-luminescence, exhibit the advantages of having a wide viewing angle, excellent contrast, fast response time, high brightness, and excellent driving voltage and response rate characteristics, and of realizing a polychromic display.

A typical organic light-emitting diode includes an anode and a cathode, with an organic emissive layer disposed therebetween.

As to the general structure of the organic light-emitting diode, a hole transport layer, a light-emitting layer, an electron transport layer, and a cathode are formed in that order on an anode. Here, all of the hole transport layer, the light-emitting layer, and the electron transport layer are organic films comprising organic compounds.

An organic light-emitting diode having such a structure operates as follows: when a voltage is applied between the anode and the cathode, the anode injects holes, which are then transferred to the light-emitting layer via the hole transport layer while electrons injected from the cathode move to the light-emitting layer via the electron transport layer. In the luminescent zone, the carriers, that is, holes and electrons, recombine to produce an exciton. When the exciton returns to the ground state from the excited state, the molecule of the light-emitting layer emits light.

The materials used as the organic layers in organic light-emitting diodes may be divided into luminescent materials and charge carrier materials, for example, a hole injection material, a hole transport material, an electron injection material, and an electron transport material. The light-emitting mechanisms allow the luminescent materials to be classified as fluorescent and phosphorescent materials, which use excitons in singlet and triplet states, respectively.

Meanwhile, when a single material is employed as the luminescent material, intermolecular actions cause the maximum luminescence wavelength to shift toward a longer wavelength, resulting in a reduction in color purity and light emission efficiency. In this regard, a host-dopant system may be used as a luminescent material so as to increase the color purity and the light emission efficiency through energy transfer. This is based on the principle whereby, when a dopant has a smaller energy band gap than a host, which constitutes the light-emitting layer, the addition of a small amount of the dopant to the host generates excitons from the light-emitting layer so that the excitons are transported to the dopant, emitting light at high efficiency. Here, light of desired wavelengths can be obtained depending on the kind of the dopant because the wavelength of the host moves into the wavelength range of the dopant.

With regard to the efficiency of organic light-emitting diodes, statistically, there is a 25% probability of forming a singlet state and a 75% probability of forming a triplet state. It would thus be expected that in fluorescent OLEDs only the formation of singlet excitons results in the emission of useful radiation, placing a theoretical limit of 25% on the internal quantum efficiency.

To avoid this disadvantage, Korean Patent Unexamined Application Publication No. 10-2012-0092555 (Aug. 21, 2012) proposes the effective occurrence of a TTF phenomenon, in which singlet excitons are generated through the collision and fusion of two triplet excitons. For this, this reference discloses an electroluminescence device in which a blocking layer is interposed between a light-emitting layer and an electron injection layer, with an affinity difference between the electron injection layer and the blocking layer. In this regard, the blocking layer is set to have a triplet energy larger than that of the host of the light-emitting layer so as to confine triplet excitons within the light-emitting layer, whereby the effective occurrence of the TTF phenomenon is induced. In addition, the electroluminescence device employs a material in which the respective affinities of both the electron injection layer and the blocking layer satisfy a specific condition.

As described above, the invention of the reference document is designed to cause the effective occurrence of a TTF phenomenon in order to provide high emission efficiency for an organic electroluminescence device. To this end, the blocking layer should include a material that is higher in triplet energy than the host, and an aromatic heterocyclic compound of a specific fused ring should be employed in the blocking layer.

Another technique for improving luminance efficiency can be found in Korean Patent Unexamined Application Publication No. 10-2006-0022676 (Mar. 10, 2006), which describes an organic electroluminescence device having an electron-density-controlling layer disposed between a light-emitting layer and an electron transport layer.

In spite of various efforts made to fabricate organic light-emitting diodes having effective luminescence characteristics, however, there is still a continued need to develop organic light-emitting diodes having a higher effective luminance efficiency.

RELATED ART DOCUMENT

Korean Patent Unexamined Application Publication No. 10-2012-0092555 (Aug. 21, 2012)

Korean Patent Unexamined Application Publication No. 10-2006-0022676 (Mar. 10, 2006)

SUMMARY OF THE INVENTION

Accordingly, the present invention has been made keeping in mind the above problems occurring in the related art, and an object of the present invention is to provide an organic light-emitting diode that has high luminance efficiency, wherein a compound of a specific structure is used as a host in the light-emitting layer and a compound of a specific structure is introduced into the electron-density-controlling layer.

The present disclosure provides an organic light-emitting diode, comprising: a first electrode; a second electrode opposite to the first electrode; and a light-emitting layer and an electron-density-controlling layer in that order between the first electrode and the second electrode, wherein the electron-density-controlling layer includes at least one selected from among compounds represented by the following Chemical Formulas A to D, and the light-emitting layer includes at least one anthracene compound represented by the following Chemical Formula H:

[Chemical Formula A]

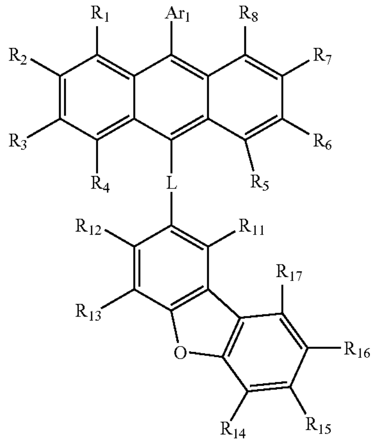

[Chemical Formula B]

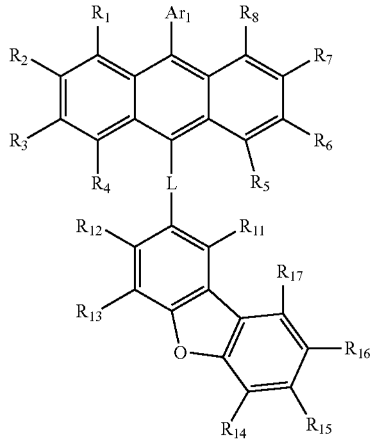

Q1:

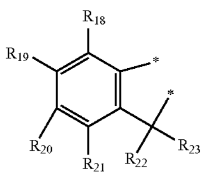

-continued

[Chemical Formula C]

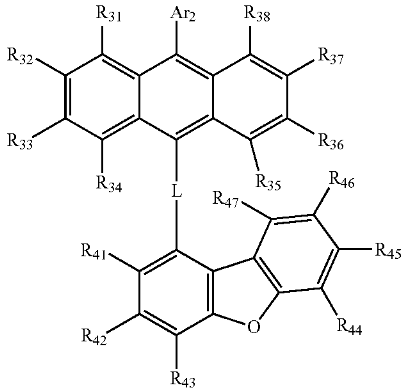

[Chemical Formula D]

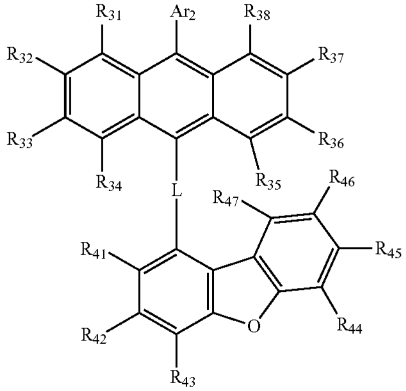

Q2:

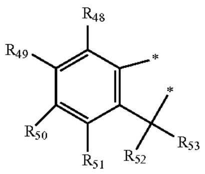

wherein,

R1 to R8, R11 to R23, R31 to R38, and R41 to R53 may be the same or different, and are each independently any one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, a substituted or unsubstituted heteroaryl of 2 to 50 carbon atoms containing 0, N or S as a hetero atom, a cyano, a nitro, and a halogen, a substituted or unsubstituted alkylsilyl of 1 to 30 carbon atoms, a substituted or unsubstituted alkyl germanium of 1 to 30 carbon atoms, a substituted or unsubstituted alkyl boron of 1 to 30 carbon atoms, a substituted or unsubstituted alkyl aluminum of 1 to 30 carbon atoms, a carbonyl, a phosphoryl, an amino, a thiol, a hydroxy, a selenium atom, a tellurium atom, an amide, an ether, and an ester, Ar1 and Ar2 may be the same or different, and are each independently a substituted or unsubstituted aryl of 6 to 50 carbon atoms or a substituted or unsubstituted heteroaryl of 2 to 50 carbon atoms, and a linker L is selected from among a single bond, a substituted or unsubstituted arylene of 6 to 60 carbon atoms, and a substituted or unsubstituted heteroarylene of 2 to 60 carbon atoms, wherein the substituents R12 and R13, or two adjacent ones among the substituents R14 to R17, in Chemical Formula B are respective single bonds for forming a 5-membered ring as a fused ring together with a carbon atom to which substituents R22 and R23 of Structural Formula Q1 are bonded, and two adjacent ones among the substituents R41 to R43 or two adjacent ones among the substituents R44 to R47 in Chemical Formula D are respective single bonds for forming a 5-membered ring as a fused ring together with a carbon to which substituents R52 and R53 of Structural Formula Q2 are bonded, wherein a bond may be formed between substituents R22 and R23, and between the substituents R52 and R53 to form respective rings,

[Chemical Formula H]

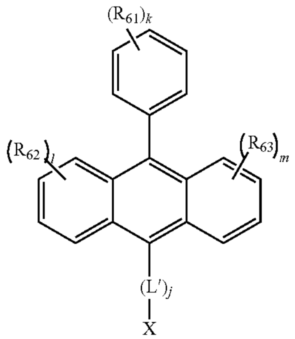

X =

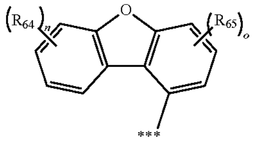

or

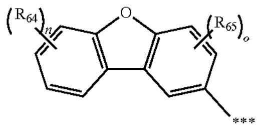

wherein, the substituents R61 to R65 may be the same or different, and are each independently any one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, a substituted or unsubstituted heteroaryl of 2 to 50 carbon atoms containing O, N or S as a hetero atom, a cyano, a nitro, and a halogen, a substituted or unsubstituted alkylsilyl of 1 to 30 carbon atoms, a substituted or unsubstituted alkyl germanium of 1 to 30 carbon atoms, a substituted or unsubstituted alkyl boron of 1 to 30 carbon atoms, a substituted or unsubstituted alkyl aluminum of 1 to 30 carbon atoms, a carbonyl, a phosphoryl, an amino, a thiol, a hydroxy, a selenium atom, a tellurium atom, an amide, an ether, and an ester, with the proviso that a hydrogen atom is positioned on each of the aromatic ring carbon atoms to which none of the substituents R61 to R65 are bonded, the linker L' is a single bond or a substituted or unsubstituted arylene of 6 to 60 carbon atoms;

j is an integer of 0 to 2, with the proviso that when j is 2, corresponding L's are the same or different, k is an integer of 1 to 5, l to n may be the same or different, and are each independently an integer of 1 to 4, is an integer of 1 to 3, with the proviso that when each of k to o is 2 or greater, corresponding R61's to R65's may be the same or different, and '***' for moiety X denotes a bonding site for bonding L', with the proviso that the anthracene compound of Chemical Formula H used in the light-emitting layer is different from the compounds of [Chemical Formula A] to [Chemical Formula D] used in the electron-density-controlling layer.

In some embodiments of the organic light-emitting diode, the first electrode is an anode and the second electrode is a cathode, with the interposition of a hole transport layer between the cathode and the light-emitting layer and an electron transport layer between the electron-density-controlling layer and the anode.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
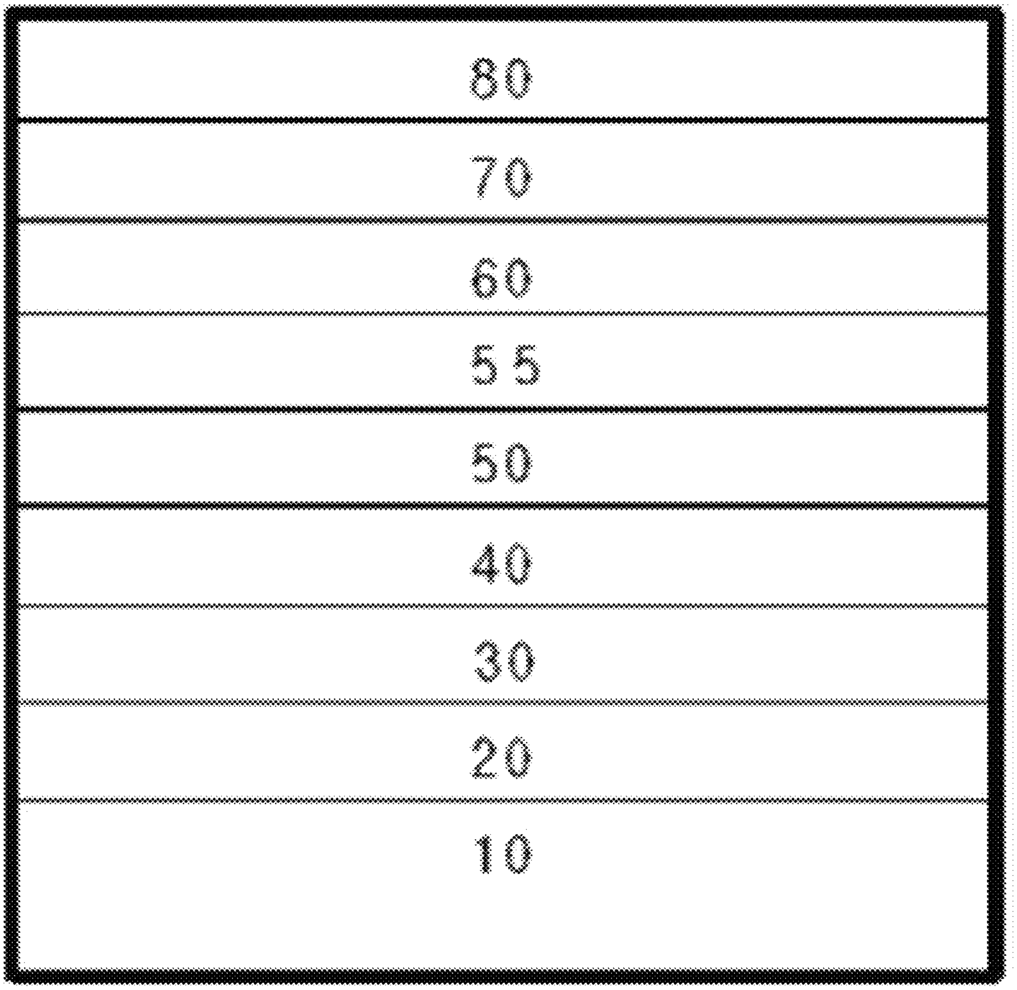
FIG. 1 is a diagram of the structure of an organic light-emitting diode according to some embodiments of the present disclosure.

Hereinafter, some embodiments which can be easily embodied by those skilled in the art will be described with reference to the accompanying drawings. In the drawings of the invention, sizes and dimensions of structures are illustrated by enlarging or reducing as compared with the actual sizes and dimensions to clarify the invention, the known configurations are not illustrated to exhibit characteristic configurations, and the invention is not limited to the drawings. In describing the phenomena of the preferred embodiments of the invention in detail, when it is determined that detailed description of the related known functions or configurations may unnecessarily obscure the gist of the invention, the detailed description is omitted.

In addition, the size and thickness of each configuration illustrated in the drawings are arbitrarily illustrated for the sake of convenience of explanation, and thus the present disclosure may not necessarily be limited to the illustration. Further, in the drawings, the thicknesses of layers and regions are exaggerated for clarity. It will be understood that when an element such as a layer, film, region or substrate is referred to as being "on" another element, it can be directly on the other element or intervening elements may also be present.

Throughout the specification, when a portion may "include" a certain constituent element, unless specified otherwise, it may not be construed to exclude another constituent element but may be construed to further include other constituent elements.

In addition, unless explicitly described to the contrary, the word "comprise" and variations such as "comprises" or "comprising" will be understood to imply the inclusion of stated elements but not the exclusion of any other elements. Further, throughout the specification, the word "on" means positioning on or below the object portion, but does not essentially mean positioning on the lower side of the object portion based on the direction of gravity.

The present disclosure provides an organic light-emitting diode comprising a first electrode; a second electrode opposite the first electrode; and a light-emitting layer and an electron-density-controlling layer in that order between the first electrode and the second electrode, wherein the electron-density-controlling layer includes at least one selected from among compounds represented by the following Chemical Formulas A to D, and the light-emitting layer includes at least one anthracene compound represented by the following Chemical Formula H.

[Chemical Formula A]

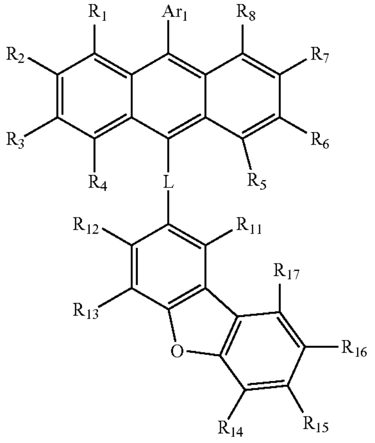

[Chemical Formula B]

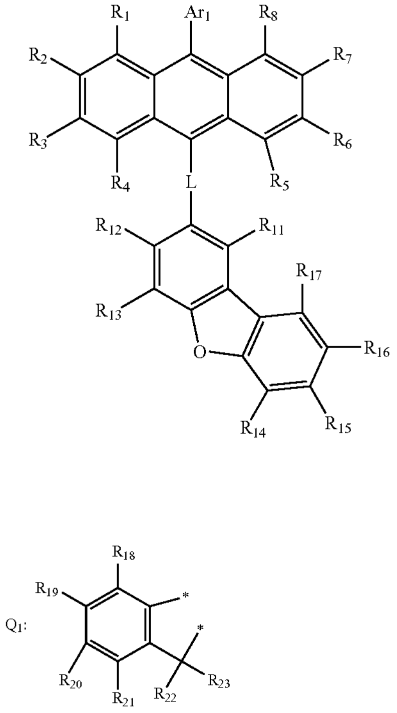

[Chemical Formula C]

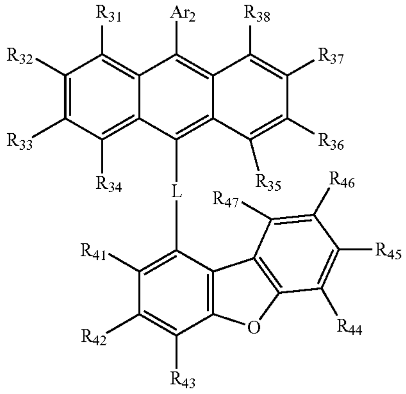

-continued

[Chemical Formula D]

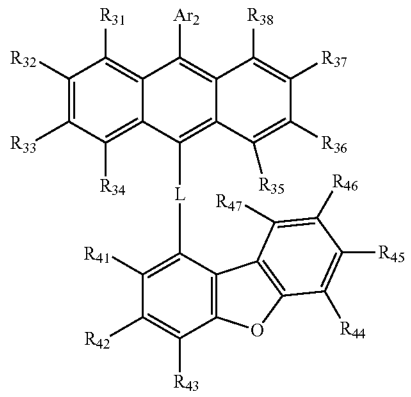

Q2:

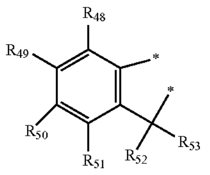

wherein,

R1 to R8, R11 to R23, R31 to R38, and R41 to R53 may be the same or different, and are each independently any one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, a substituted or unsubstituted heteroaryl of 2 to 50 carbon atoms containing 0, N or S as a hetero atom, a cyano, a nitro, and a halogen, a substituted or unsubstituted alkylsilyl of 1 to 30 carbon atoms, a substituted or unsubstituted alkyl germanium of 1 to 30 carbon atoms, a substituted or unsubstituted alkyl boron of 1 to 30 carbon atoms, a substituted or unsubstituted alkyl aluminum of 1 to 30 carbon atoms, a carbonyl, a phosphoryl, an amino, a thiol, a hydroxy, a selenium atom, a tellurium atom, an amide, an ether, and an ester, Ar1 and Ar2 may be the same or different, and are each independently a substituted or unsubstituted aryl of 6 to 50 carbon atoms or a substituted or unsubstituted heteroaryl of 2 to 50 carbon atoms, and a linker L is selected from among a single bond, a substituted or unsubstituted arylene of 6 to 60 carbon atoms, and a substituted or unsubstituted heteroarylene of 2 to 60 carbon atoms, wherein the substituents R12 and R13, or two adjacent ones among the substituents R14 to R17, in Chemical Formula B are respective single bonds for forming a 5-membered ring as a fused ring together with a carbon atom to which substituents R22 and R23 of Structural Formula Q1 are bonded, and two adjacent ones among the substituents R41 to R43 or two adjacent ones among the substituents R44 to R47 in Chemical Formula D are respective single bonds for forming a 5-membered ring as a fused ring together with a carbon to which substituents R52 and R53 of Structural Formula Q2 are bonded, wherein bonds may be formed between the substituents R22 and R23 and between the substituents R52 and R53 to form respective rings,

[Chemical Formula H]

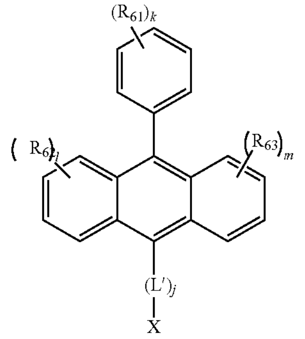

X =

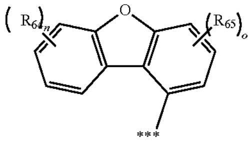

or

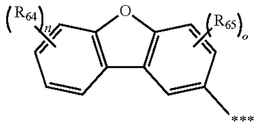

wherein, the substituents R61 to R65 may be the same or different, and are each independently any one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 6 to 30 carbon atoms, a substituted or unsubstituted alkyl amine of 1 to 30 carbon atoms, a substituted or unsubstituted aryl amine of 6 to 30 carbon atoms, a substituted or unsubstituted aryl of 6 to 50 carbon atoms, a substituted or unsubstituted heteroaryl of 2 to 50 carbon atoms containing 0, N or S as a hetero atom, a cyano, a nitro, and a halogen, a substituted or unsubstituted alkylsilyl of 1 to 30 carbon atoms, a substituted or unsubstituted alkyl germanium of 1 to 30 carbon atoms, a substituted or unsubstituted alkyl boron of 1 to 30 carbon atoms, a substituted or unsubstituted alkyl aluminum of 1 to 30 carbon atoms, a carbonyl, a phosphoryl, an amino, a thiol, a hydroxy, a selenium atom, a tellurium atom, an amide, an ether, and an ester, with the proviso that a hydrogen atom is positioned on each of the aromatic ring carbon atoms to which none of the substituents R61 to R65 are bonded, the linker L' is a single bond or a substituted or unsubstituted arylene of 6 to 60 carbon atoms;

j is an integer of 0 to 2, with the proviso that when j is 2, corresponding L's are the same or different, k is an integer of 1 to 5, l to n may be the same or different, and are each independently an integer of 1 to 4, is an integer of 1 to 3, with the proviso that when each of k to o is 2 or greater, corresponding R61's to R65's may be the same or different, '***' for moiety X denotes a bonding site for bonding L', with the proviso that the anthracene compound of Chemical Formula H used in the light-emitting layer is different from the compounds of [Chemical Formula A] to [Chemical Formula D] used in the electron-density-controlling layer, wherein the term 'substituted' in the expression 'substituted or unsubstituted' means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 2 to 24 carbon atoms, an alkylsilyl of 1 to 24 carbon atoms, an arylsilyl of 6 to 24 carbon atoms, and an aryloxy of 6 to 24 carbon atoms.

The term 'substituted' in the expression 'substituted or unsubstituted' means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 2 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. It may be a single or fused aromatic system including a 5- to 7-membered ring, and preferably a 5- to 6-membered ring. Further, the aromatic system may include a fused ring that is formed by adjacent substituents on the aryl radical.

Examples of the aryl include phenyl, naphthyl, anthryl, indenyl, fluorenyl, phenanthryl, triphenylenyl, pyrenyl, perylenyl, chrysenyl, naphthacenyl, and fluoranthenyl, but are not limited thereto.

At least one hydrogen atom of the aryl may be substituted by a deuterium atom, a halogen atom, hydroxy, nitro, cyano, silyl, amino (—NH2, —NH(R), —N(R')(R") wherein R' and R" are each independently an alkyl of 1 to 10 carbon atoms, in this case, called "alkylamino"), amidino, hydrazine, hydrazone, carboxyl, sulfonic acid, phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The heteroaryl substituent used in the compound of the present disclosure refers to a cyclic aromatic system of 2 to 24 carbon atoms containing 1 to 4 heteroatoms selected from among N, O, P, Se, TE, Si, Ge and S. In the aromatic system, two or more rings may be fused. One or more hydrogen atoms on the heteroaryl may be substituted by the same substituents as on the aryl.

Examples of the alkyl substituent useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the alkoxy substituent useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present invention are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. One or more hydrogen atoms of the silyl may be substituted by the same substituent as in the aryl.

In the present disclosure, the phrase "(an organic layer) includes at least one organic compound" may be construed to mean "(an organic layer) may include a single organic compound species or two or more different species of organic compounds falling within the scope of the present disclosure".

Characterized by the sequential deposition of a light-emitting layer and an electron-density-controlling layer with the employment of at least one compound selected from among compounds represented by Chemical Formulas A to D in the electron-density-controlling layer and the compound represented by the following Chemical Formula H in the light-emitting layer, the organic light-emitting diode of the present disclosure exhibits improved luminance efficiency.

Here, the light-emitting layer of the organic light-emitting diode according to the present disclosure includes a host and a dopant, wherein the compound of Chemical Formula H may be used as the dopant.

As illustrated in Chemical Formula H, the anthracene compound useful in the present disclosure has a substituted or unsubstituted phenyl group as a substituent at position 9 and a linker L' as a substituent at position 10, the linker L' being linked to the dibenzofuran ring of the following diagram 1 at the position 1 or 2 of the dibenzofuran ring.

[Diagram 1]

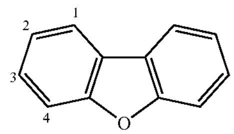

In one embodiment, the linker L' of Chemical Formula H may be a single bond or may be represented by the following Structural Formula 1 or 2, where each of the unsubstituted carbon atoms of the aromatic ring moiety is bound with a hydrogen atom or a deuterium atom.

[Structural Formula 1]

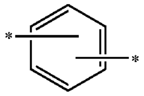

[Structural Formula 2]

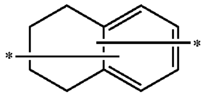

Concrete examples of the compound represented by Chemical Formula H include, but are not limited to, the compounds represented by the following Compounds 1 to 156.

<Cpd. 1>

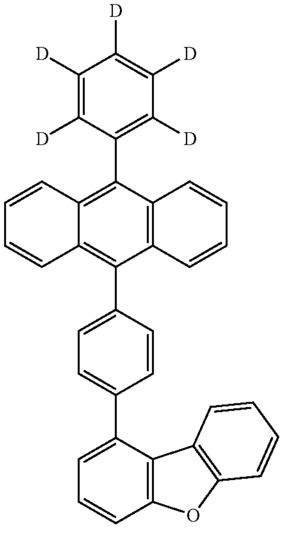

-continued

<Cpd. 2>

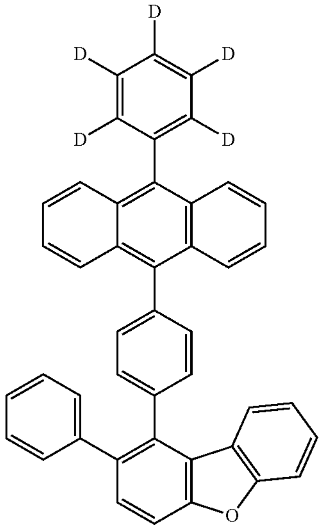

<Cpd. 3>

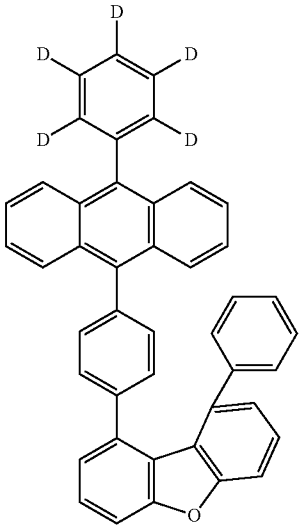

<Cpd. 4>

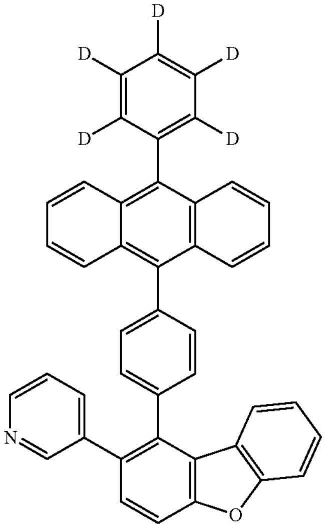

-continued
<Cpd. 5>
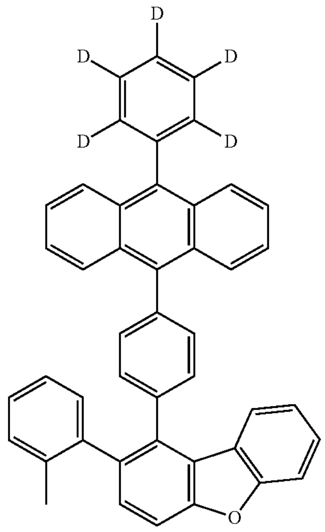
<Cpd. 6>
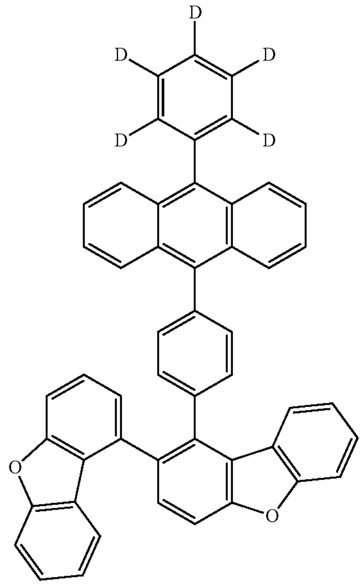
<Cpd. 7>
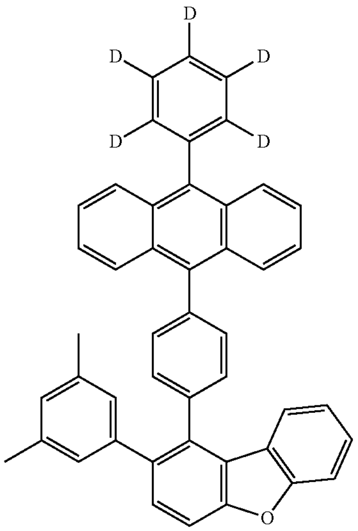
-continued
<Cpd. 8>
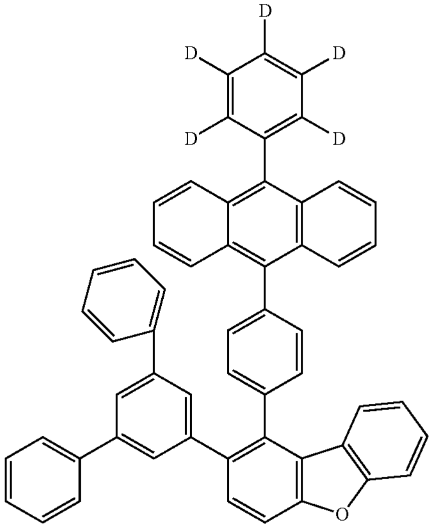
<Cpd. 9>
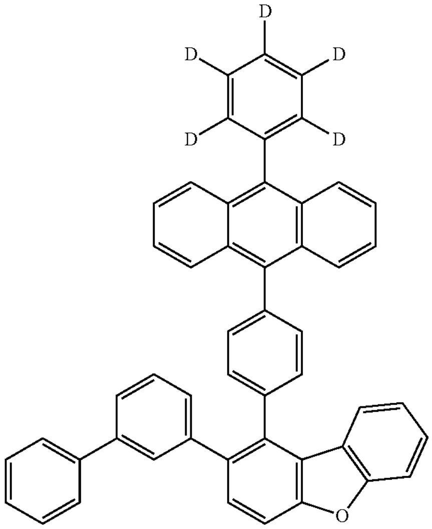
<Cpd. 10>
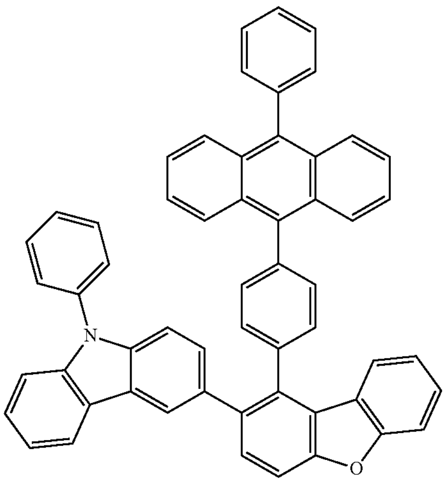

-continued
<Cpd. 11>
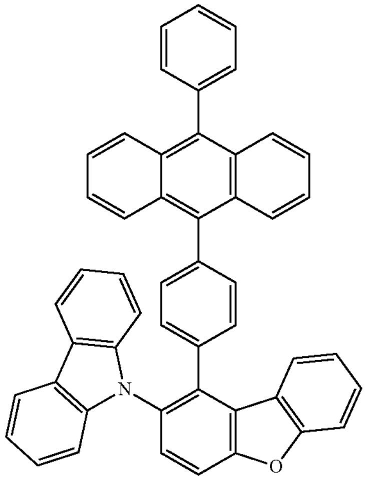
<Cpd. 12>
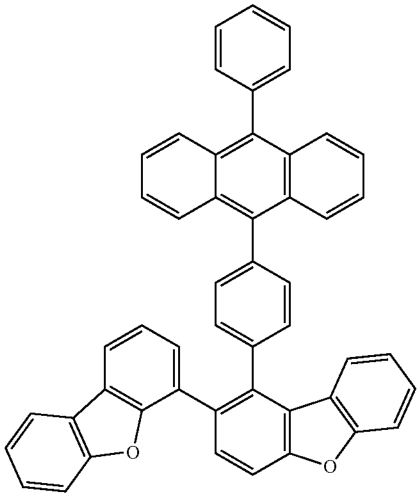
<Cpd. 13>
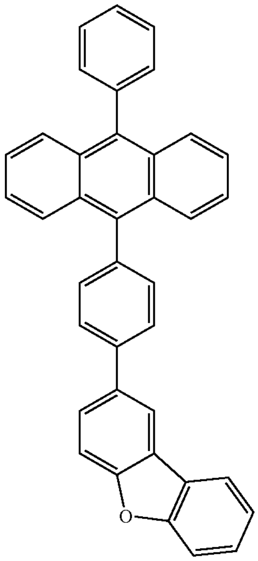
-continued
<Cpd. 14>
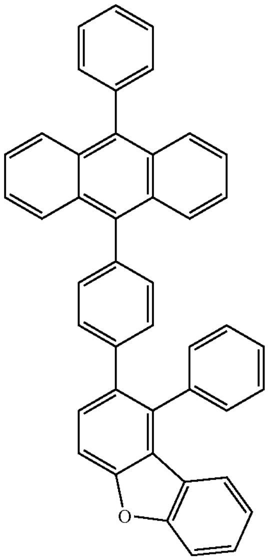
<Cpd. 15>
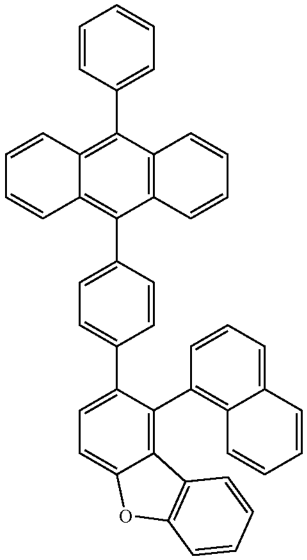

-continued
<Cpd. 16>
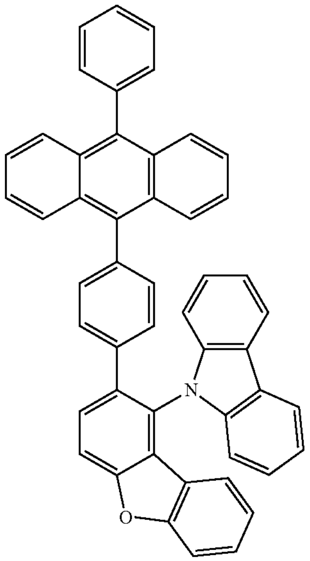
<Cpd. 17>
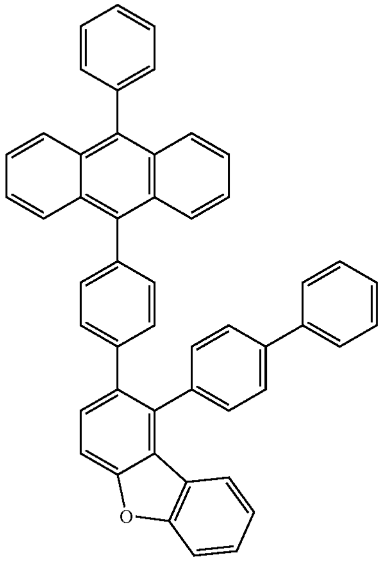
-continued
<Cpd. 18>
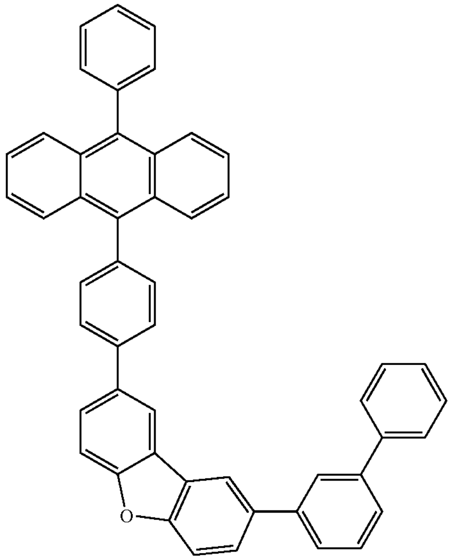
<Cpd. 19>
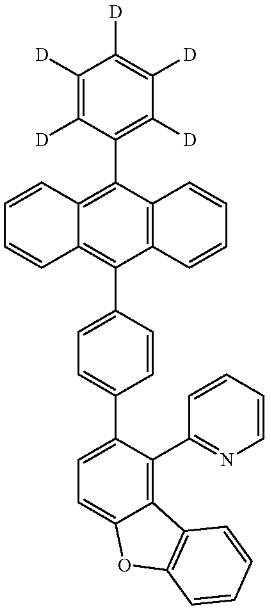

-continued
<Cpd. 20>
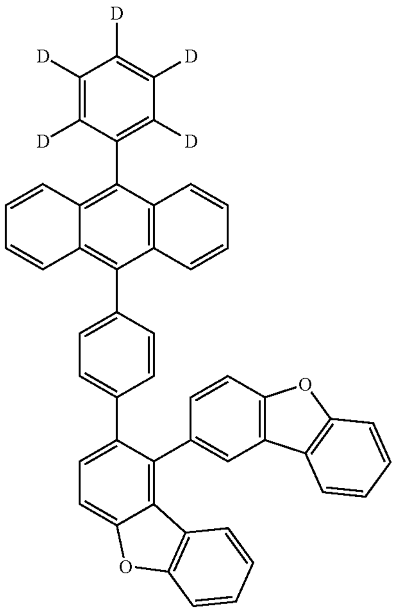
<Cpd. 21>
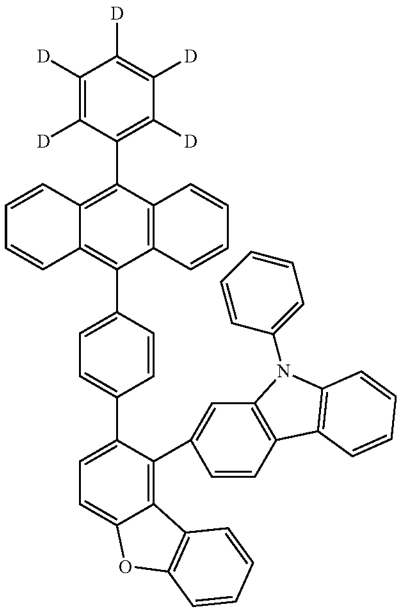
-continued
<Cpd. 22>
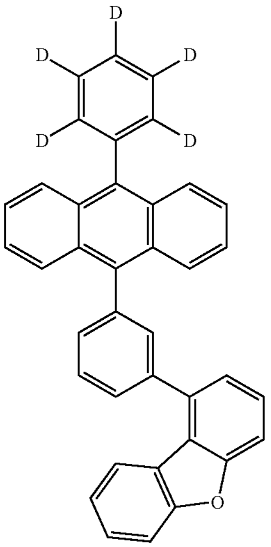
<Cpd. 23>
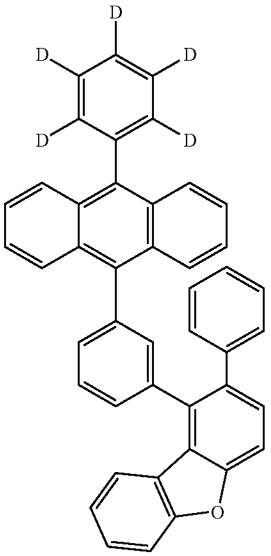
<Cpd. 24>
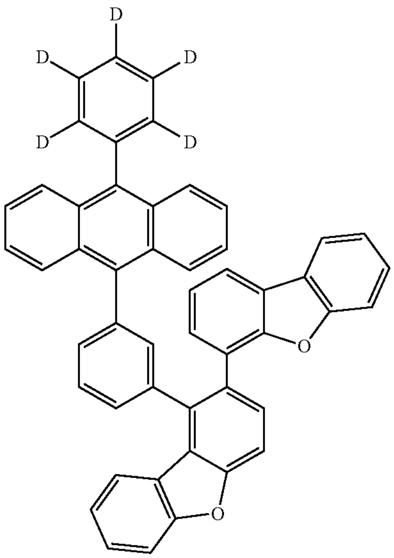

-continued
<Cpd. 25>
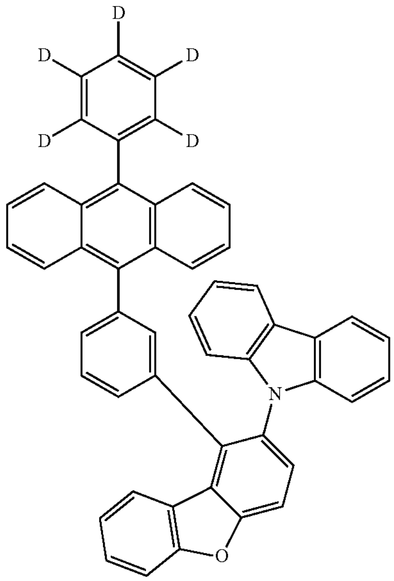
<Cpd. 26>
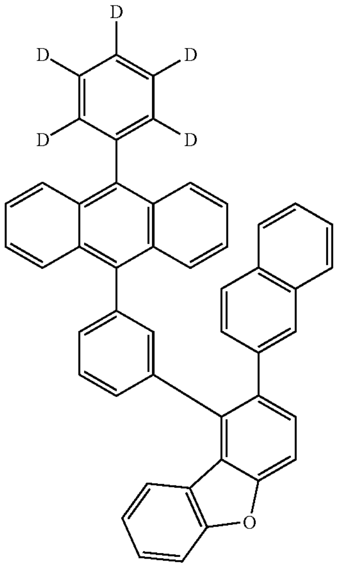
-continued
<Cpd. 27>
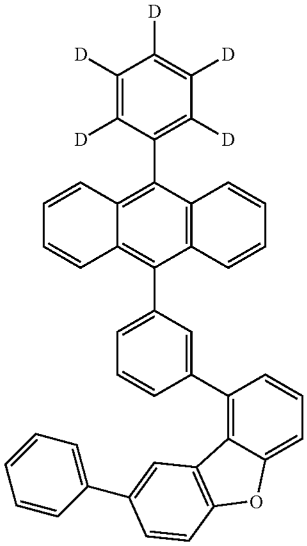
<Cpd. 28>
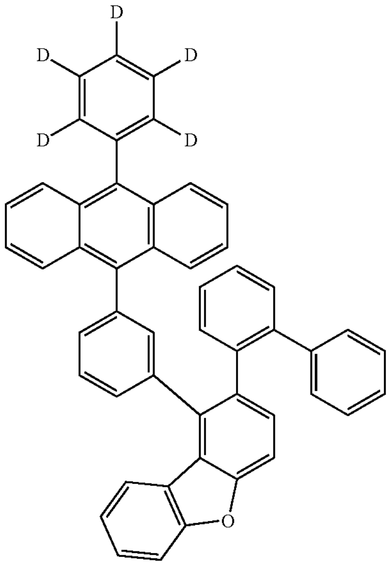

-continued
<Cpd. 29>
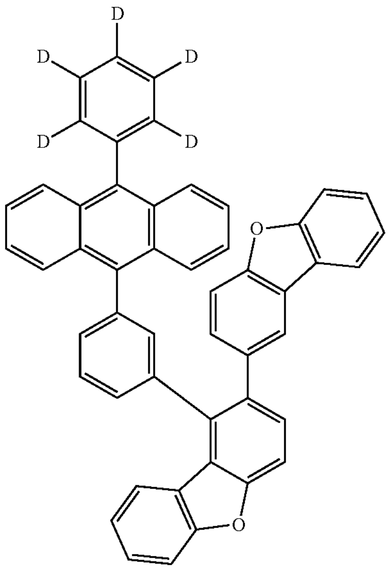
<Cpd. 30>
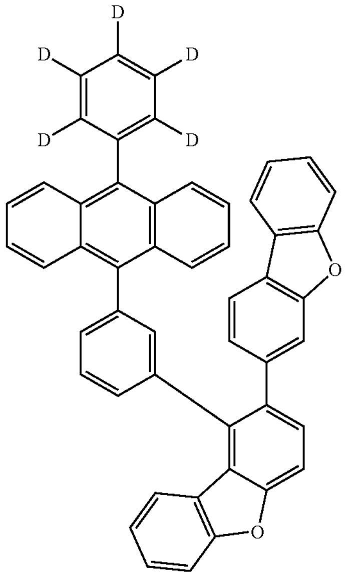
-continued
<Cpd. 31>
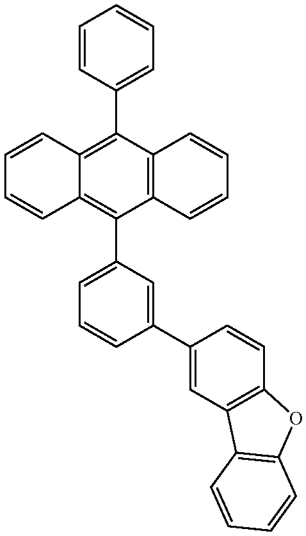
<Cpd. 32>
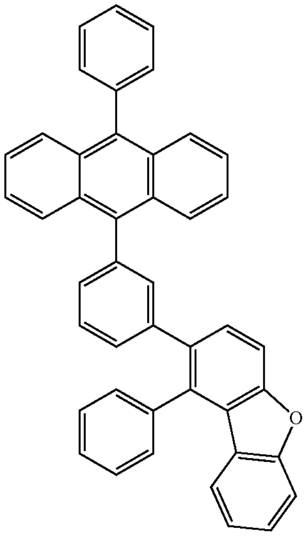
<Cpd. 33>
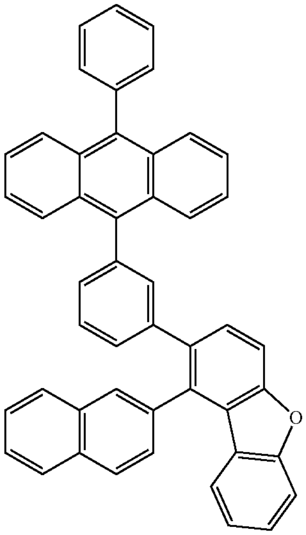

-continued
<Cpd. 34>
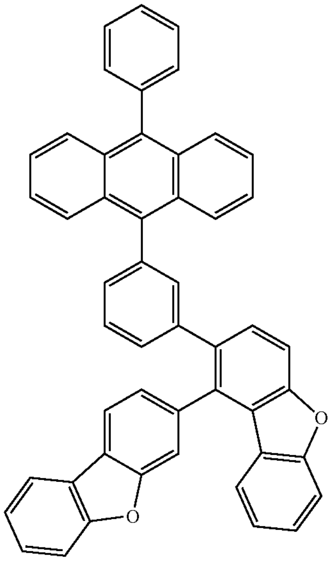
<Cpd. 35>
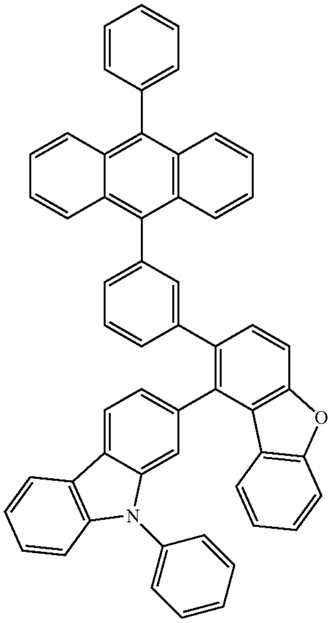
-continued
<Cpd. 36>
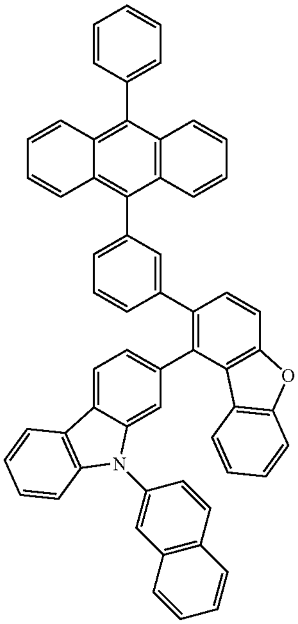
<Cpd. 37>
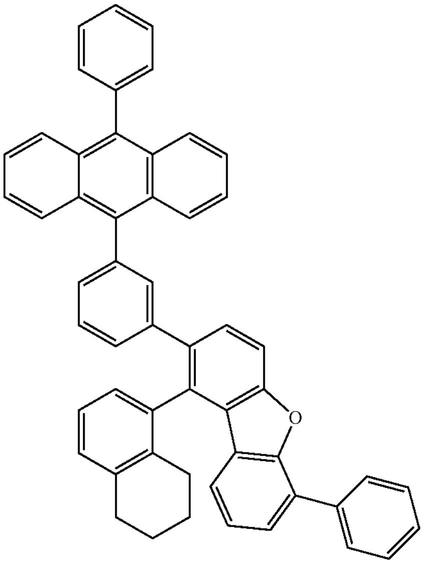

-continued
<Cpd.38>
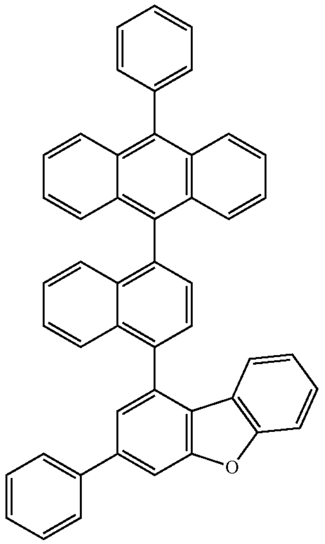
<Cpd. 39>
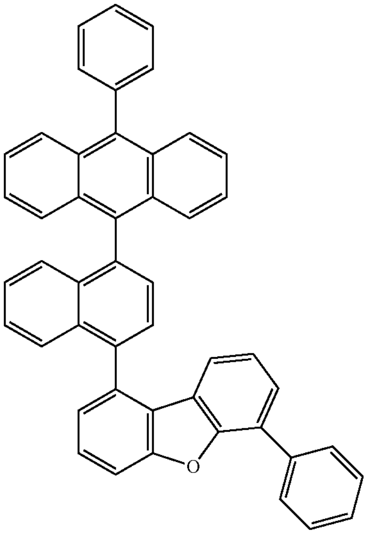
<Cpd. 40>
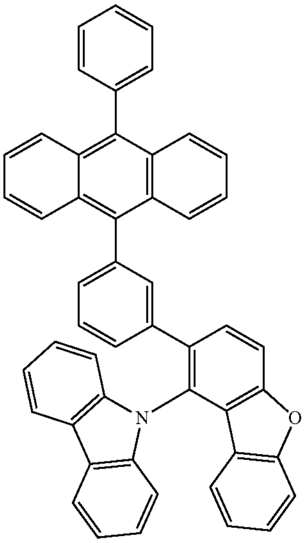
-continued
<Cpd. 41>
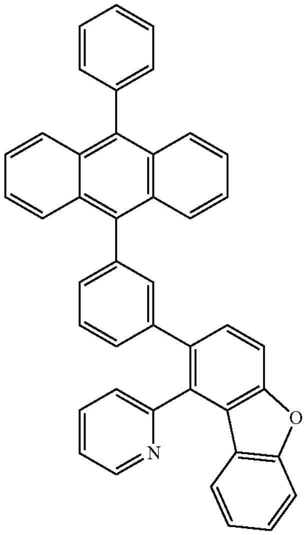
<Cpd. 42>
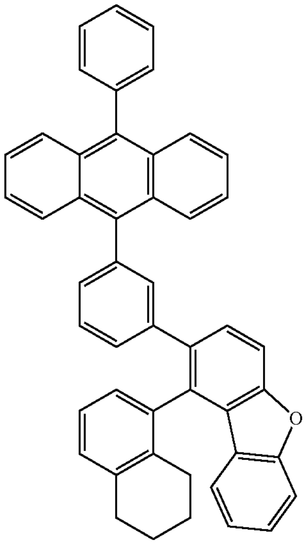
<Cpd. 43>
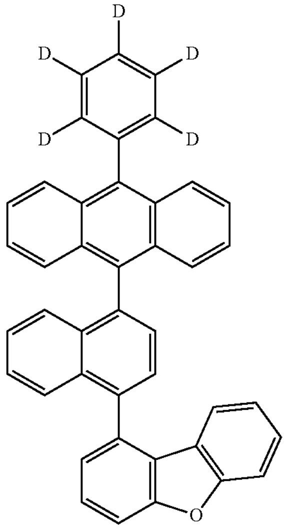

-continued
<Cpd. 44>
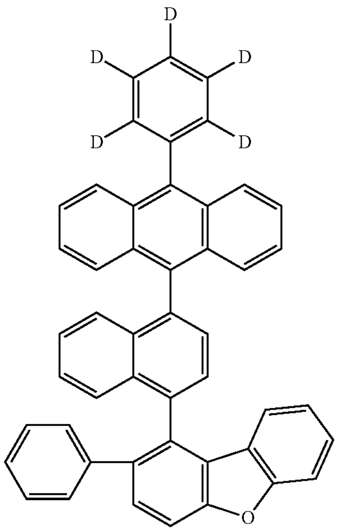
-continued
<Cpd. 46>
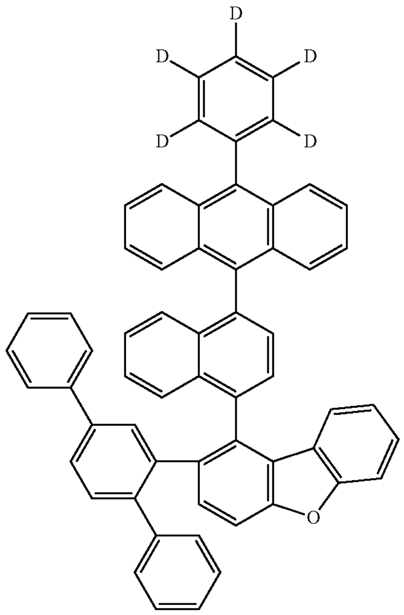
<Cpd. 45>
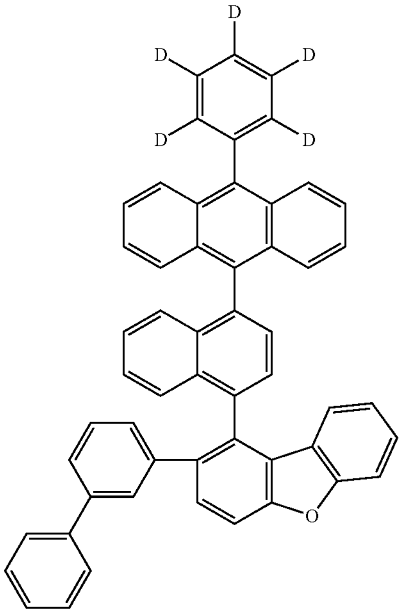
<Cpd. 47>
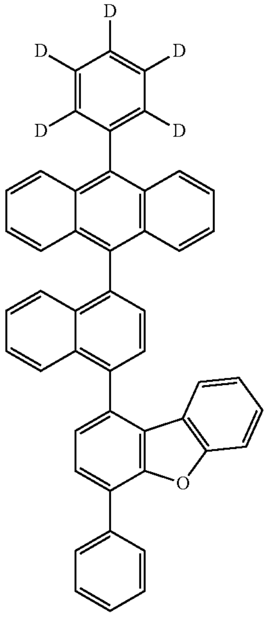

-continued
<Cpd. 48>
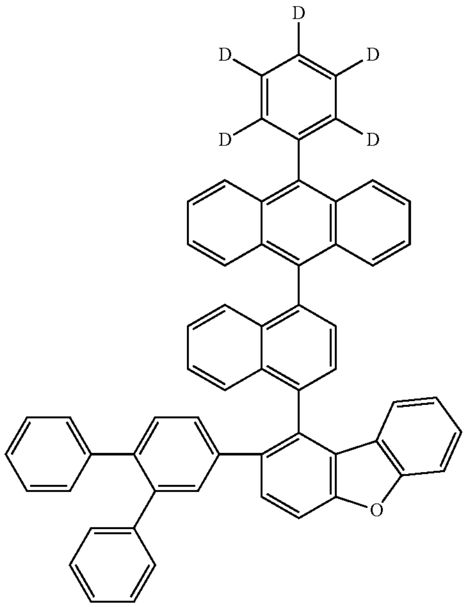
<Cpd. 49>
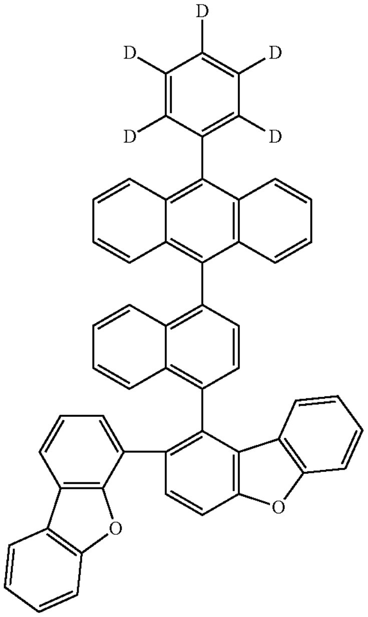
-continued
<Cpd. 50>
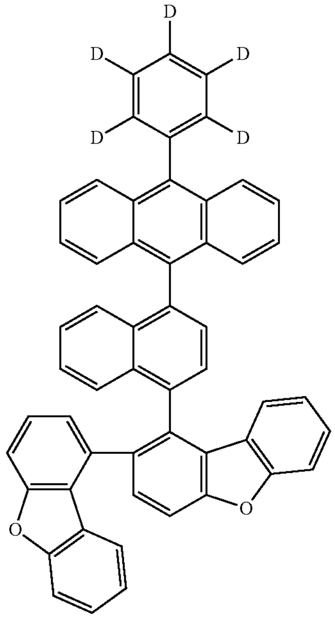
<Cpd. 51>
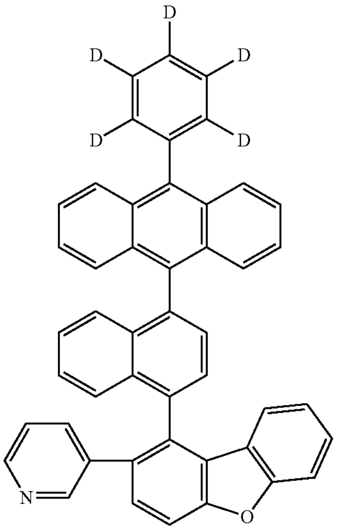

-continued
<Cpd. 52>
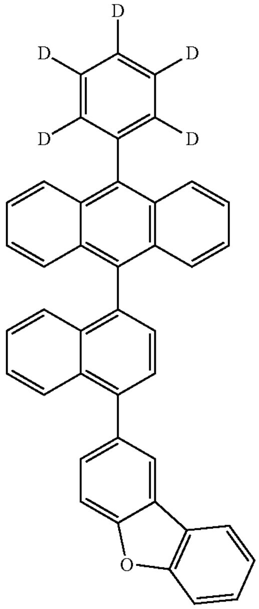
<Cpd. 53>
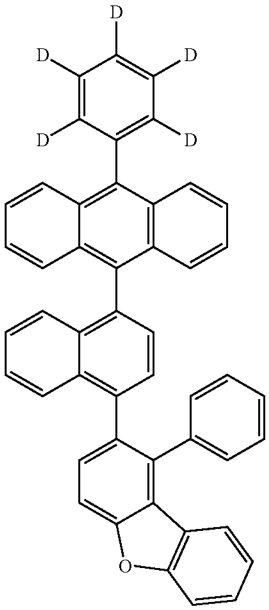
-continued
<Cpd. 54>
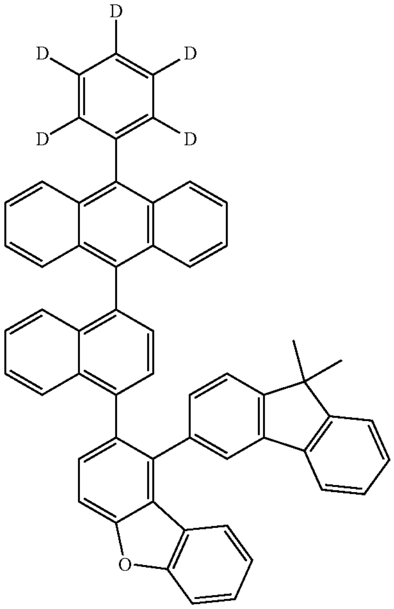
<Cpd. 55>
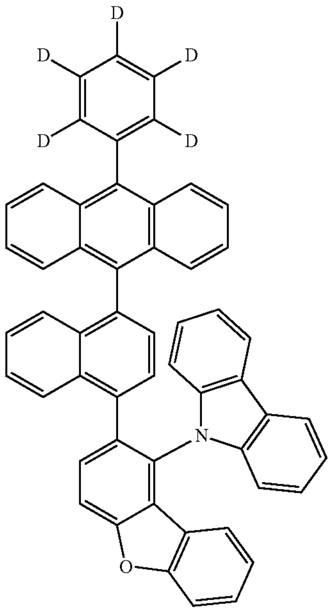

-continued
<Cpd. 56>
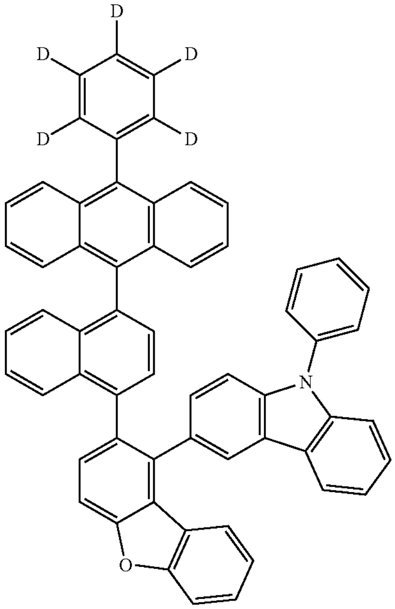
-continued
<Cpd. 58>
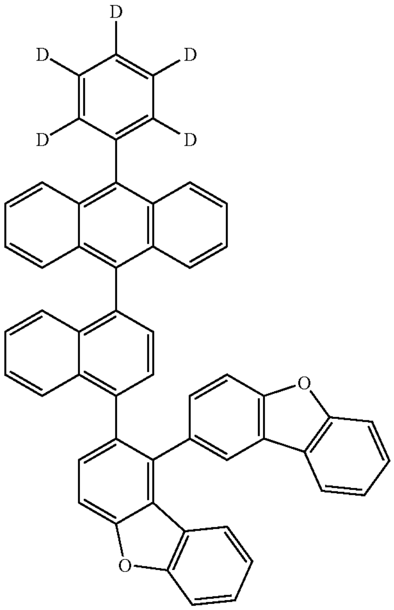
<Cpd. 57>
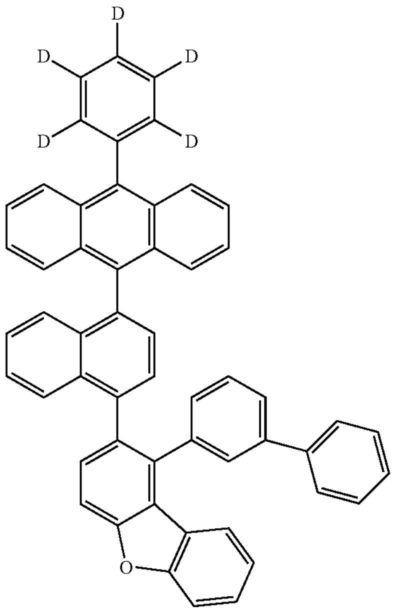
<Cpd. 59>
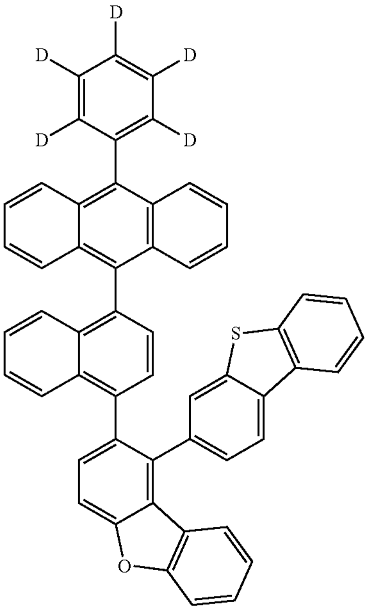

-continued
<Cpd. 60>
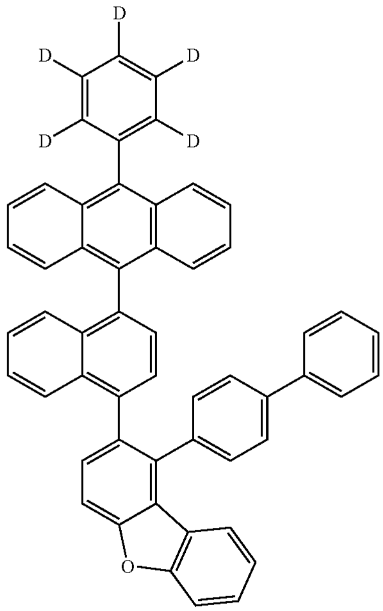
<Cpd. 61>
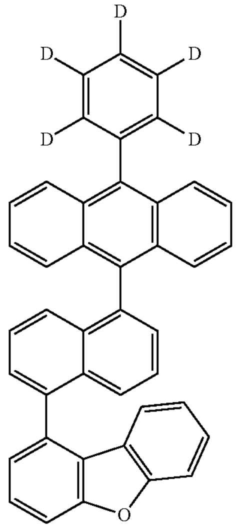
<Cpd. 62>
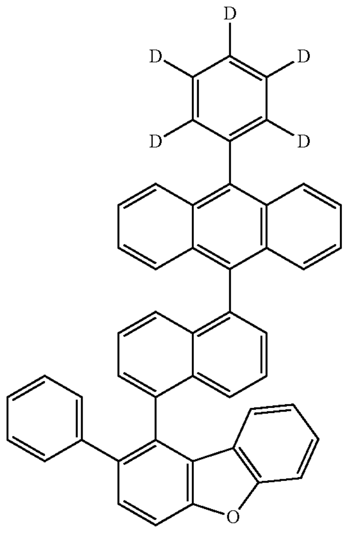
-continued
<Cpd. 63>
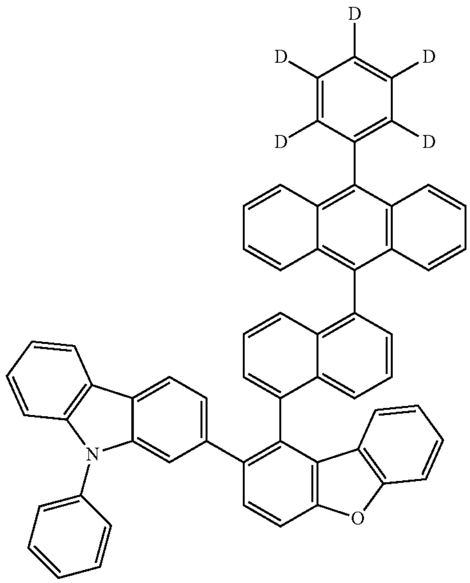
<Cpd. 64>
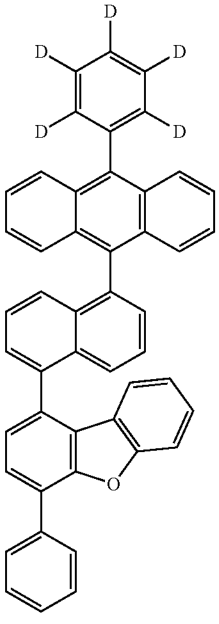

<Cpd. 65>
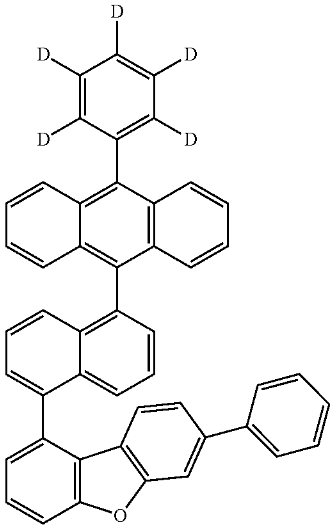
<Cpd. 66>
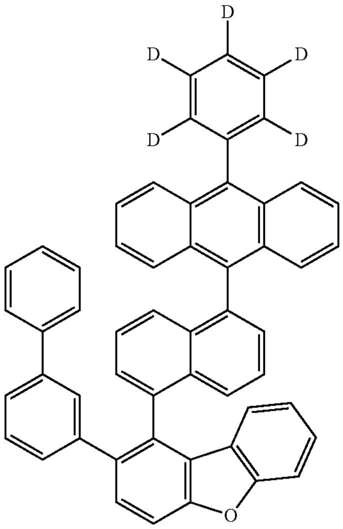
<Cpd. 67>
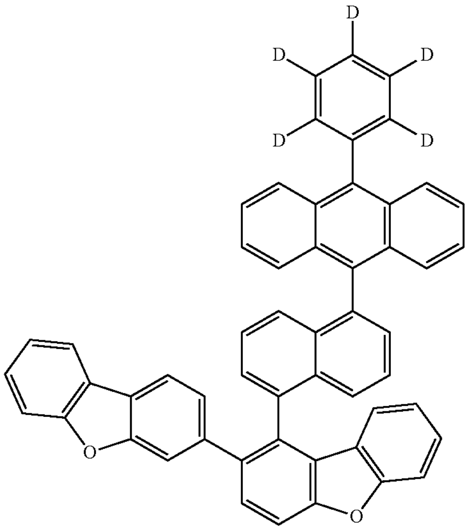
<Cpd. 68>
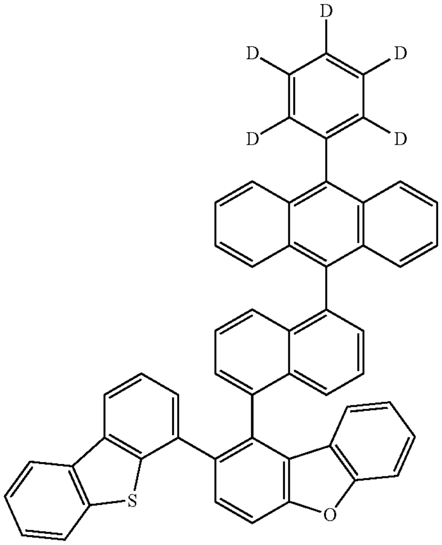
<Cpd. 69>
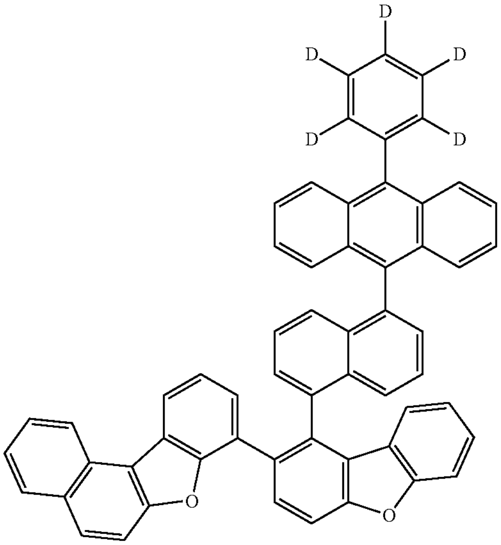

-continued
<Cpd. 70>
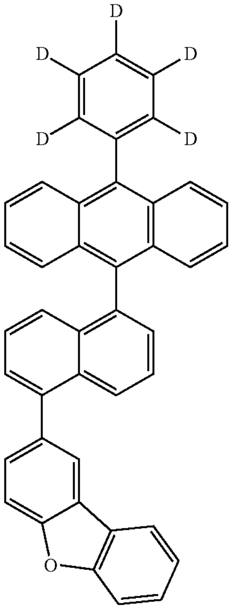
<Cpd. 71>
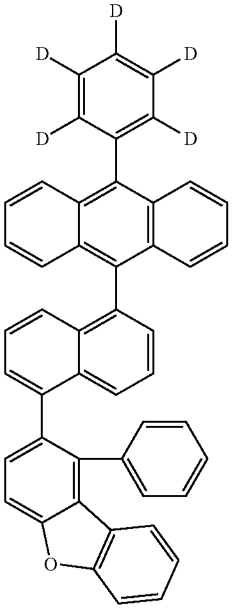
-continued
<Cpd. 72>
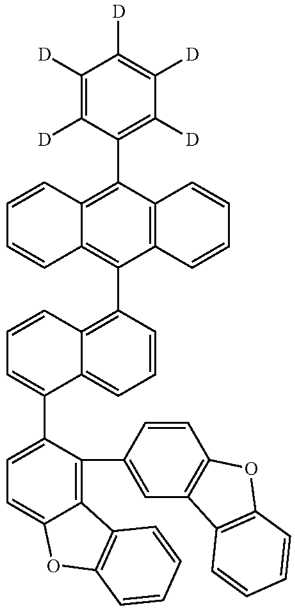
<Cpd. 73>
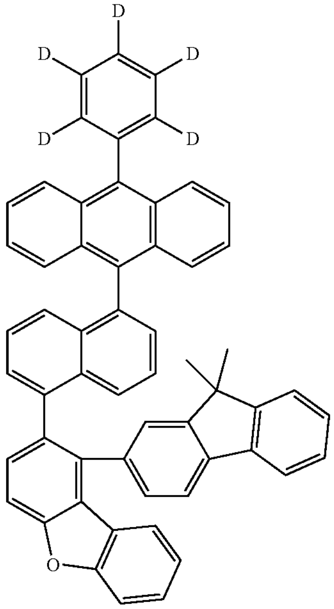

-continued
<Cpd. 74>
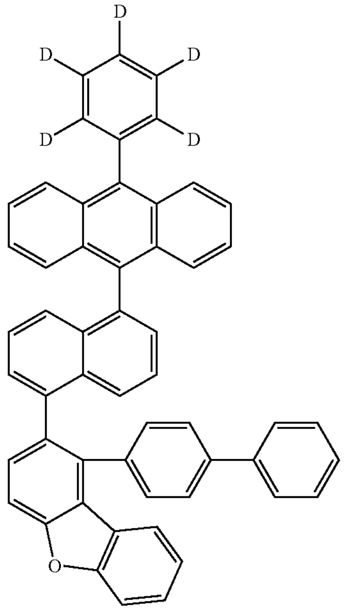
<Cpd. 75>
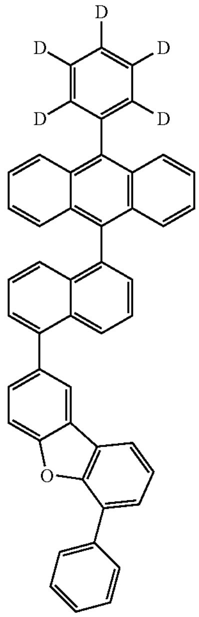
-continued
<Cpd. 76>
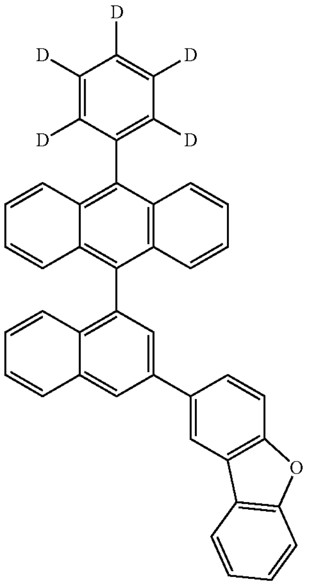
<Cpd. 77>
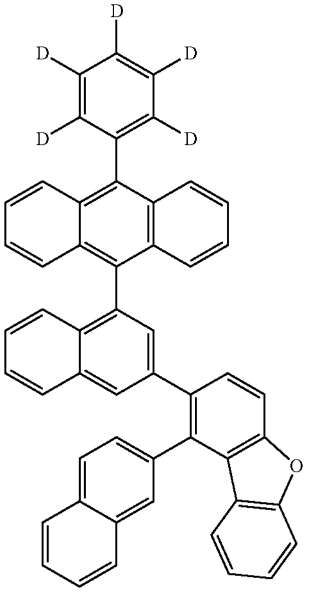

-continued
<Cpd. 78>
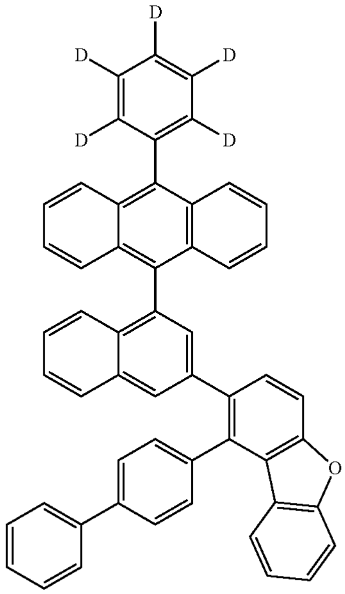
<Cpd. 79>
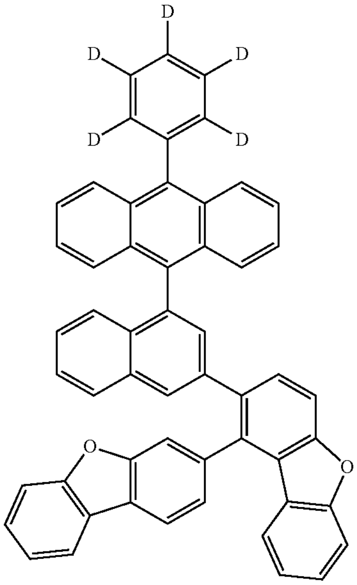
-continued
<Cpd. 80>
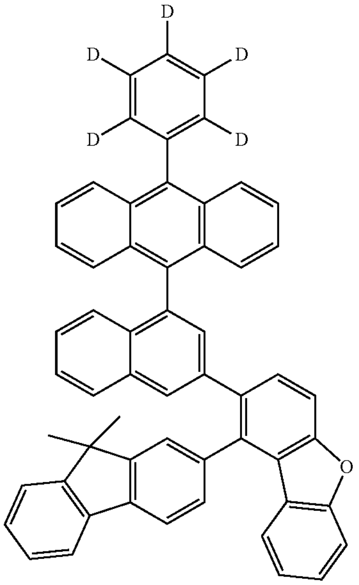
<Cpd. 81>
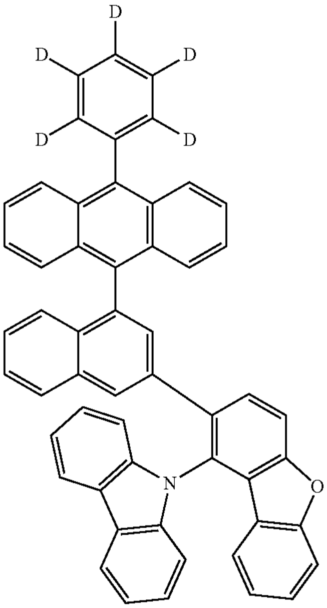

-continued
<Cpd. 82>
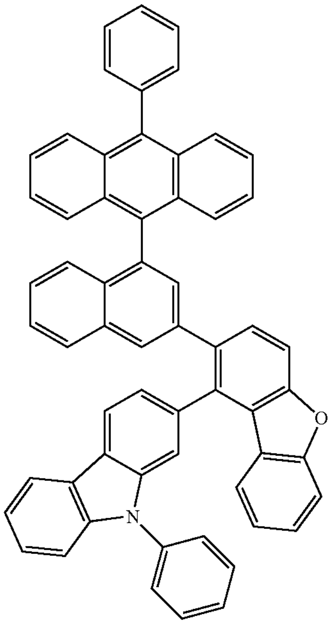
<Cpd. 83>
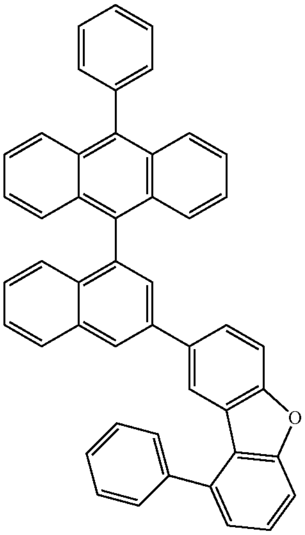
<Cpd. 84>
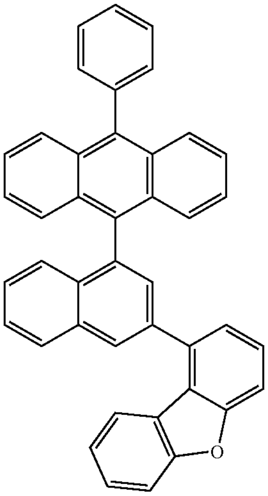
-continued
<Cpd. 85>
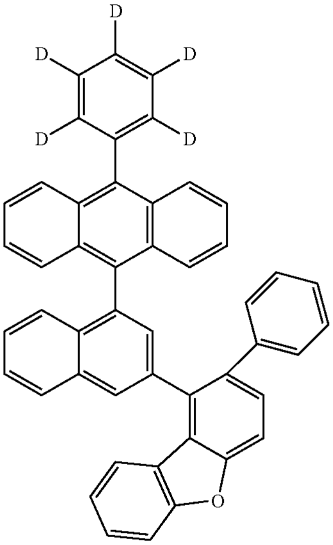
<Cpd. 86>
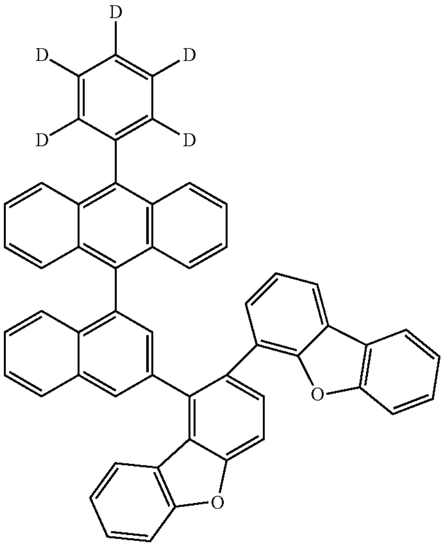

-continued
<Cpd. 87>
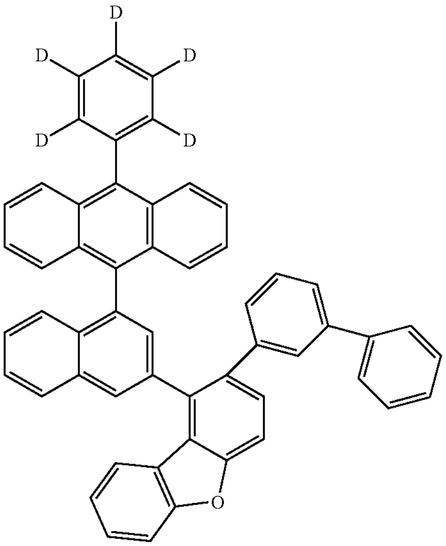
<Cpd. 88>
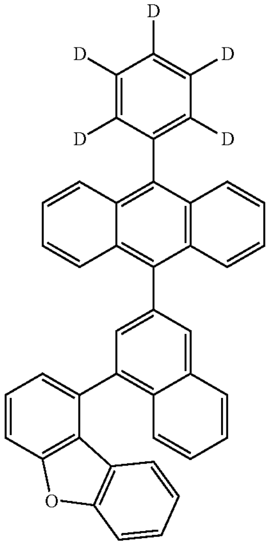
<Cpd. 89>
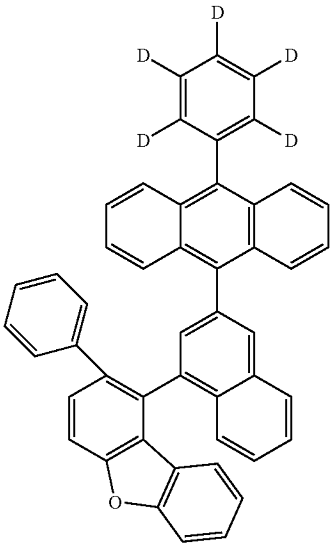
-continued
<Cpd. 90>
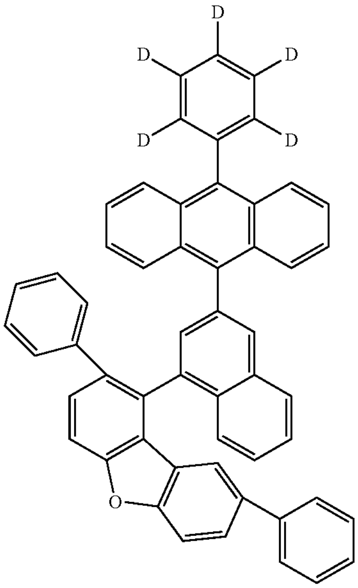
<Cpd. 91>
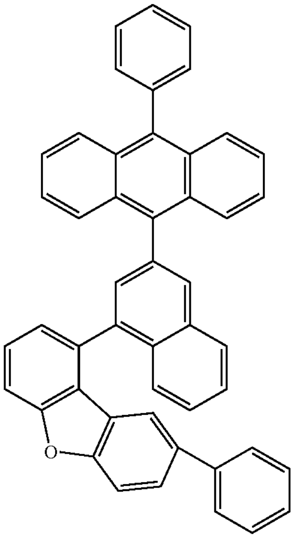

-continued
<Cpd. 92>
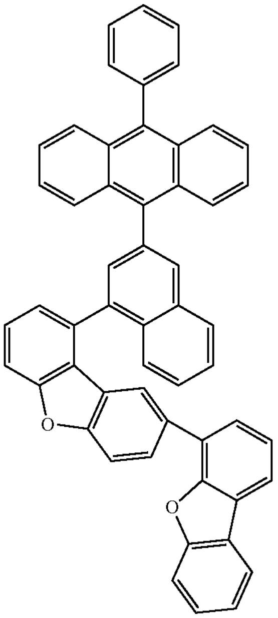
<Cpd. 93>
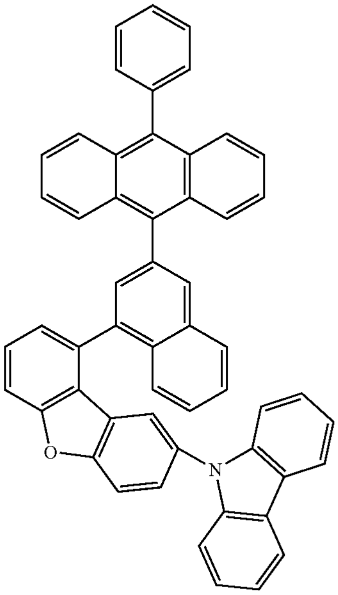
-continued
<Cpd. 94>
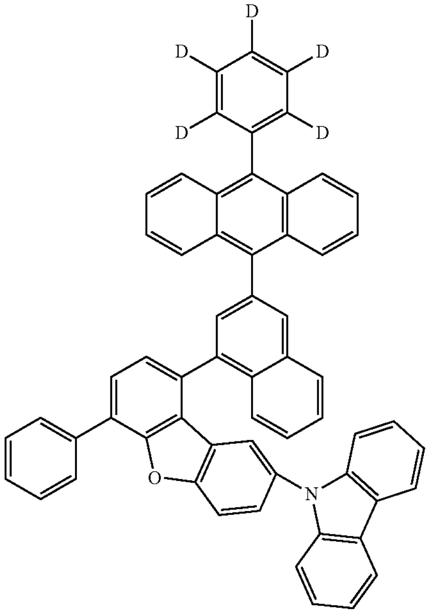
<Cpd. 95>
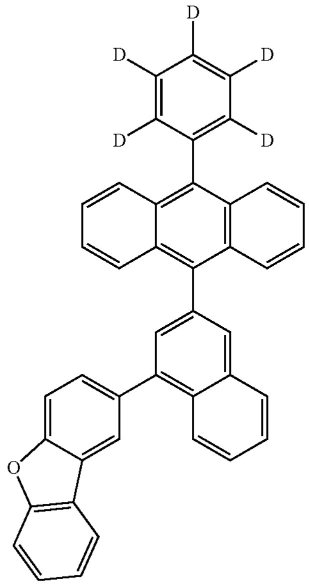

-continued
<Cpd. 96>
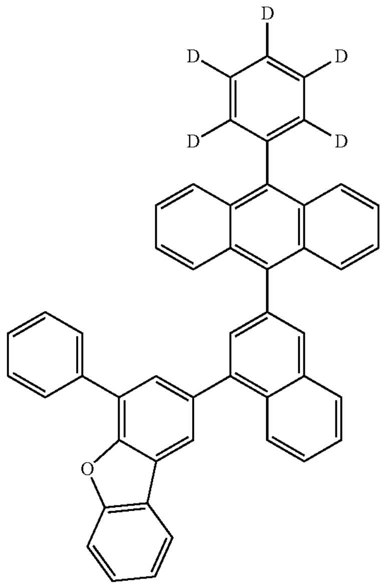
<Cpd. 97>
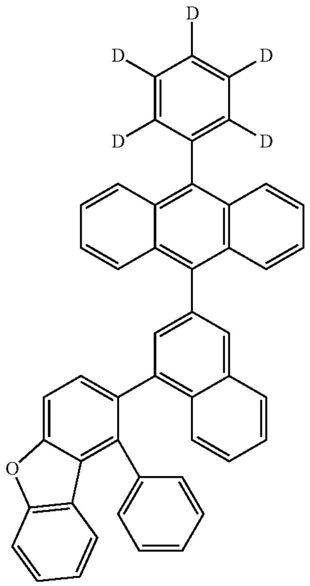
-continued
<Cpd. 98>
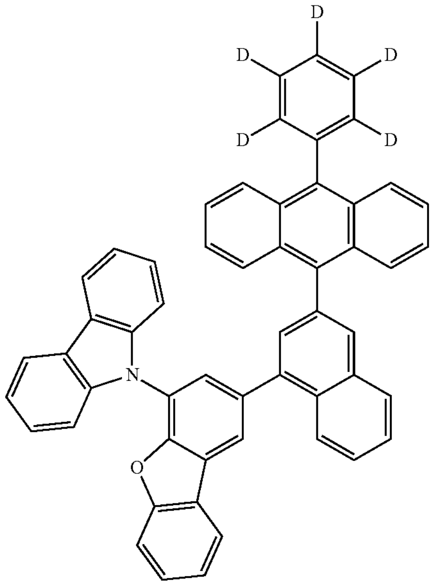
<Cpd. 99>
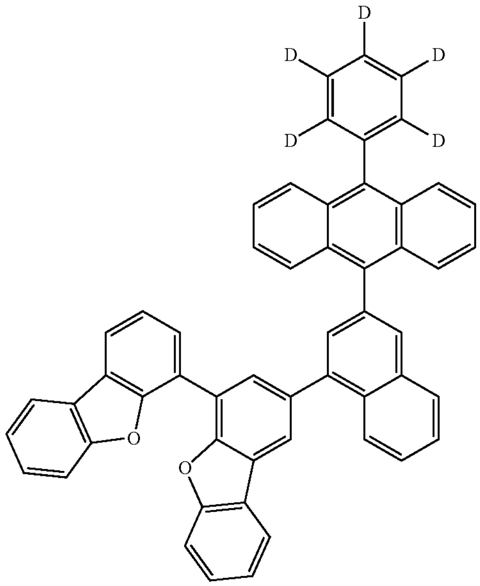
<Cpd. 100>
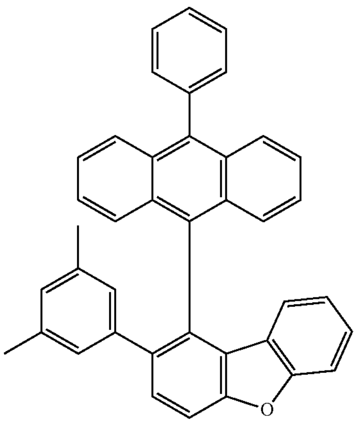

-continued
<Cpd. 101>
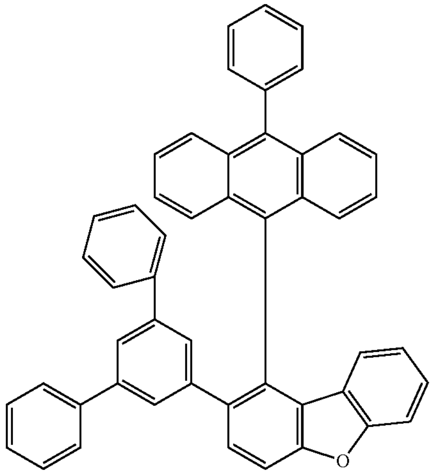
<Cpd. 102>
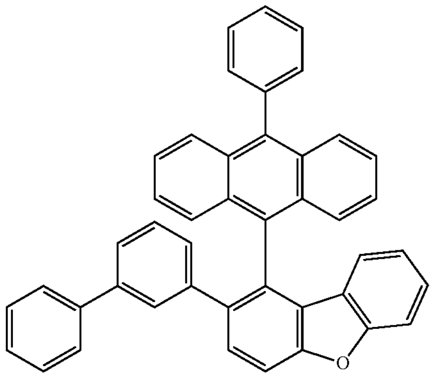
<Cpd. 103>
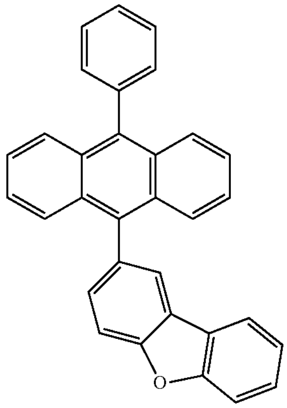
-continued
<Cpd. 104>
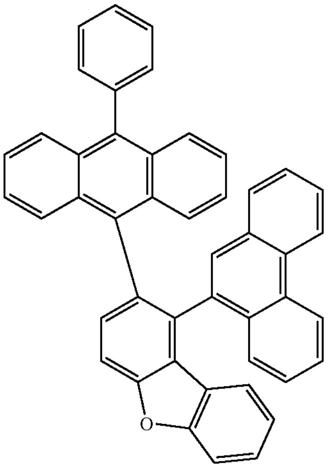
<Cpd. 105>
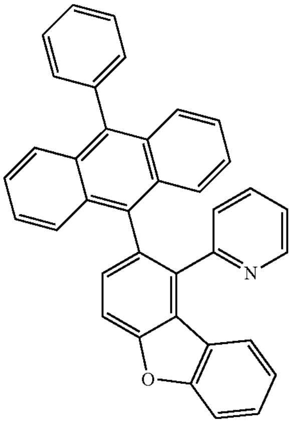
<Cpd. 106>
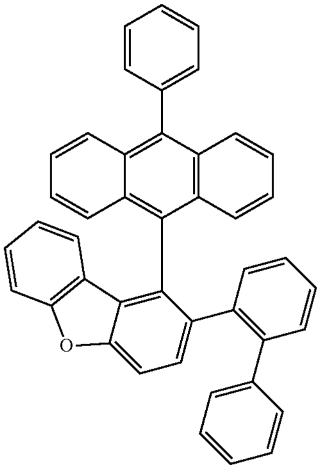

-continued
<Cpd. 107>
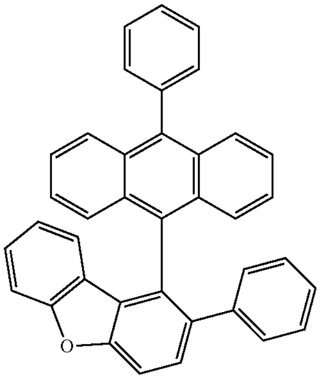
<Cpd. 108>
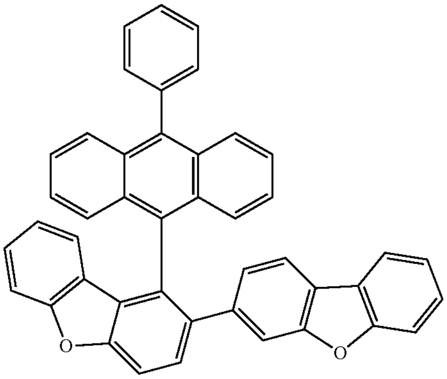
<Cpd. 109>
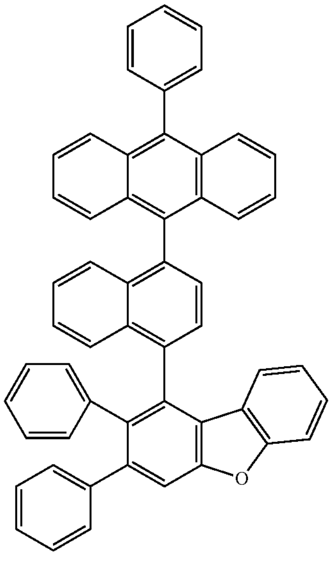
-continued
<Cpd. 110>
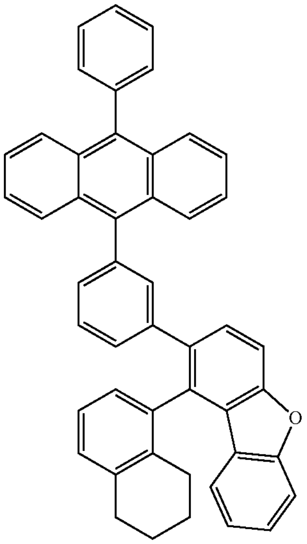
<Cpd. 111>
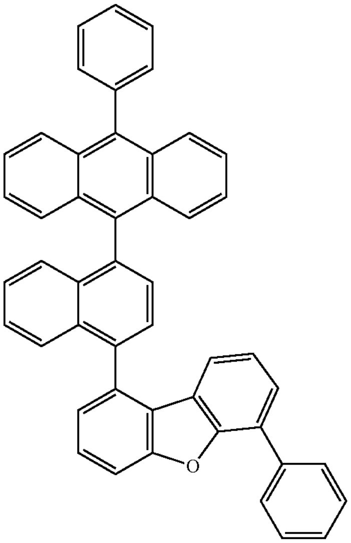

-continued
<Cpd. 112>
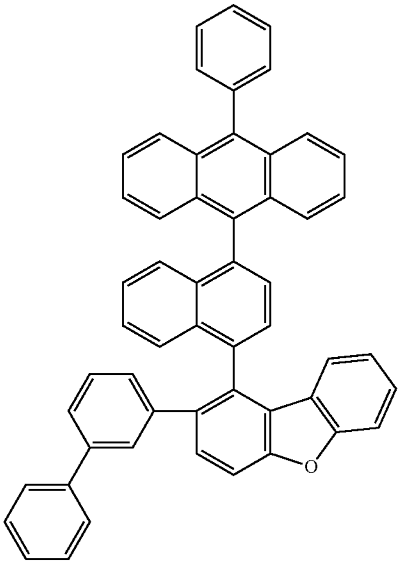
<Cpd. 113>
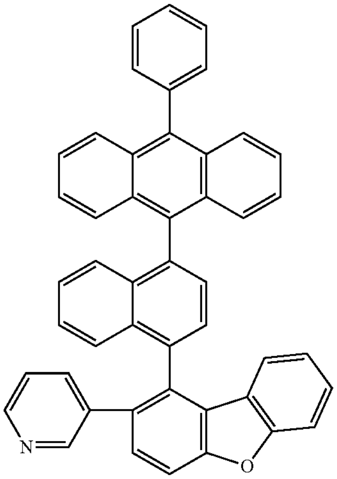
-continued
<Cpd. 114>
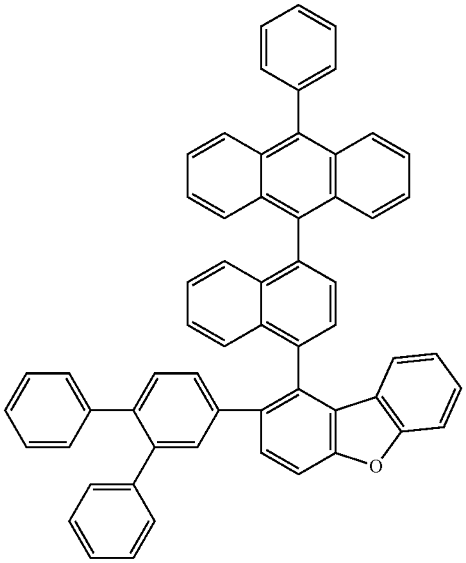
<Cpd. 115>
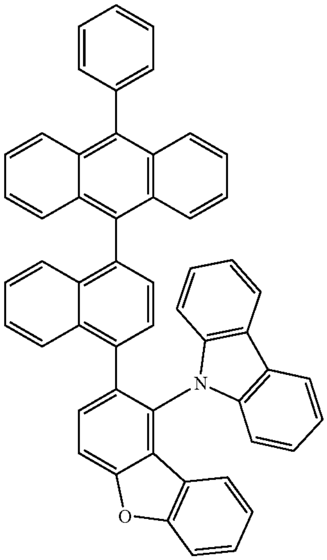

-continued
<Cpd. 116>
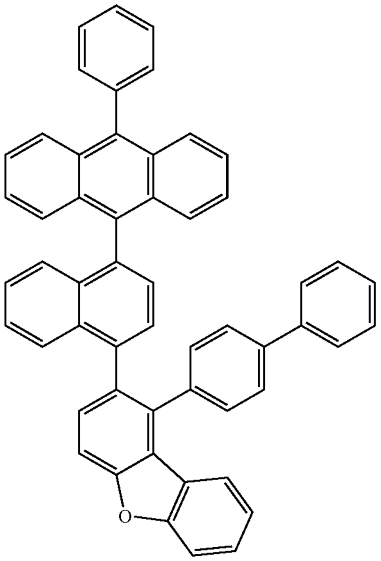
<Cpd. 117>
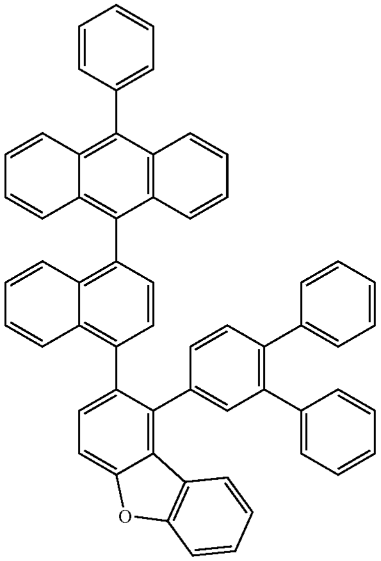
<Cpd. 118>
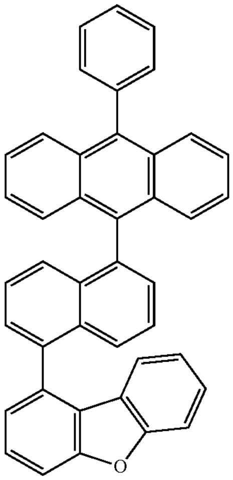
-continued
<Cpd. 119>
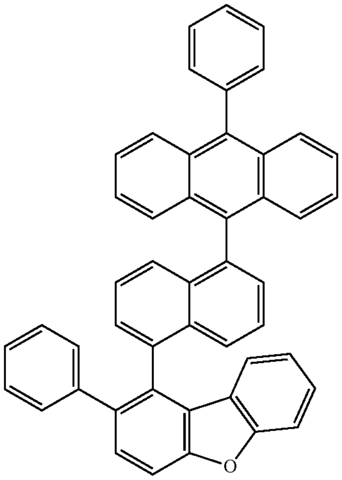
<Cpd. 120>
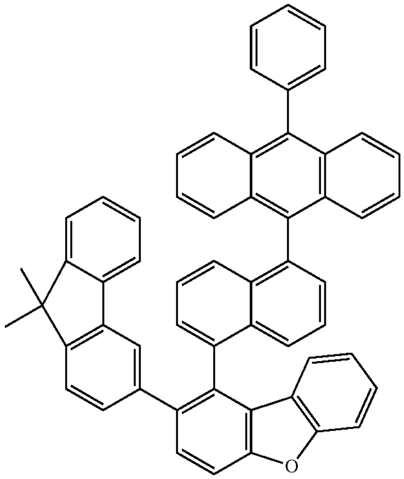
<Cpd. 121>
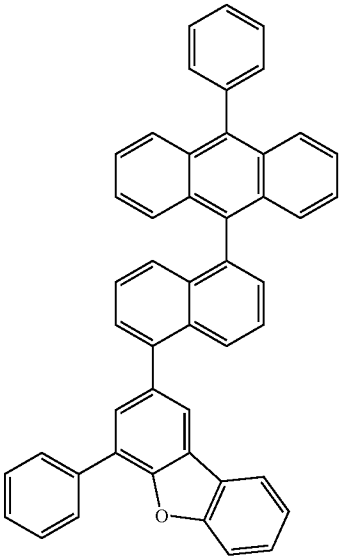

-continued
<Cpd. 122>
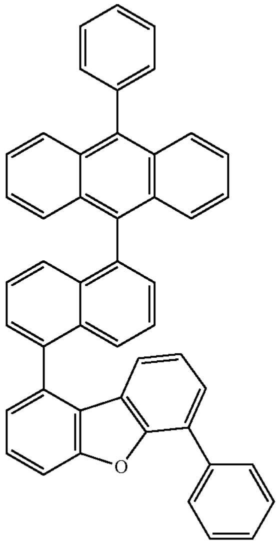
<Cpd.123>
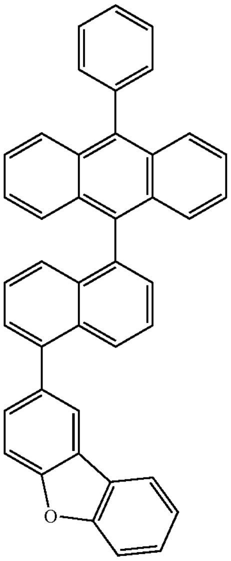
<Cpd. 124>
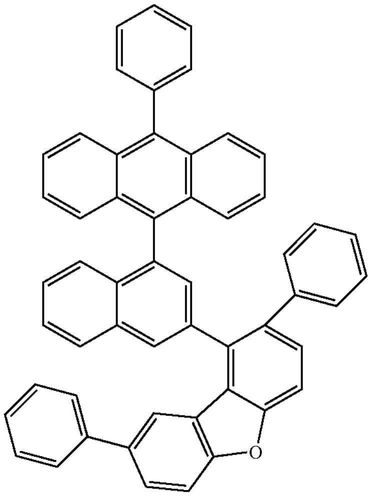
-continued
<Cpd. 125>
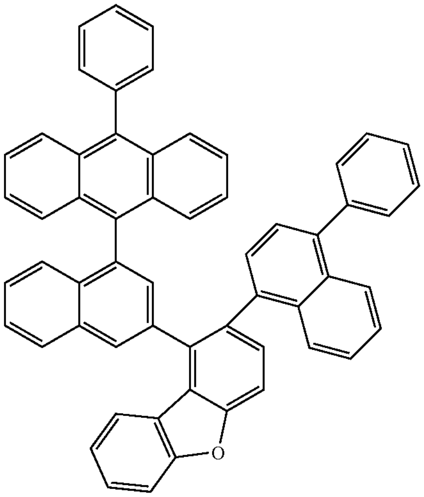
<Cpd. 126>
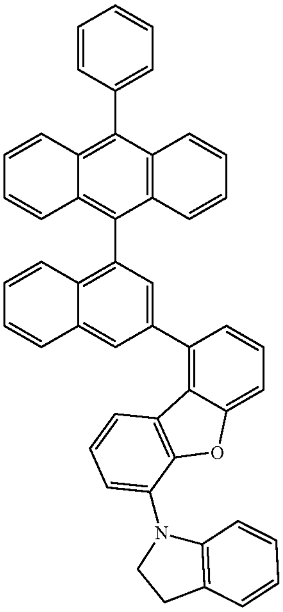

-continued
<Cpd. 127>
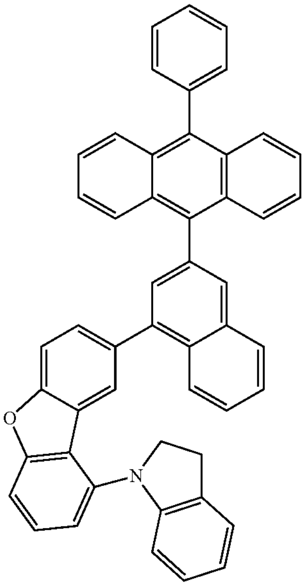
<<Cpd. 128>
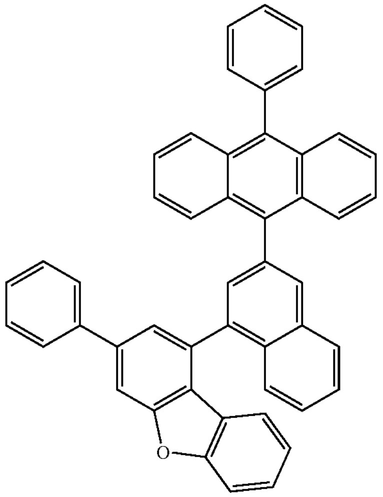
<Cpd. 129>
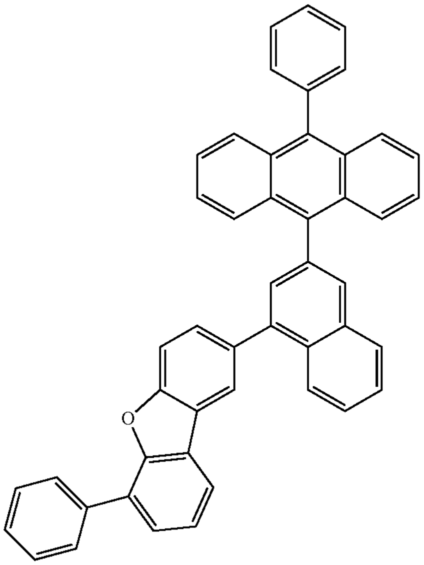
-continued
<Cpd. 130>
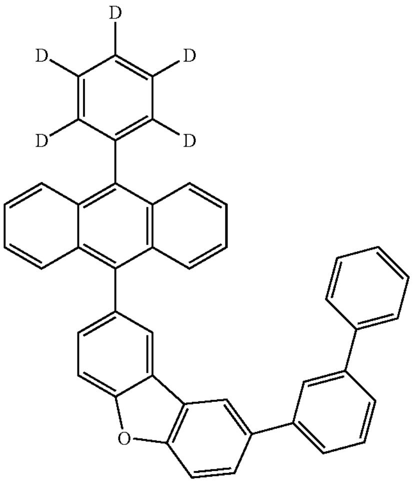
<Cpd. 131>
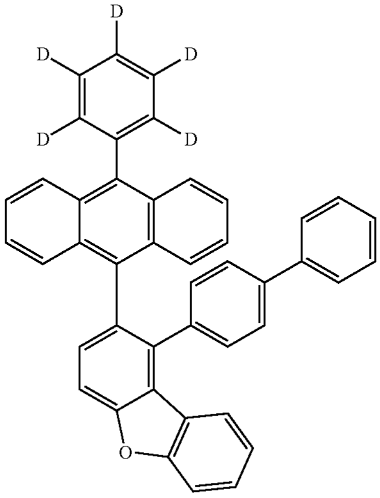
<Cpd. 132>
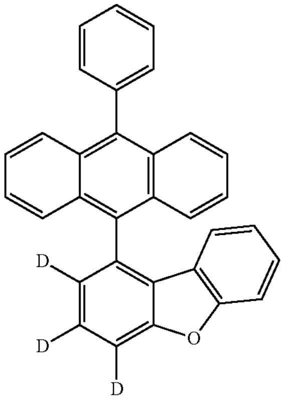

-continued
<Cpd. 133>
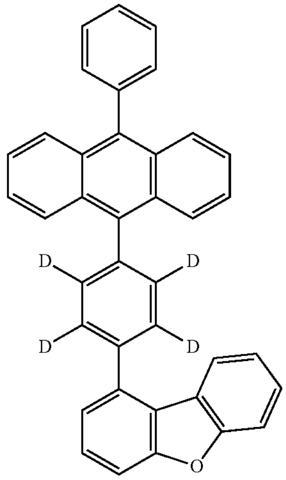
<Cpd. 134>
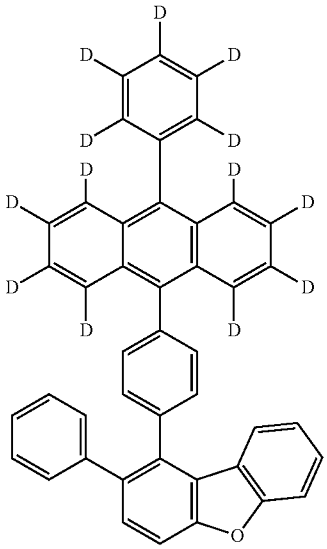
<Cpd. 135>
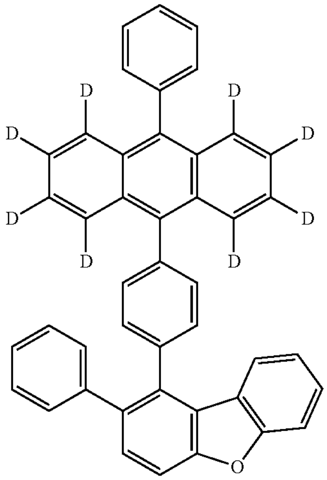
-continued
<Cpd. 136>
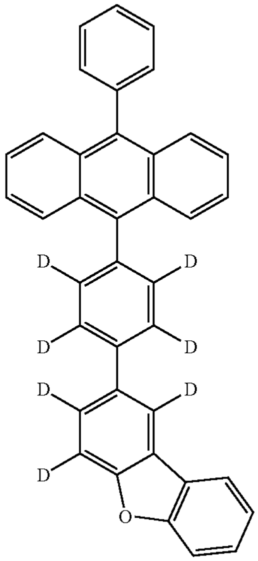
<Cpd. 137>
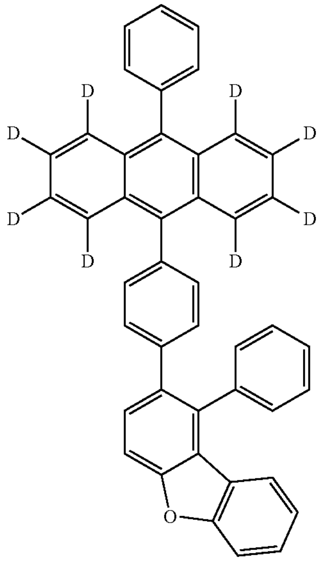

-continued
<Cpd. 138>
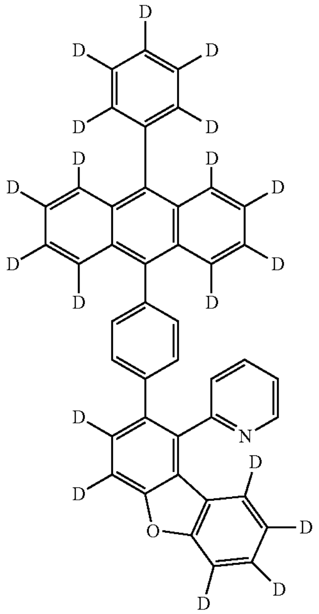
<Cpd. 139>
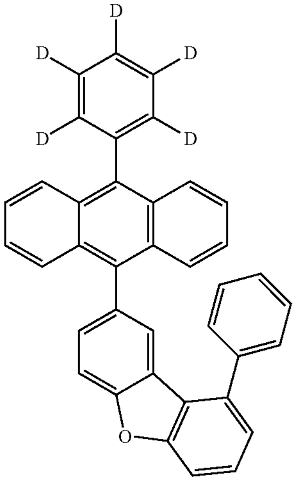
-continued
<Cpd. 140>
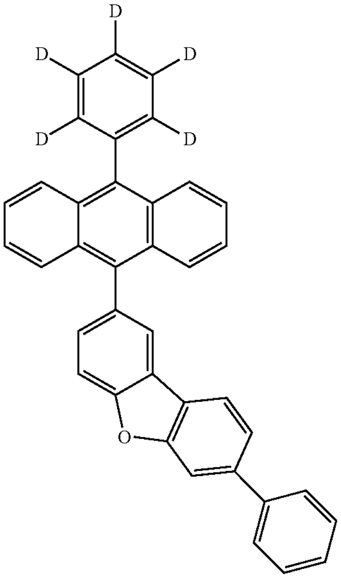
<Cpd. 141>
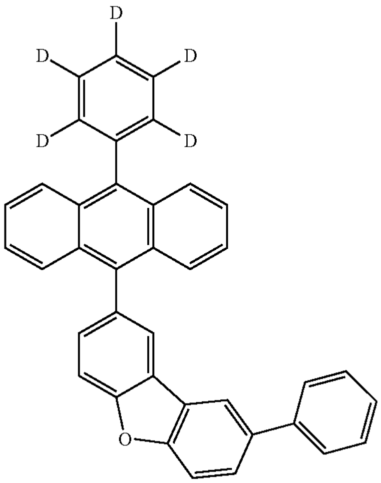
<Cpd. 142>
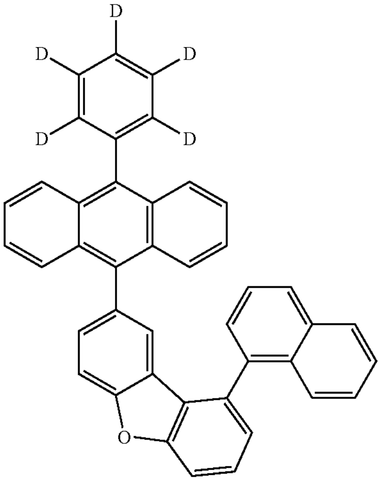

-continued
<Cpd. 143>
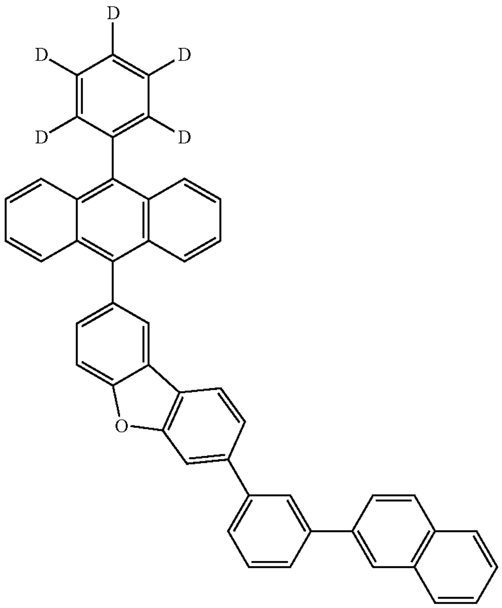
<Cpd. 144>
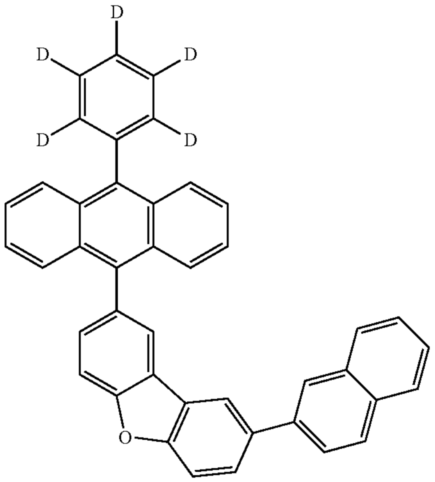
<Cpd. 145>
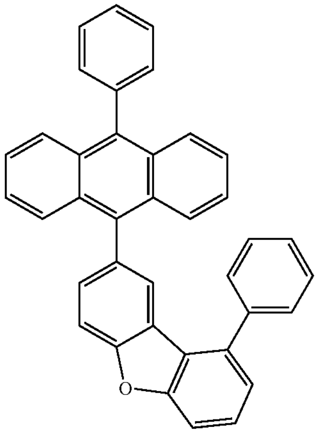
-continued
<Cpd. 146>
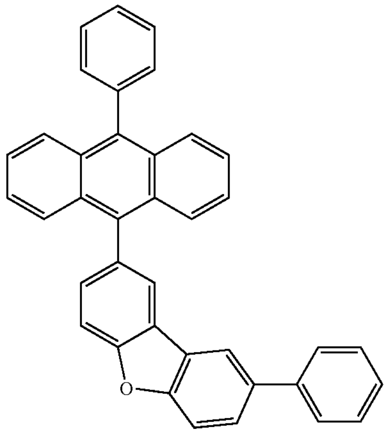
<Cpd. 147>
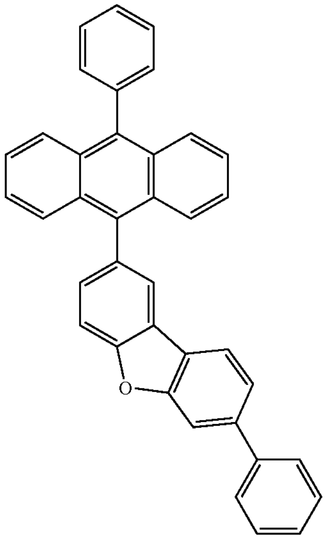
<Cpd.148>
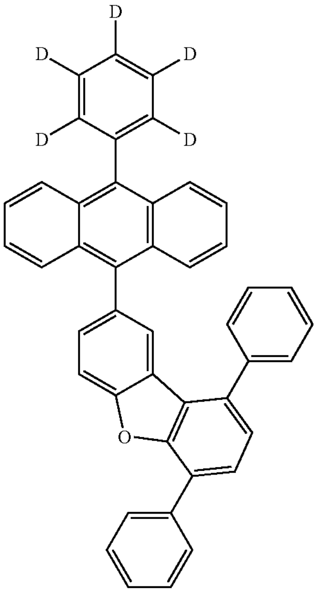

<Cpd. 149>
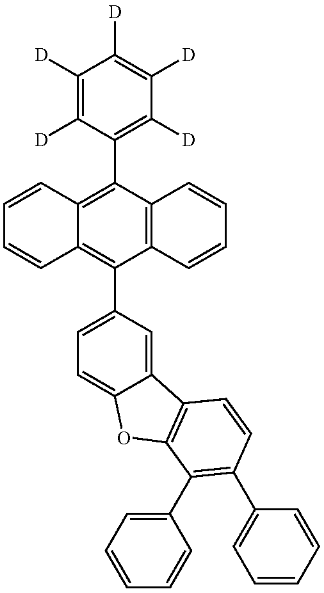
<Cpd. 150>
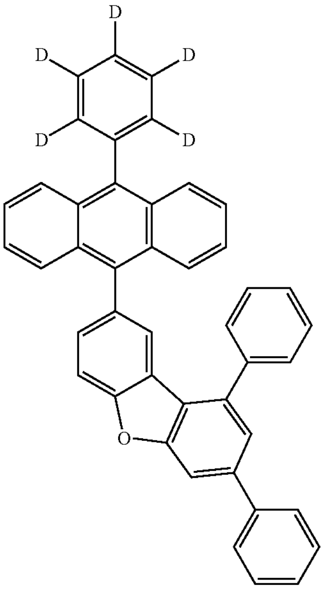
<Cpd. 151>
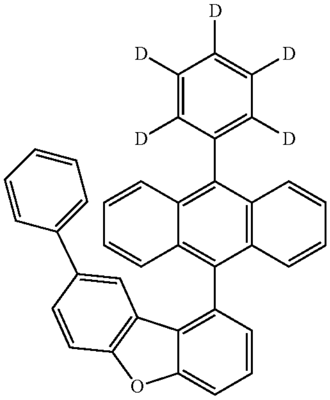
<Cpd. 152>
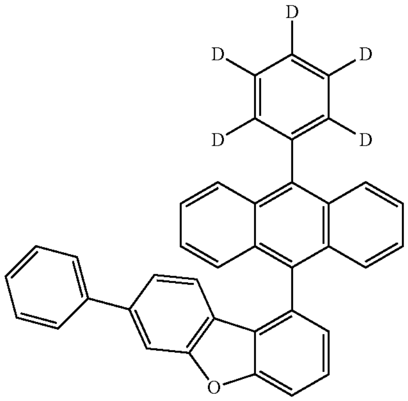
<Cpd. 153>
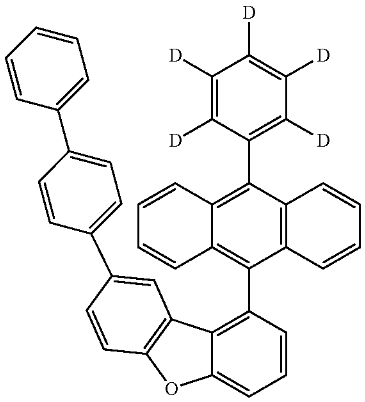
<Cpd. 154>
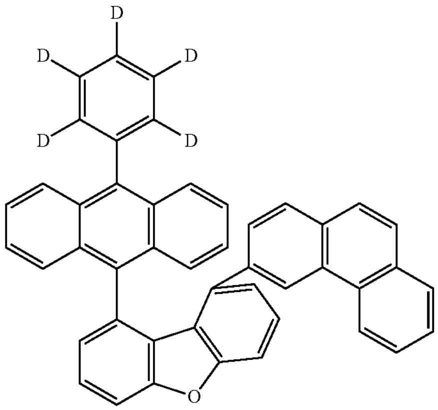

-continued

<Cpd. 155>

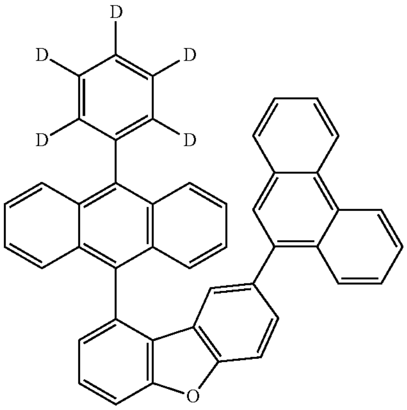

<Cpd. 156>

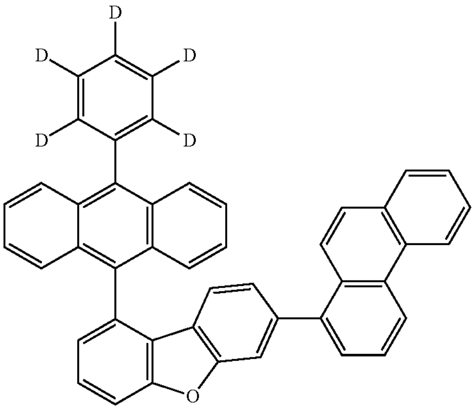

As represented by Chemical Formulas A to D, each of the compounds corresponding to the material for the electron-density-controlling layer is based on an anthracene skeleton having a substituted or unsubstituted arylene of 6 to 50 carbon atoms or a substituted or unsubstituted heteroarylene of 2 to 50 carbon atoms as a substituent at position 10, and a linker L as a substituent at position 9, the linker L being linked to the dibenzofuran ring of the following diagram 1 at position 1 or 2 of the dibenzofuran ring.

[Diagram 1]

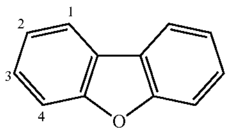

In some embodiments of the present disclosure, each of the substituents Ar1 and Ar2 in Chemical Formulas A to D may be a substituted or unsubstituted aryl of 6 to 18 carbon atoms, and each of the compounds represented by Chemical Formulas A to D and H may include a deuterium atom.

As illustrated in Chemical Formulas B and D, the dibenzofuran ring connected (through the linker L) to the anthracene moiety of the anthracene derivative according to the present disclosure forms a 5-membered ring with the structural formula Q1 or Q2. In Chemical Formula B, for example, the substituents R12 and R13, or two adjacent ones among the substituents R14 to R17 within the dibenzofuran ring moiety, may be respective single bonds for forming a 5-membered ring as a fused ring together with a carbon atom to which substituents R22 and R23 of Structural Formula Q1 are bonded. In Chemical Formula D, two adjacent ones among the substituents R41 to R43, or two adjacent ones among the substituents R44 to R47, within the dibenzofuran ring moiety may be respective single bonds for forming a 5-membered ring as a fused ring together with a carbon to which substituents R52 and R53 of Structural Formula Q2 are bonded. In both cases, two adjacent ones among the intracyclic carbon atoms that are not bonded with the linker L within the dibenzofuran ring may further form a fused ring.

According to some embodiments of the present disclosure, the substituents R22 and R23 of Structural Formula Q1 in Chemical Formula B may be the same or different, and are each independently a substituted or unsubstituted aryl of 6 to 24 carbon atoms, and the substituents R52 and R53 of Structural Formula Q2 in Chemical Formula D may be the same or different, and are each independently a substituted or unsubstituted aryl of 6 to 24 carbon atoms.

Meanwhile, the compound of Chemical Formula B or D may include an additional fused ring, because the substituents R22 and R23 of Structural Formula Q1 in Chemical Formula B may be connected to each other to form a ring or because the substituents R52 and R53 may be connected to each other to form a ring.

For instance, when the substituents R52 and R53 are connected to each other, the compound represented by Chemical Formula D may include a substituted or unsubstituted spirobifluorene ring as illustrated in the following Diagram 2. Likewise, the compound represented by Chemical Formula B may include a substituted or unsubstituted spirobifluorene ring when the substituents R22 and R23 are connected to each other.

[Diagram 2]

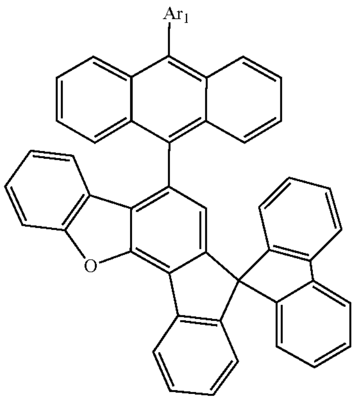

The compound, represented by one of Chemical Formulas A to D, available for the electron-density-controlling layer, may be selected from among Compounds 201 to 304, but is not limited thereto.

<Cpd. 201>
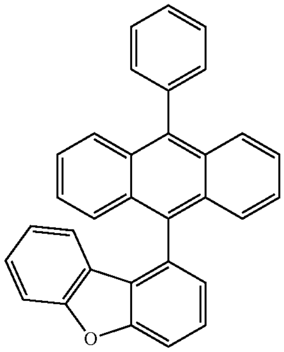
<Cpd. 202>
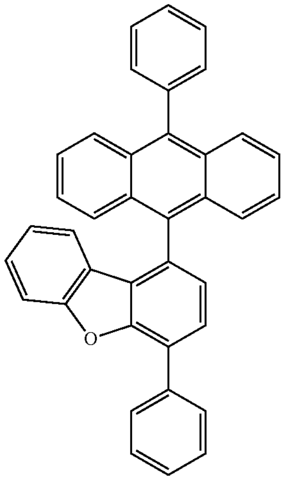
<Cpd. 203>
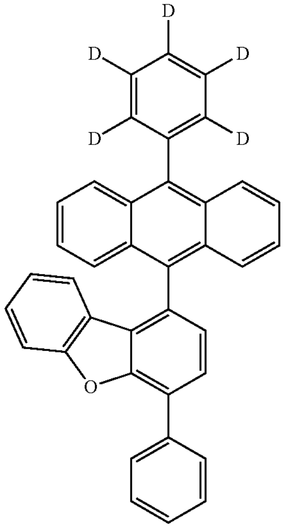
-continued
<Cpd. 204>
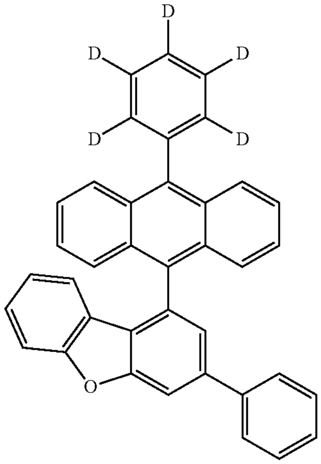
<Cpd. 205>
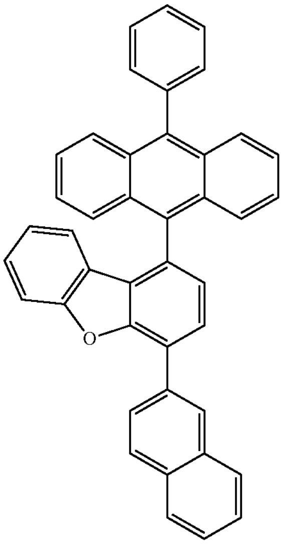
<Cpd. 206>
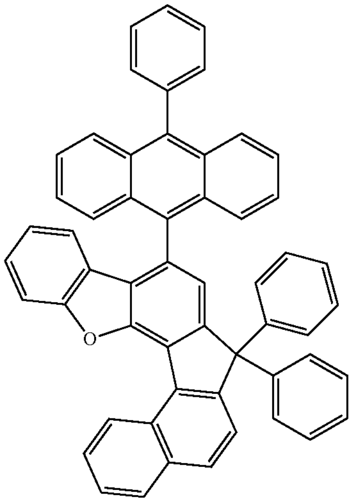

-continued
<Cpd. 207>
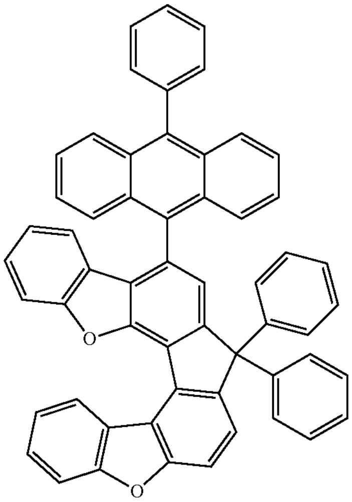
<Cpd. 208>
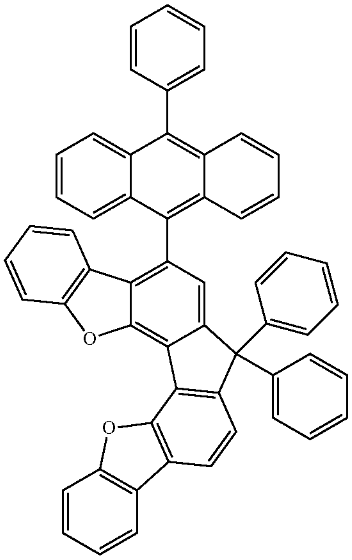
<Cpd. 209>
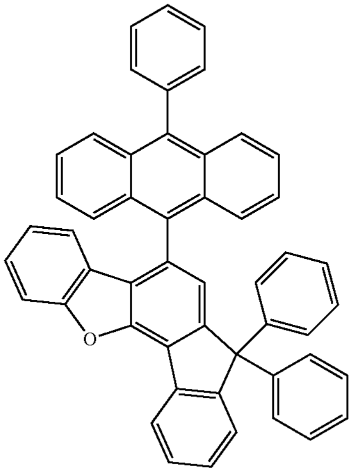
-continued
<Cpd. 210>
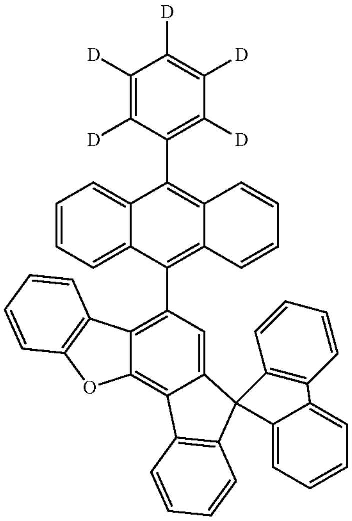
<Cpd. 211>
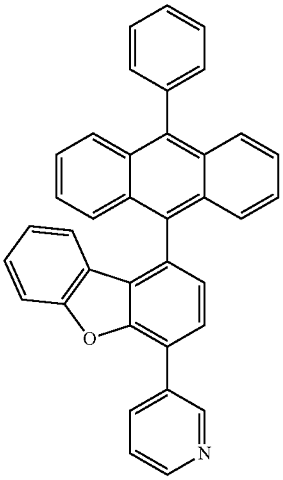
<Cpd. 212>
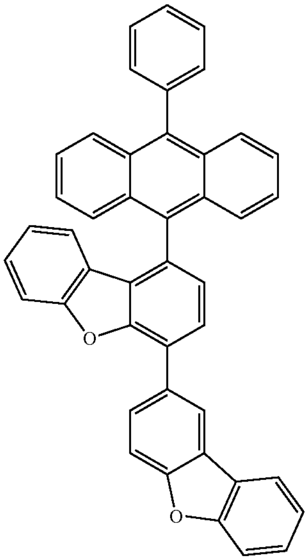

-continued
<Cpd. 213>
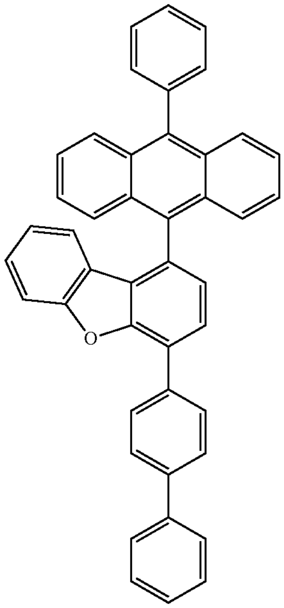
<Cpd. 214>
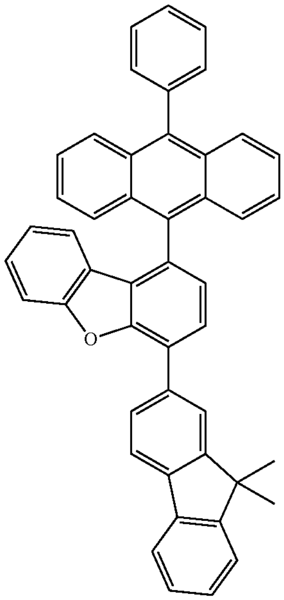
-continued
<Cpd. 215>
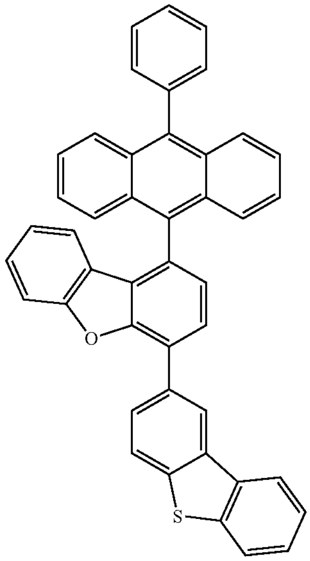
<Cpd. 216>
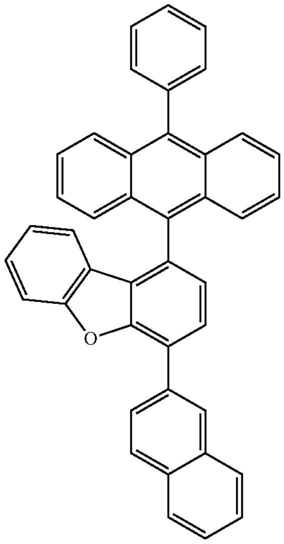
<Cpd. 217>
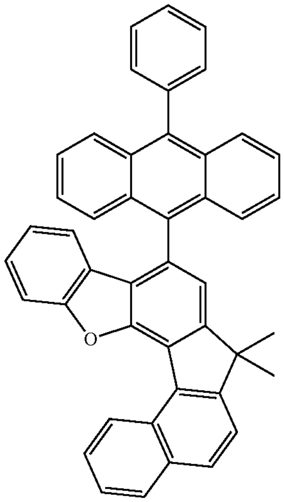

-continued
<Cpd. 218>
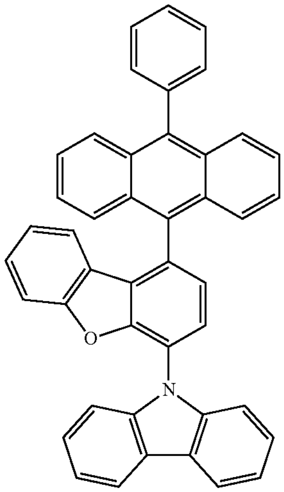
<Cpd. 219>
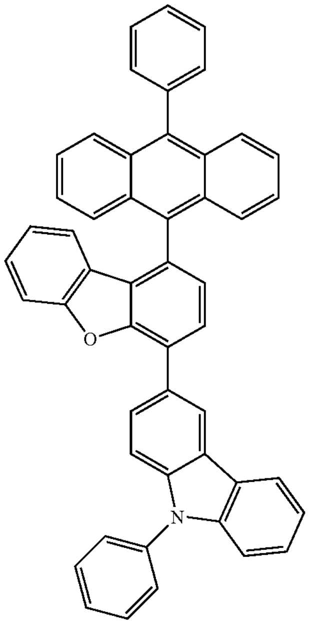
<Cpd. 220>
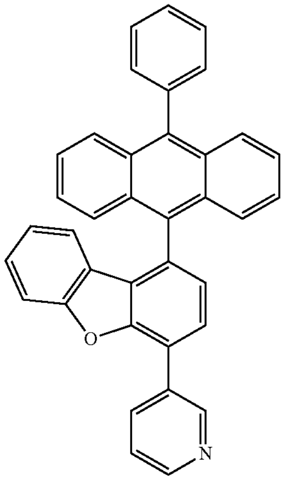
-continued
<Cpd. 221>
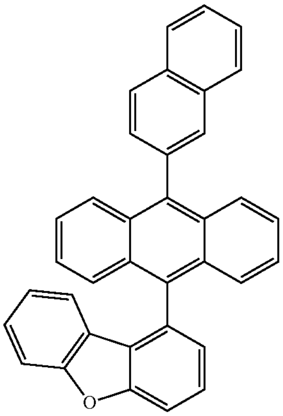
<Cpd. 222>
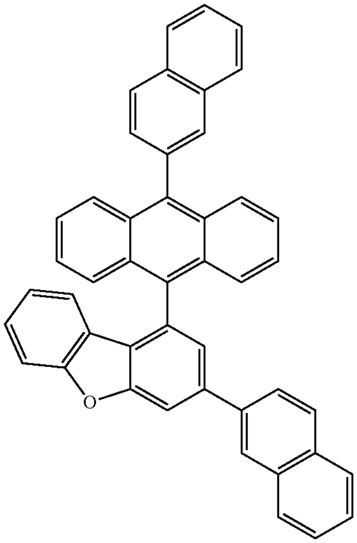
<Cpd. 223>
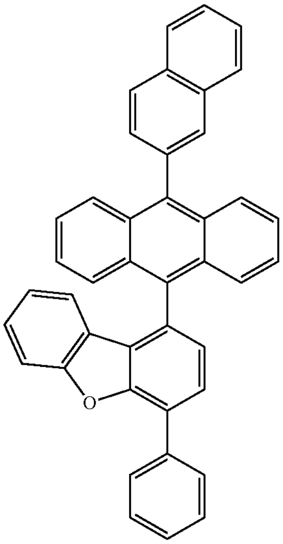

-continued
(Cpd. 224>
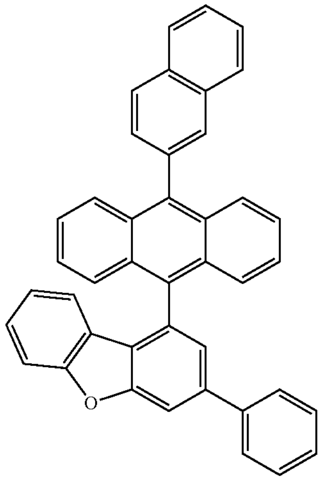
<Cpd. 225>
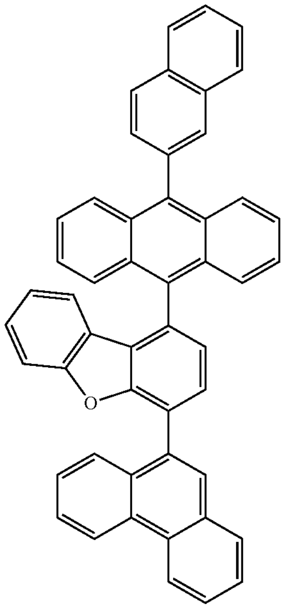
<Cpd. 226>
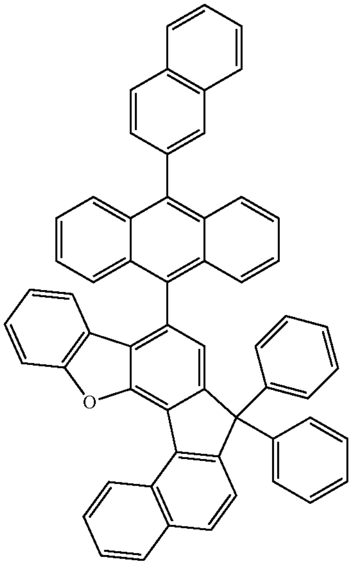
-continued
(Cpd. 227>
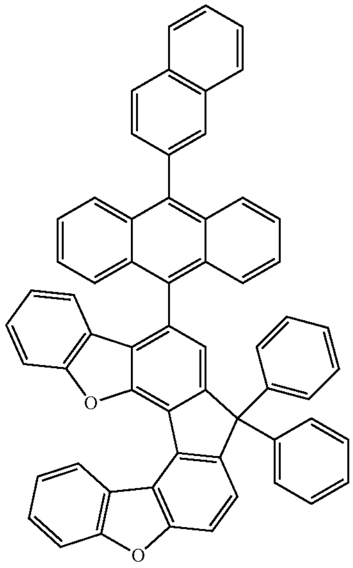
<Cpd. 228>
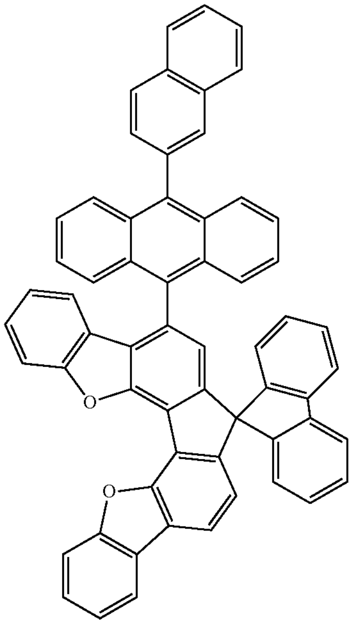

-continued
<Cpd. 229>
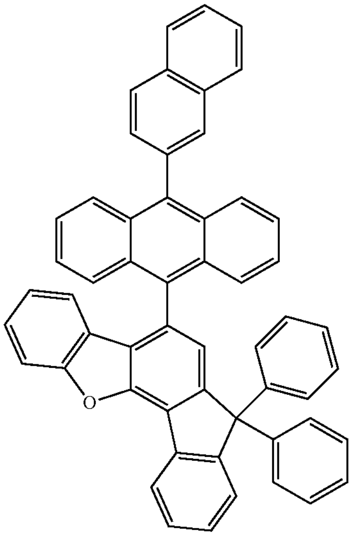
<Cpd. 230>
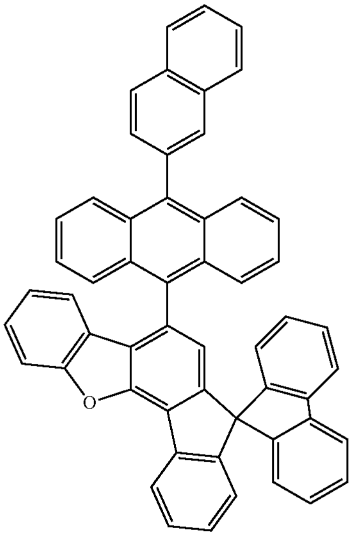
<Cpd. 231>
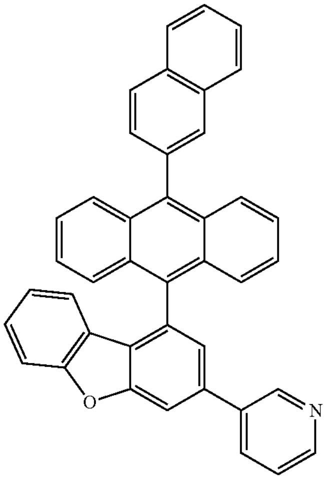
-continued
<Cpd. 232>
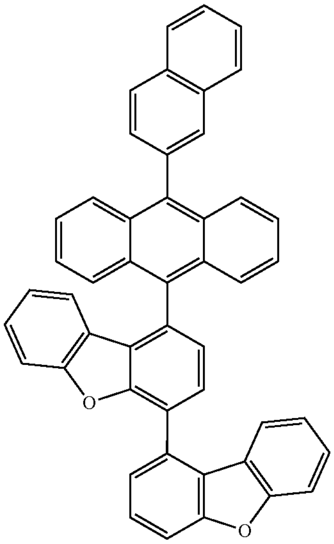
<Cpd. 233>
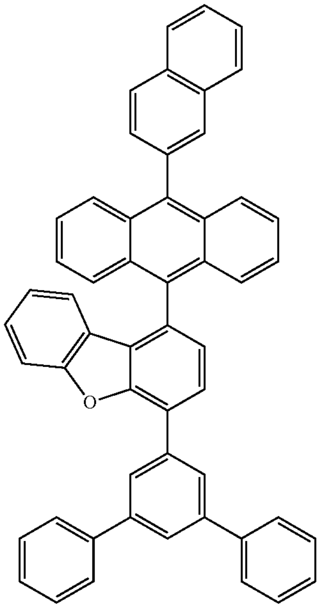

-continued
<Cpd. 234>
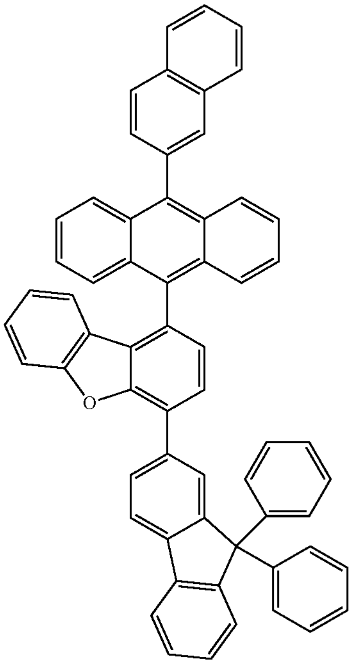
<Cpd. 235>
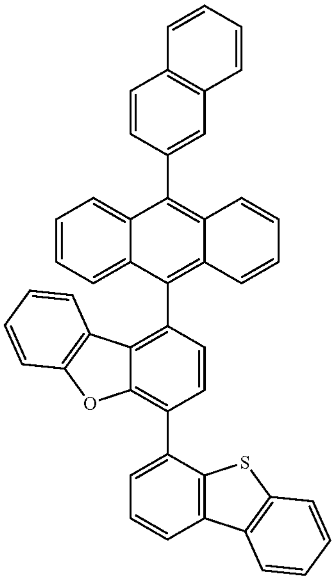
-continued
<Cpd. 236>
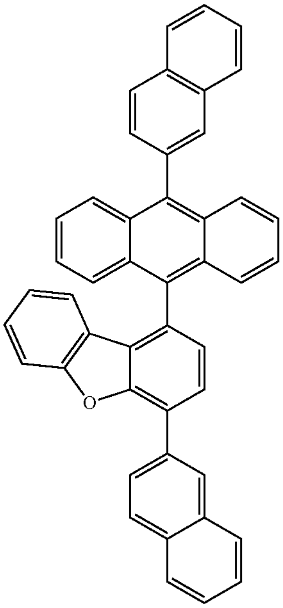
<Cpd. 237>
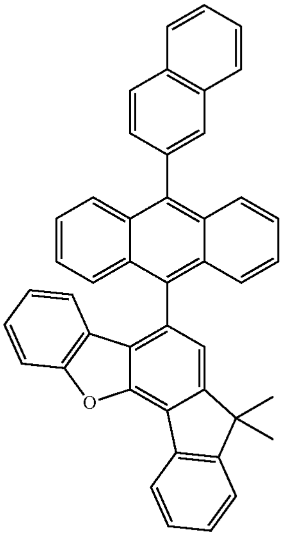

-continued
<Cpd. 238>
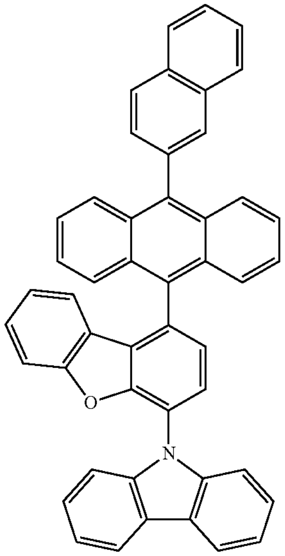
<Cpd. 239>
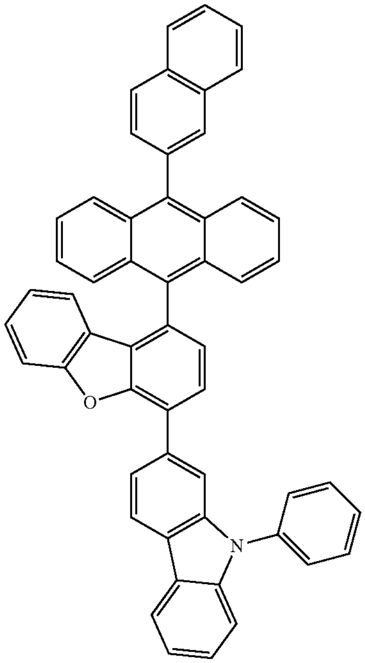
-continued
<Cpd. 240>
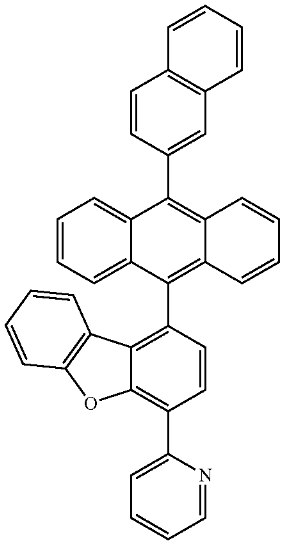
<Cpd. 241>
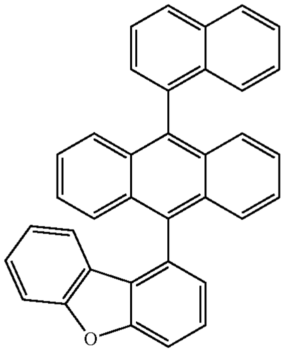
<Cpd. 242>
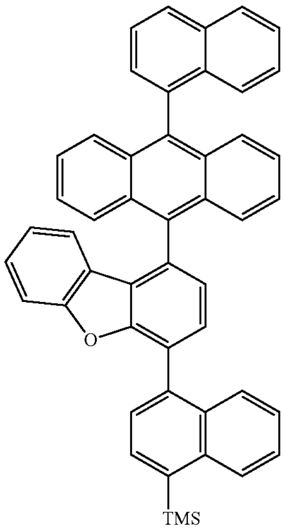

-continued
<Cpd. 243>
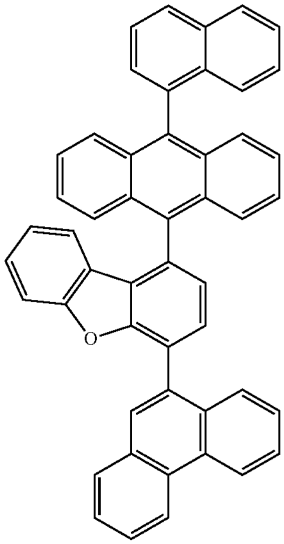
<Cpd. 244>
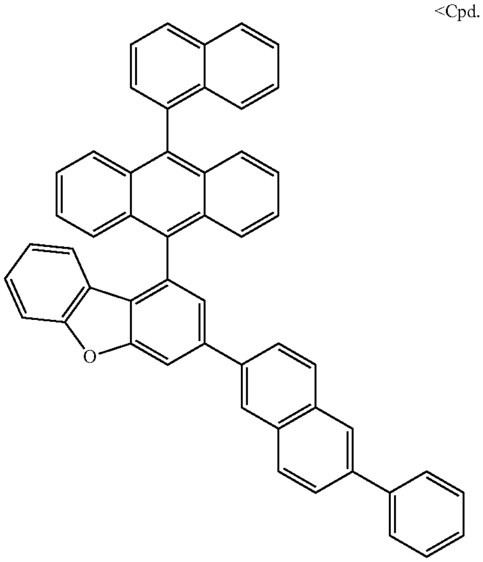
<Cpd. 245>
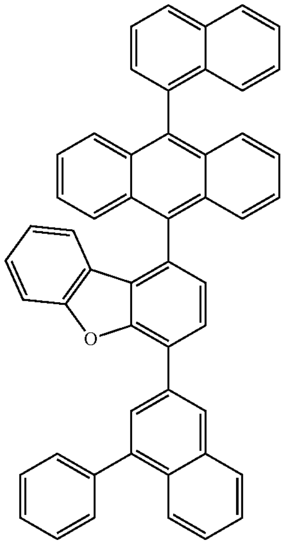
-continued
<Cpd. 246>
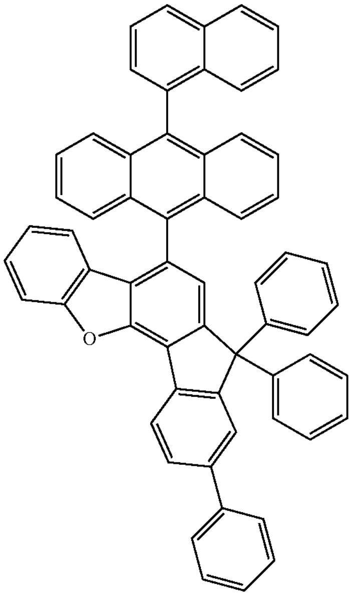
<Cpd. 247>
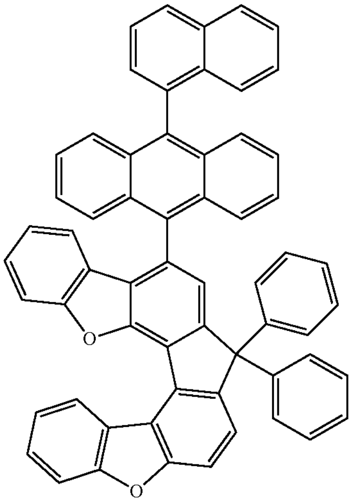
<Cpd. 248>
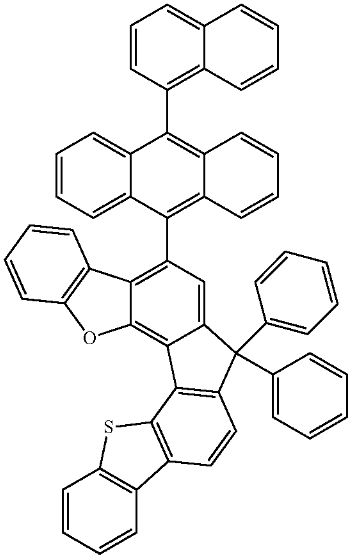

-continued
<Cpd. 249>
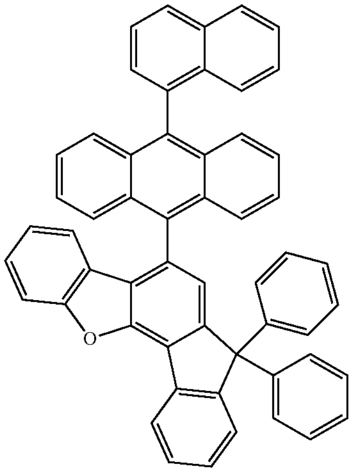
<Cpd. 250>
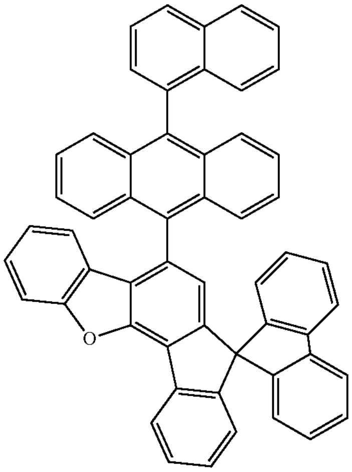
<Cpd. 251>
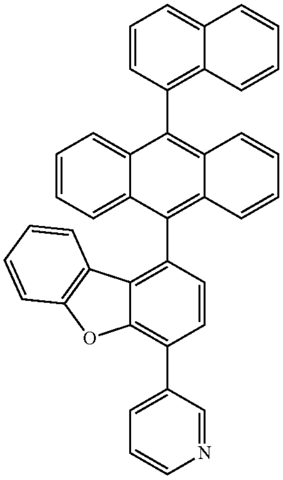
-continued
<Cpd.252>
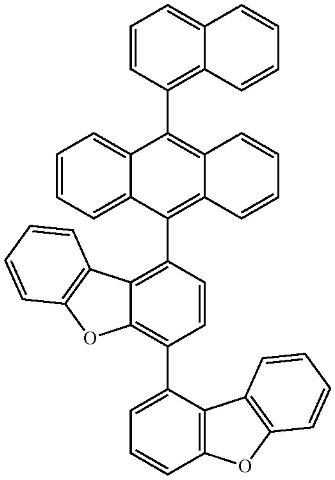
<Cpd. 253>
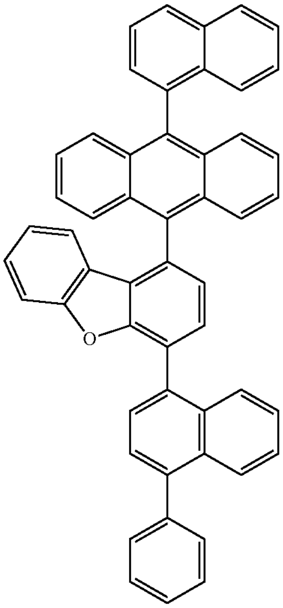

-continued
<Cpb.254>
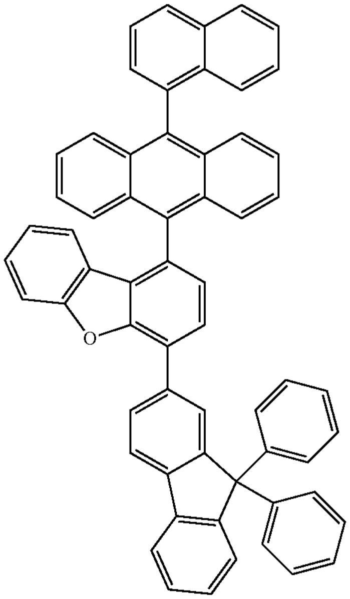
<Cpd. 255>
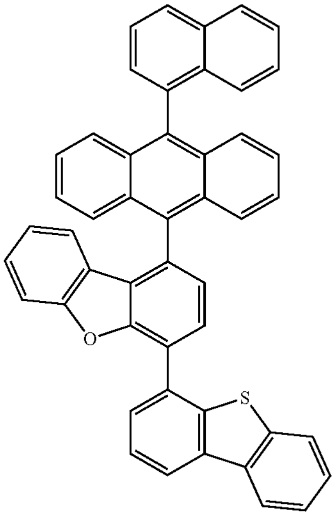
<Cpd. 256>
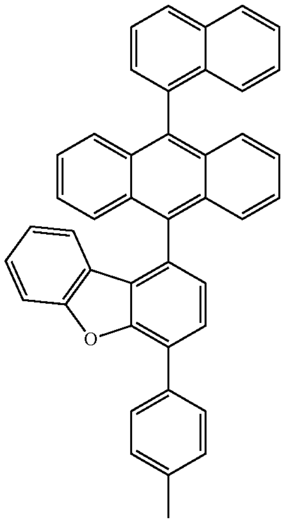
-continued
<Cpd. 257>
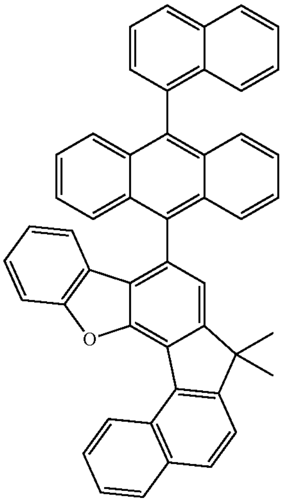
<Cpd. 258>
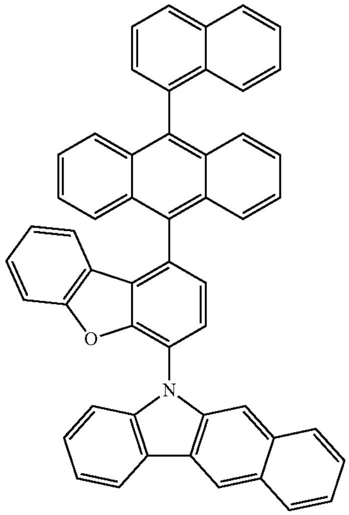
<Cpd. 259>
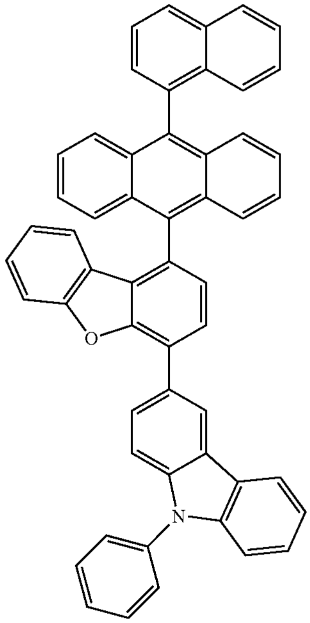

-continued
<Cpd. 260>
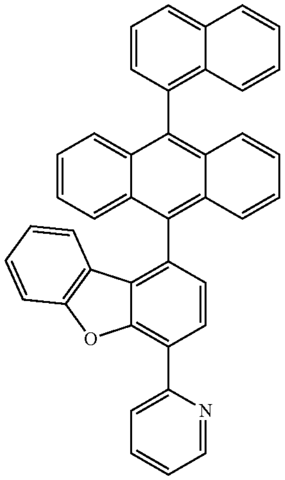
<Cpd. 261>
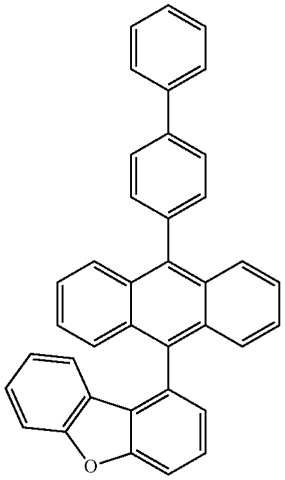
<Cpd. 262>
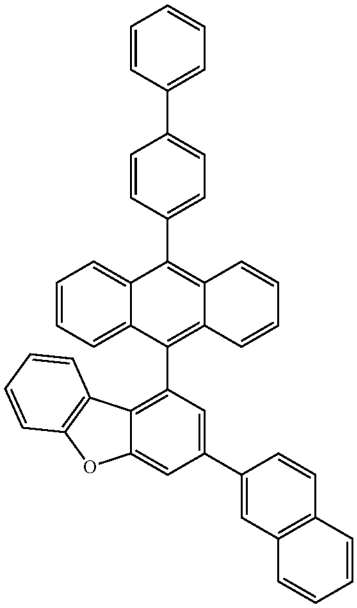
-continued
<Cpd. 263>
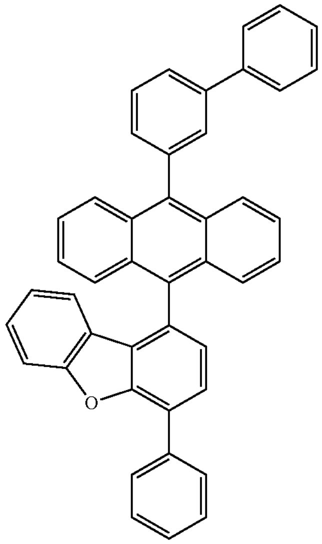
<Cpd. 264>
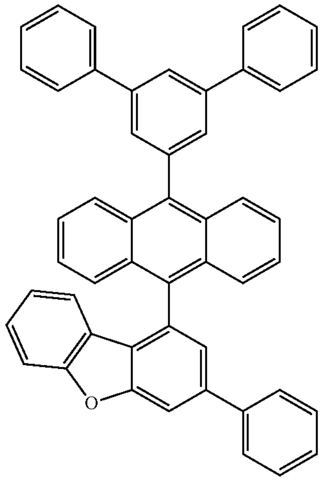
<Cpd. 265>
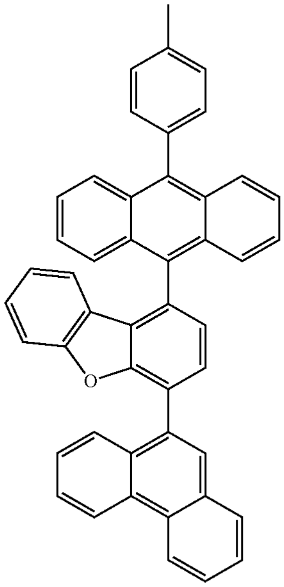

-continued
<Cpd. 266>
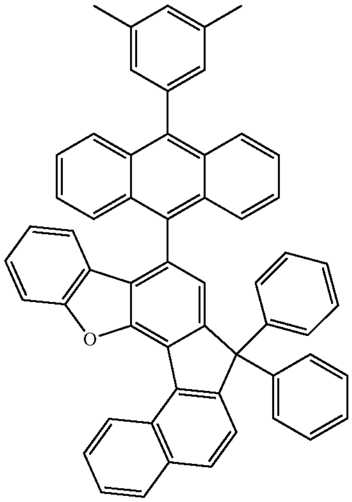
<Cpd. 267>
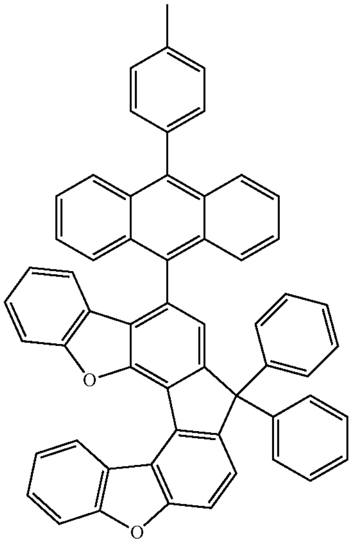
<Cpd. 268>
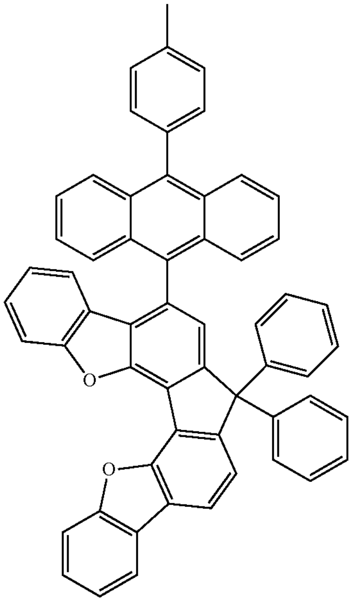
-continued
<Cpd. 269>
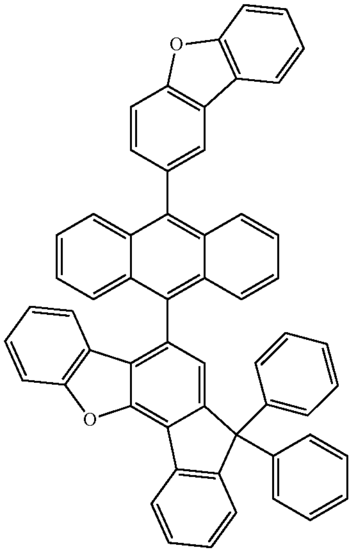
<Cpd. 270>
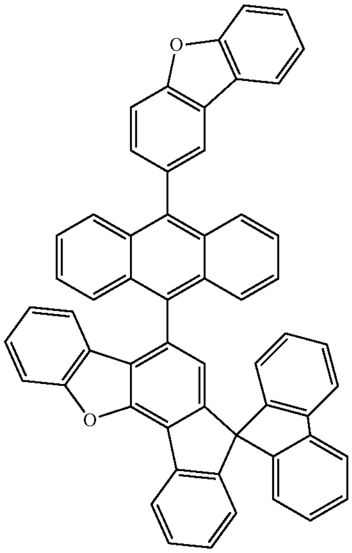
<Cpd. 271>
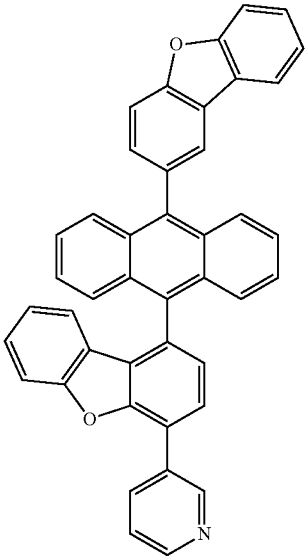

-continued
<Cpd. 272>
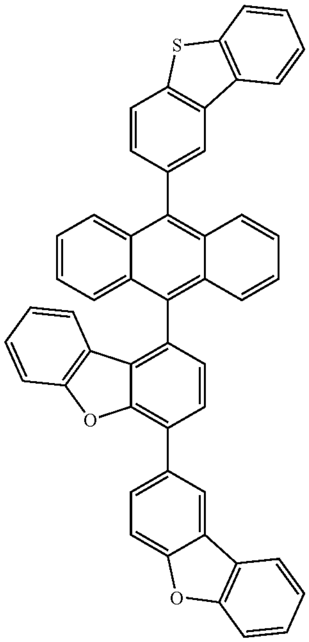
<Cpd. 273>
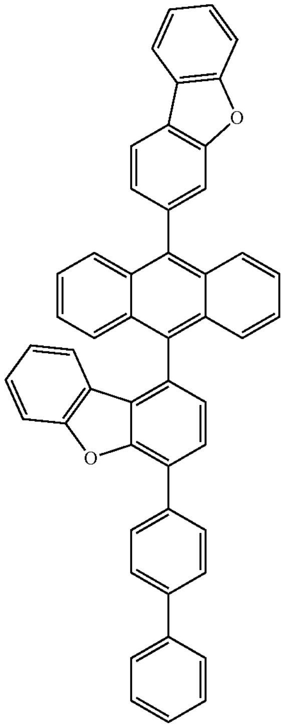
-continued
<Cpd. 274>
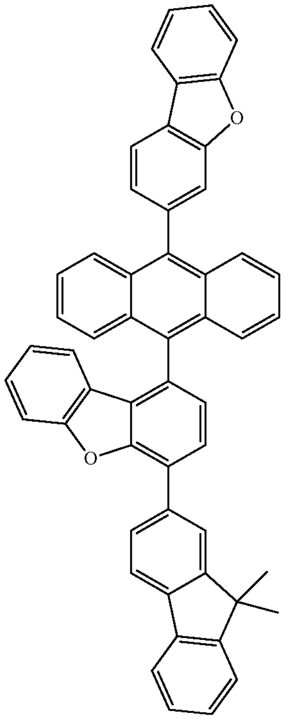
<Cpd. 275>
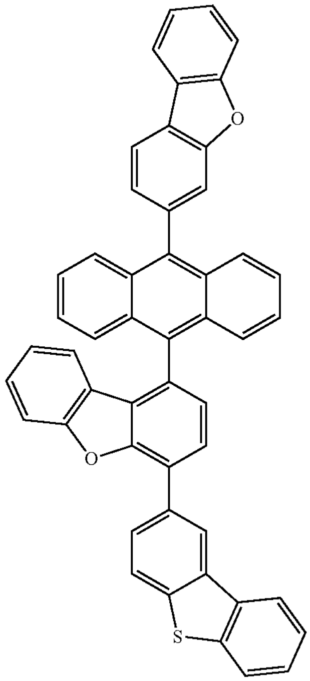

-continued
<Cpd. 276>
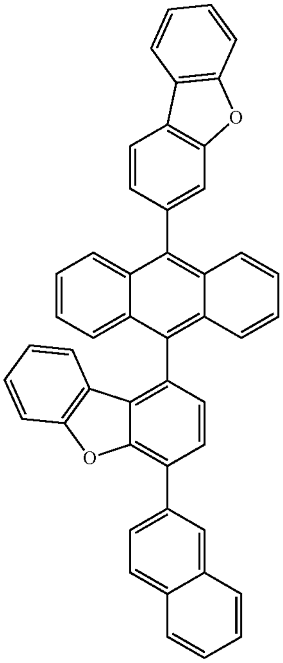
<Cpd. 277>
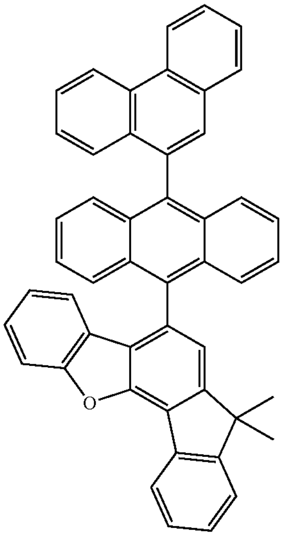
-continued
<Cpd. 278>
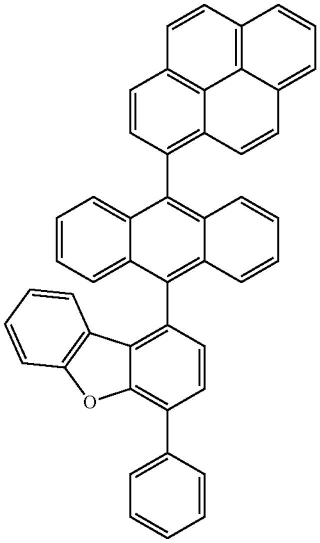
<Cpd. 279>
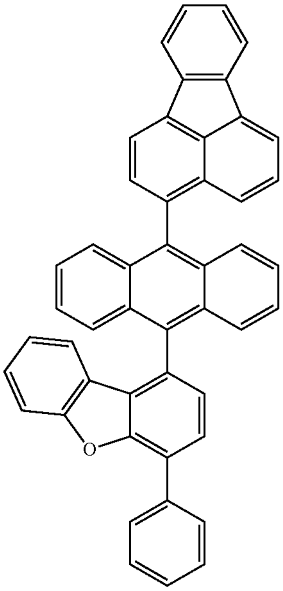
<Cpd. 280>
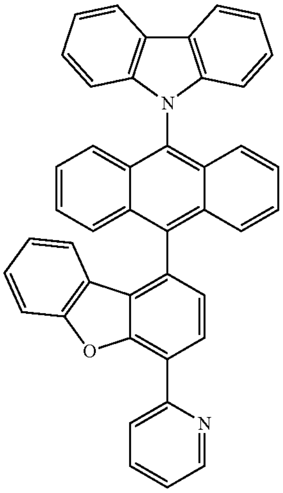

-continued
<Cpd. 281>
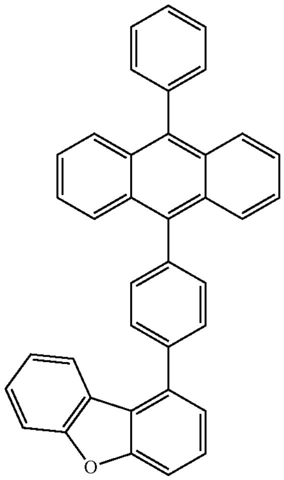
<Cpd. 282>
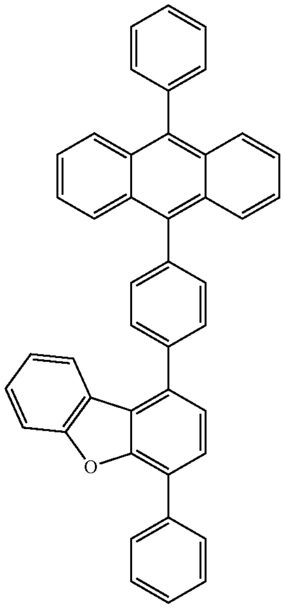
-continued
<Cpd. 283>
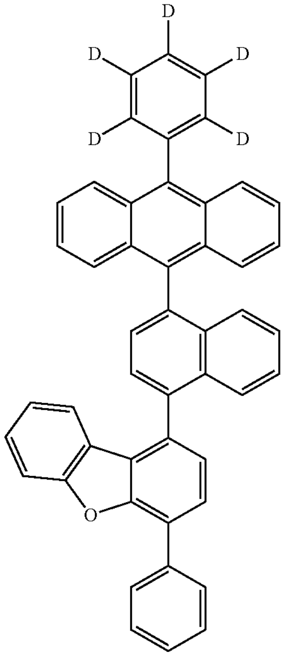
<Cpd. 284>
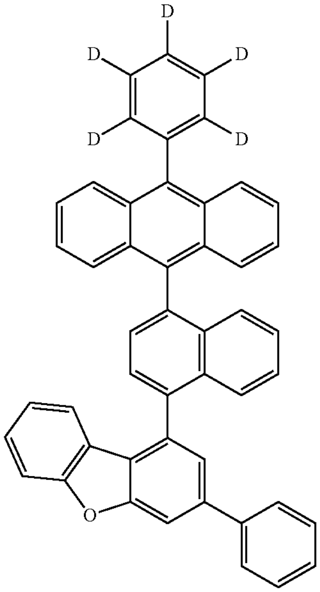

-continued
<Cpd. 285>
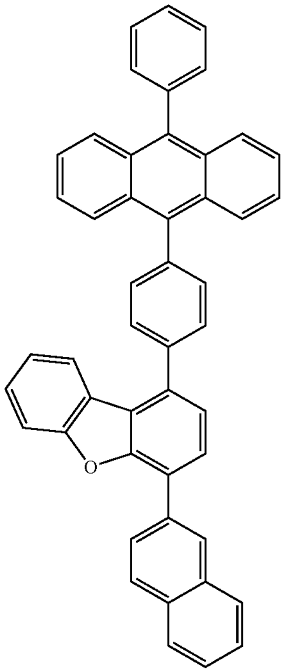
<Cpd. 286>
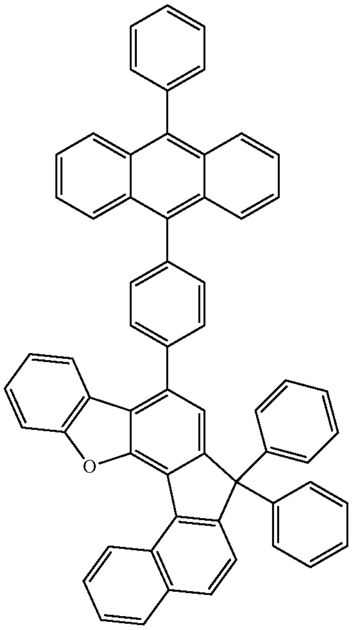
-continued
<Cpd. 287>
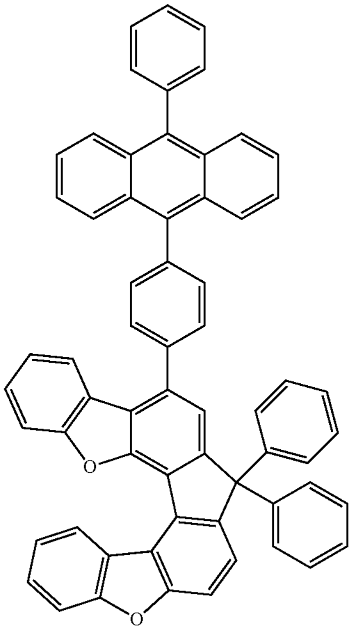
<Cpd. 288>
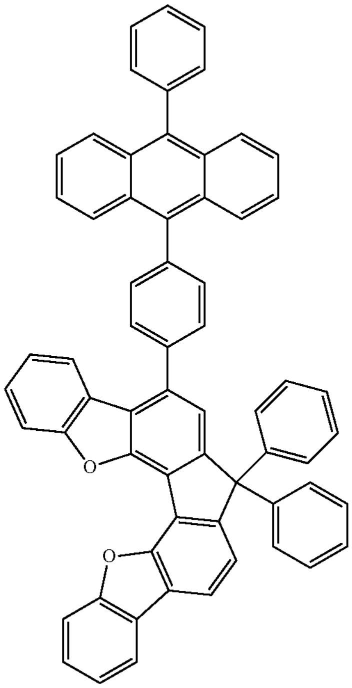

-continued
<Cpd. 289>
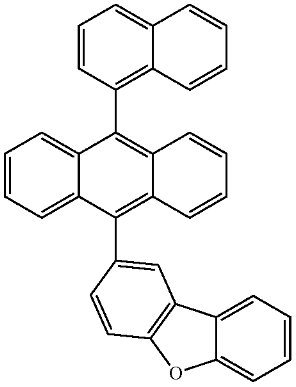
<Cpd. 290>
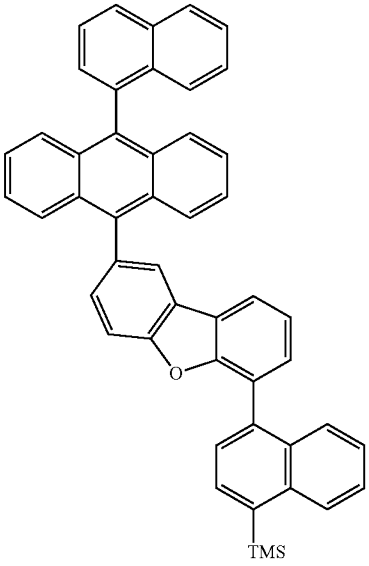
<Cpd. 291>
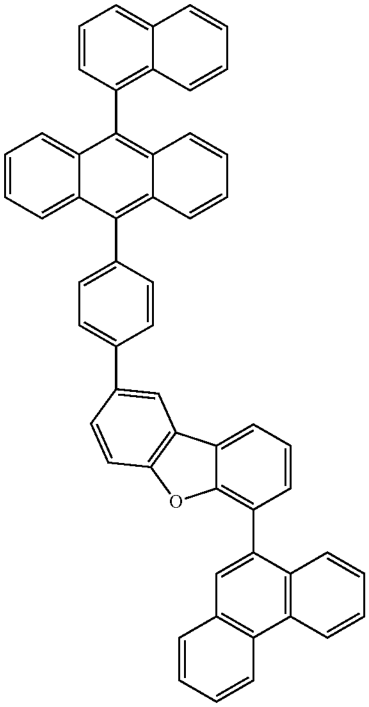
-continued
<Cpd. 292>
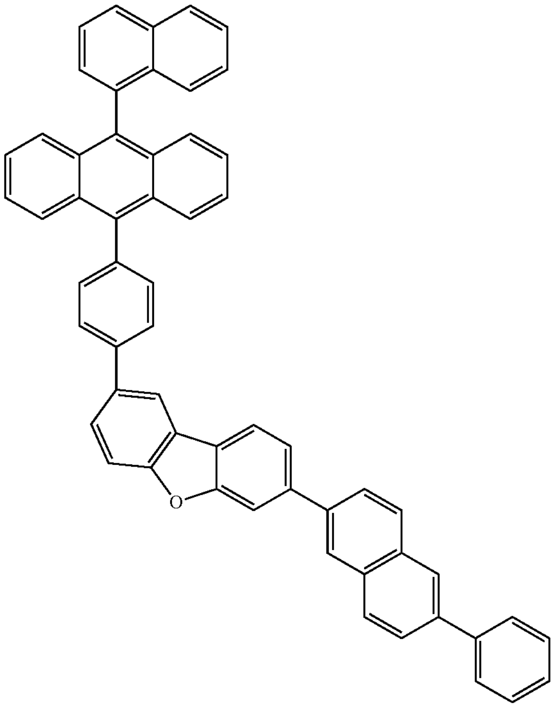
<Cpd. 293>
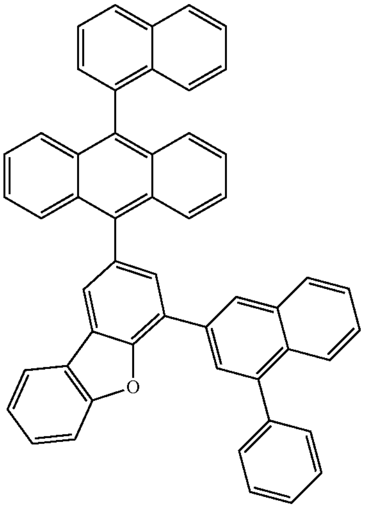

-continued
<Cpd. 294>
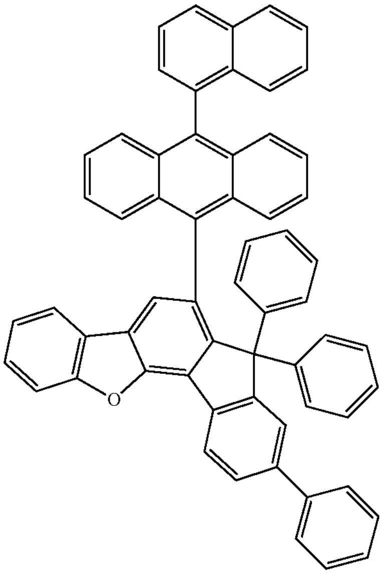
<Cpd. 295>
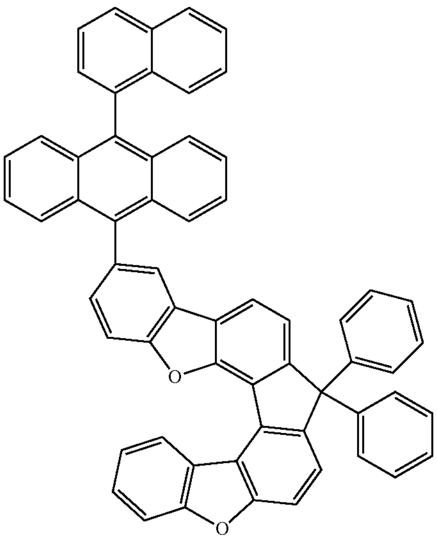
-continued
<Cpd. 296>
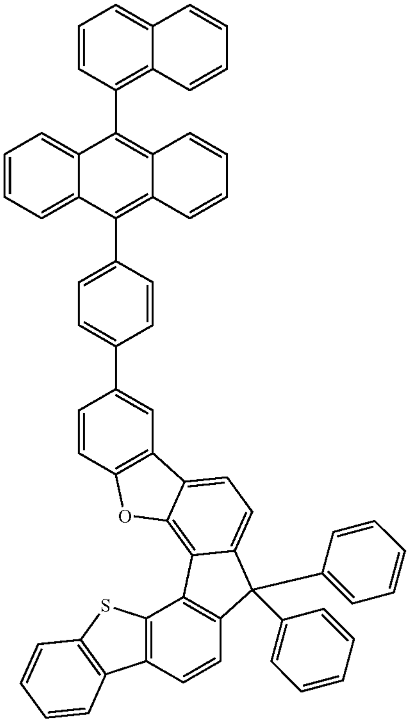
<Cpd. 297>
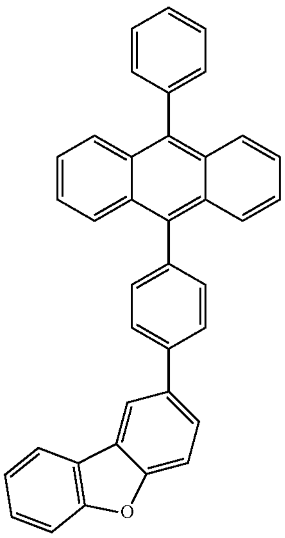

-continued
<Cpd. 298>
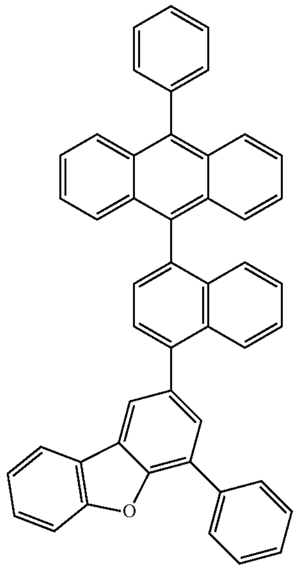
<Cpd. 299>
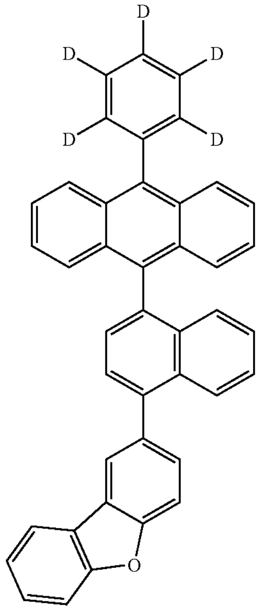
-continued
<Cpd. 300>
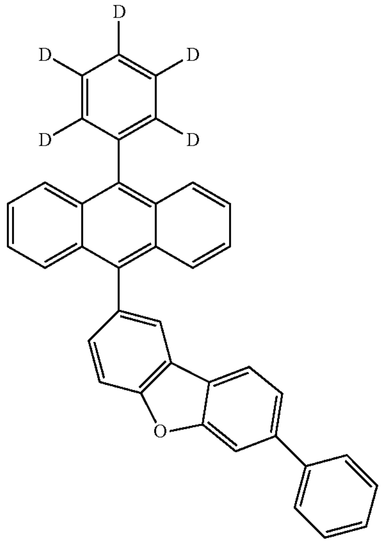
<Cpd. 301>
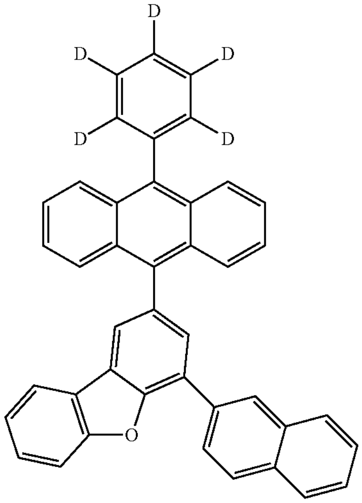

-continued

<Cpd. 302>

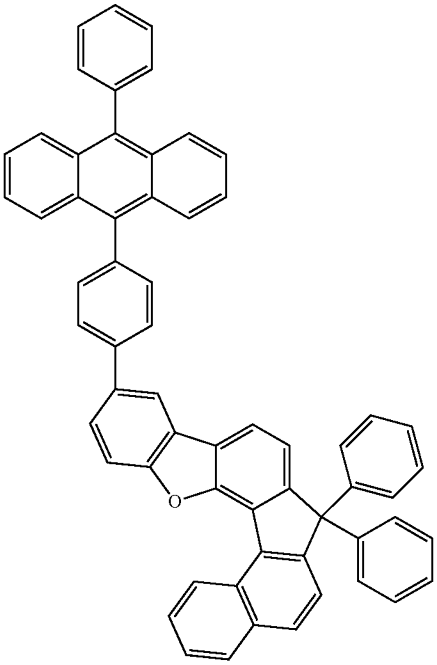

<Cpd. 303>

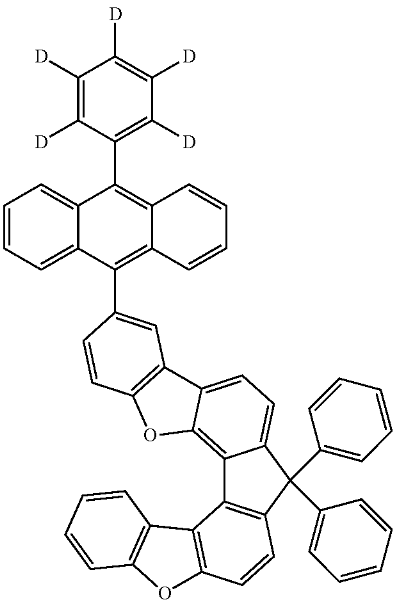

-continued

<Cpd. 304>

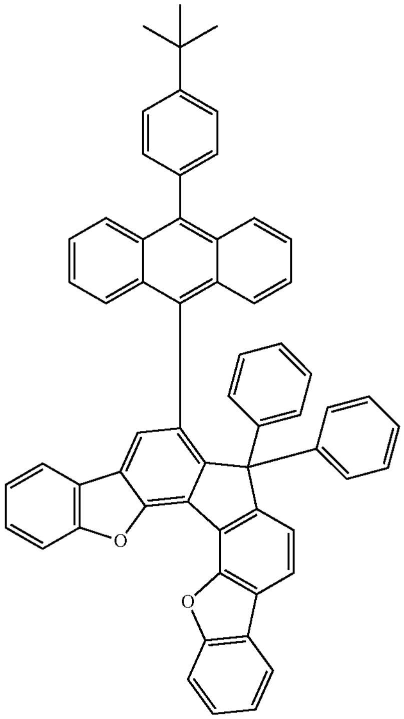

Moreover, the anthracene compound, represented by Chemical Formula H, useful for the light-emitting layer, may be identical to the compound represented by one of Chemical Formulas A to D, useful for the electron-density-controlling layer.

In the organic light-emitting diode of the present disclosure, the first electrode is an anode and the second electrode is a cathode, with the interposition of a hole transport layer between the cathode and the light-emitting layer and an electron transport layer between the electron-density-controlling layer and the anode.

In addition, the dopant useful in the light-emitting layer may include at least one selected from among compounds represented by the following Chemical Formulas I to K:

[Chemical Formula I]

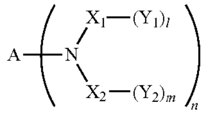

[Chemical Formula J]

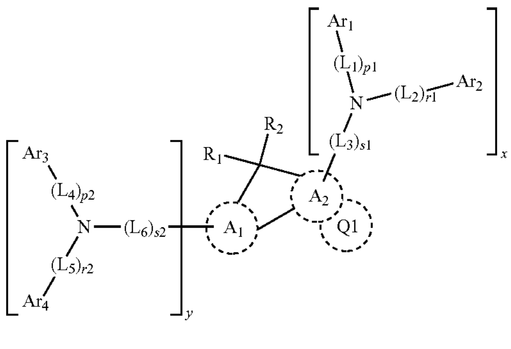

-continued $Q_1$:

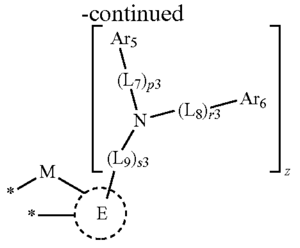

[Chemical Formula K]

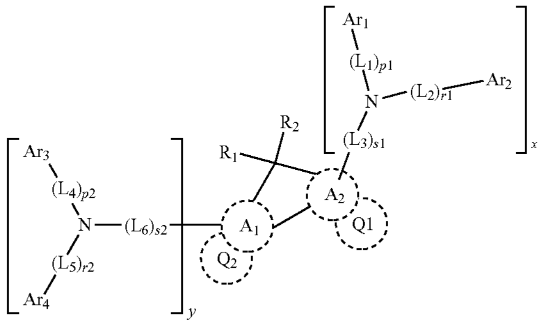

$Q_1$:

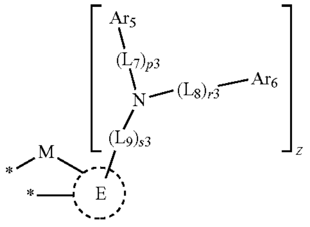

$Q_2$:

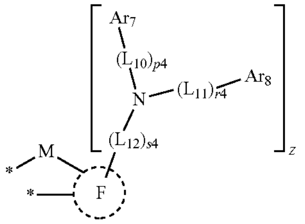

In Chemical Formula I, A is selected from the group consisting of a substituted or unsubstituted aryl of 5 to 50 carbon atoms, a substituted or unsubstituted heteroaryl of 3 to 50 carbon atoms containing at least one heteroatom selected from among O, N and S, a substituted or unsubstituted arylene of 6 to 60 carbon atoms, and a substituted or unsubstituted heteroarylene of 3 to 50 carbon atoms containing at least one heteroatom selected from among O, N and S.

According to some particular embodiments, the moiety A may be anthracene, pyrene, phenanthrene, indenophenanthrene, chrysene, naphthacene, picene, triphenylene, perylene, or pentacene.

In Chemical Formula I,

X1 and X2, which may the same or different, are each independently selected from among a substituted or unsubstituted arylene of 6 to 30 carbon atoms and a single bond, and may be bonded to each other;

Y1 and Y2, which may be the same or different, are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, cyano, halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, germanium, phosphorus, boron, deuterium, and hydrogen, wherein adjacent substituents on Y1 and Y2 may form a fused, aliphatic, aromatic, heteroaliphatic or heteroaromatic ring; and l and m are each an integer of 1 to 20, and n is an integer of 1 to 4.

In Chemical Formulas J and K,

A1, A2, E, and F may be the same or different, and are each independently a substituted or unsubstituted aromatic hydrocarbon of 6 to 50 carbon atoms or a substituted or unsubstituted heteroaromatic ring of 2 to 40 carbon atoms, wherein two adjacent carbon atoms of the aromatic ring A1 and two adjacent carbon atoms of the aromatic ring A2 form a 5-membered fused ring together with a carbon atom to which substituents R1 and R2 are bonded;

linkers L1 to L12 may be the same or different, and are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—R3, CR4R5, SiR6R7, GeR8R9, O, S, and Se;

R1 to R9, and Ar1 to Ar8 may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 5 to 30 carbon atoms, a substituted or unsubstituted alkyl amine of 1 to 30 carbon atoms, a substituted or unsubstituted aryl amine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, with the proviso that R1 and R2 together may form a mono- or polycyclic aliphatic or aromatic ring, which may be a heterocyclic ring having a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers L1 to L12 may be the same or different;

x is an integer of 1 or 2, and y and z may be the same or different and are each independently an integer of 0 to 3; and Ar1 may form a ring with Ar2, Ar3 may form a ring with Ar4, Ar5 may form a ring with Ar6, and Ar7 may form a ring with Ar8.

In Chemical Formula J, two adjacent carbon atoms of the A2 ring occupy respective positions * of Structural Formula Q1 to form a fused ring.

In Chemical Formula K, two adjacent carbon atoms of the A1 ring occupy respective positions * of Structural Formula Q2 to form a fused ring, and two adjacent carbon atoms of the A2 ring occupy respective positions * of Structural Formula Q1 to form a fused ring.

The light-emitting layer may include various hosts and dopants in addition to the above-described dopant and host.

Hereinafter, an organic light-emitting diode according to some embodiments of the present invention will be described with reference to the drawings.

FIG. 1 is a diagram of the structure of an organic light-emitting diode according to some embodiments of the present disclosure.

As can be seen in FIG. 1, the light-emitting diode according to some embodiments of the present disclosure comprises an anode 20, a hole transport layer 40, a light-emitting layer 50 including a host and a dopant, an electron transport layer 60, and a cathode 80 in that order, wherein an electron-density-controlling layer including at least one selected from among compounds represented by the following Chemical Formulas A to D is interposed between the light-emitting layer and the electron transport layer, and the light-emitting layer includes at least one anthracene compound represented by the following Chemical Formula H.

Reference is made to FIG. 1 with regard to the structure and fabrication of the organic light-emitting diode of the present disclosure. First, a substrate 10 is coated with an anode electrode material to form an anode 20. So long as it is used in a typical organic EL device, any substrate may be used as the substrate 10. Preferable is an organic substrate or a transparent plastic substrate that exhibits excellent transparency, surface smoothness, and ease of handling. As the anode electrode material, indium tin oxide (ITO), indium zinc oxide (IZO), tin oxide ($SnO2$), or zinc oxide (ZnO) may be used because of the high transparency and conductivity thereof.

A hole injection layer material is applied on the anode electrode 20 by thermal deposition in a vacuum or by spin coating to form a hole injection layer 30. Subsequently, thermal deposition in a vacuum or spin coating may also be conducted so as to deposit a hole transport layer material on the hole injection layer 30, resulting in the formation of a hole transport layer 40.

No particular limitations are imposed on the hole injection layer material, as long as it is typically used in the art. For example, mention may be made of 2-TNATA [4,4',4"-tris(2-naphthylphenyl-phenylamino)-triphenylamine], NPD[N,N'-di(1-naphthyl)-N,N'-diphenylbenzidine)], TPD[N,N'-diphenyl-N,N'-bis(3-methylphenyl)-1,1'-biphenyl-4,4'-diamine], and DNTPD[N,N'-diphenyl-N,N'-bis-[4-(phenyl-m-tolyl-amino)-phenyl]-biphenyl-4,4'-diamine], but the invention is not limited thereto.

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

Then, a light-emitting layer 50 is deposited on the hole transport layer 40 by vacuum deposition or spin coating, followed by the formation of a thin electron-density-controlling layer 55 on the organic light-emitting layer 50 by vacuum deposition or spin coating.

In some embodiments of the present disclosure, the light-emitting layer may comprise a host and a dopant.

In some embodiments of the present disclosure, the light-emitting layer particularly ranges in thickness from 50 to 2,000 Å.

Together with a dopant, a host material may be employed in the light-emitting layer. When the light-emitting layer comprises a host and a dopant, the content of the dopant may range from about 0.01 to 20 parts by weight based on 100 parts by weight of the host, but is not limited thereto.

Meanwhile, after being formed on the light-emitting layer, an electron-density-controlling layer 55 is covered with an electron transport layer 60 by vacuum deposition or spin coating and then with an electron injection layer 70. A cathode metal is deposited on the electron injection layer 70 by thermal vacuum deposition to form a cathode 80, thus obtaining an organic EL diode.

In accordance with some embodiments of the present disclosure, the affinity Ah (eV) of the host of the light-emitting layer, the affinity Aed (eV) of the electron-density-controlling layer, and the affinity Ae (eV) of the electron transport layer satisfy the relationship $Ah \geq Aed \geq Ae$.

Figure 2:
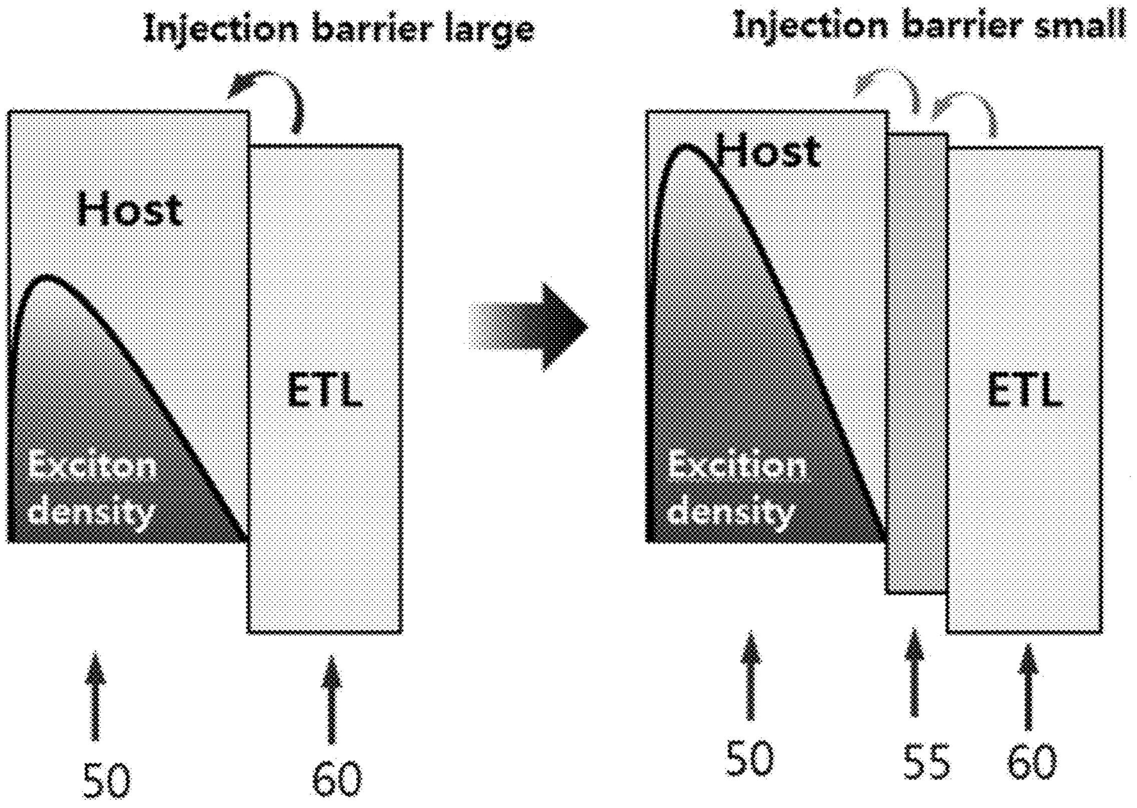
FIG. 2 shows the structures of light-emitting diodes in which an electron-density-controlling layer is absent or present in accordance with some embodiments of the present disclosure.

This can be elucidated in greater detail with reference to FIG. 2. FIG. 2 shows the structure of a light-emitting diode in which an electron-density-controlling layer is absent (left panel) or present (right panel).

As shown in the left panel of FIG. 2, when the electron transport layer 60 is in direct contact with the light-emitting layer 50, the electrons injected from the cathode are less prone to move through the electron transport layer 60 to the host 50 because there is a large electron injection barrier between the cathode and the host 50, resulting in low exciton density in the host of the light-emitting layer. In contrast, as in the present disclosure, when an affinity Aed (eV) of the electron-density-controlling layer is set to be between an affinity Ah (eV) of the host in the light-emitting layer and an affinity Ae (eV) of the electron transport layer ($Ah \geq Aed \geq Ae$), smaller interlayer electron injection barriers exist, resulting in greater exciton density in the host of the light-emitting layer.

Structured to have an electron-density-controlling layer for lowering the barrier to electron injection between a light-emitting layer and an electron transport layer, thus, the organic light-emitting diode of the present disclosure allows for the effective injection of electrons into the light-emitting layer so that it can increase the electron density of the light-emitting layer and the density of excitons generated in the light-emitting layer, resulting in an improvement in external quantum efficiency (EQE).

Figure 3:
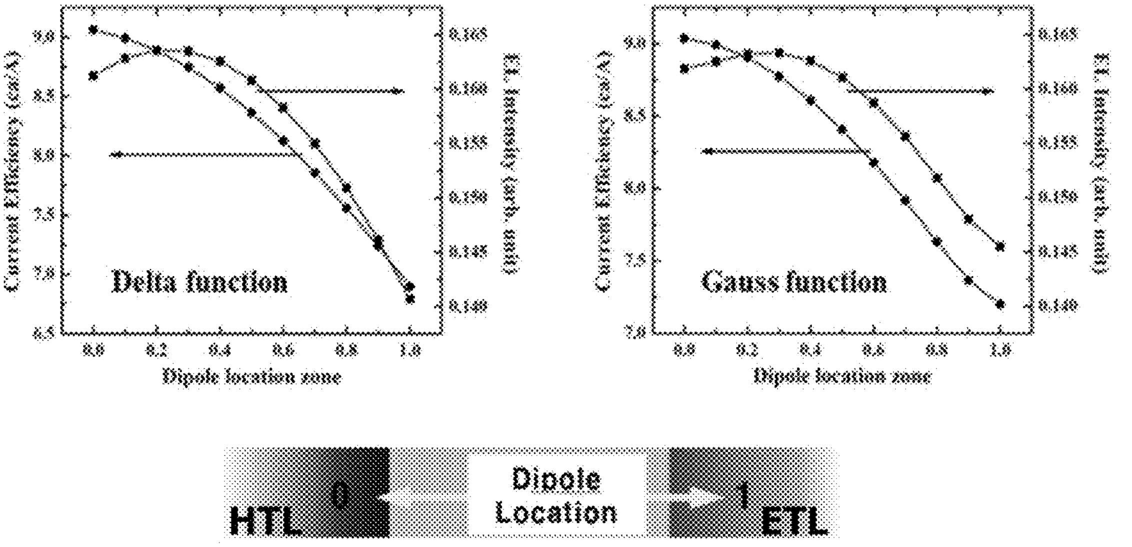
FIG. 3 shows the results of simulation of changes in current efficiency (left) and EL intensity (right) against dipole location zones of excitons in the light-emitting layer of the organic light-emitting diode according to the present disclosure.

A further explanation may be made with reference to FIG. 3. FIG. 3 shows the simulation results of changes in current efficiency (left) and EL intensity (right) against dipole location zones of excitons in the light-emitting layer of the organic lighting emitting diode according to the present disclosure.

In FIG. 3, the X-axis for the dipole location zone within the light-emitting layer in which excitons recombine is divided from 0 (zero) for the side of the hole transport layer to 1 for the side of the electron transport layer. As can be seen, higher current efficiency and EL intensities are detected at positions of excitons nearer to the hole transport layer.

Similar patterns are drawn whether the current efficiency and the EL intensity follow a delta function or a Gaussian function, as can be seen in FIG. 3.

That is, given the condition that the affinity Aed (eV) of the electron-density-controlling layer is between the affinity Ah (eV) of the host of the light-emitting layer and the affinity Ae (eV) of the electron transport layer (Ah≥Aed≥Ae), the organic light-emitting diode of the present disclosure can increase the electron density in the light-emitting layer, which shifts the dipole location zone toward the hole transport layer, with the consequent improvement of current efficiency and EL intensity.

Meanwhile, the organic light-emitting diode of the present disclosure is advantageous over that of Korean Patent Unexamined Application Publication No. 10-2012-0092555 in that the electron-density-controlling layer (corresponding to the blocking layer of the conventional art) need not be made of a material that is greater in triplet energy than the host of the light-emitting layer in order to effectively induce the TTF phenomenon.

Figure 4:
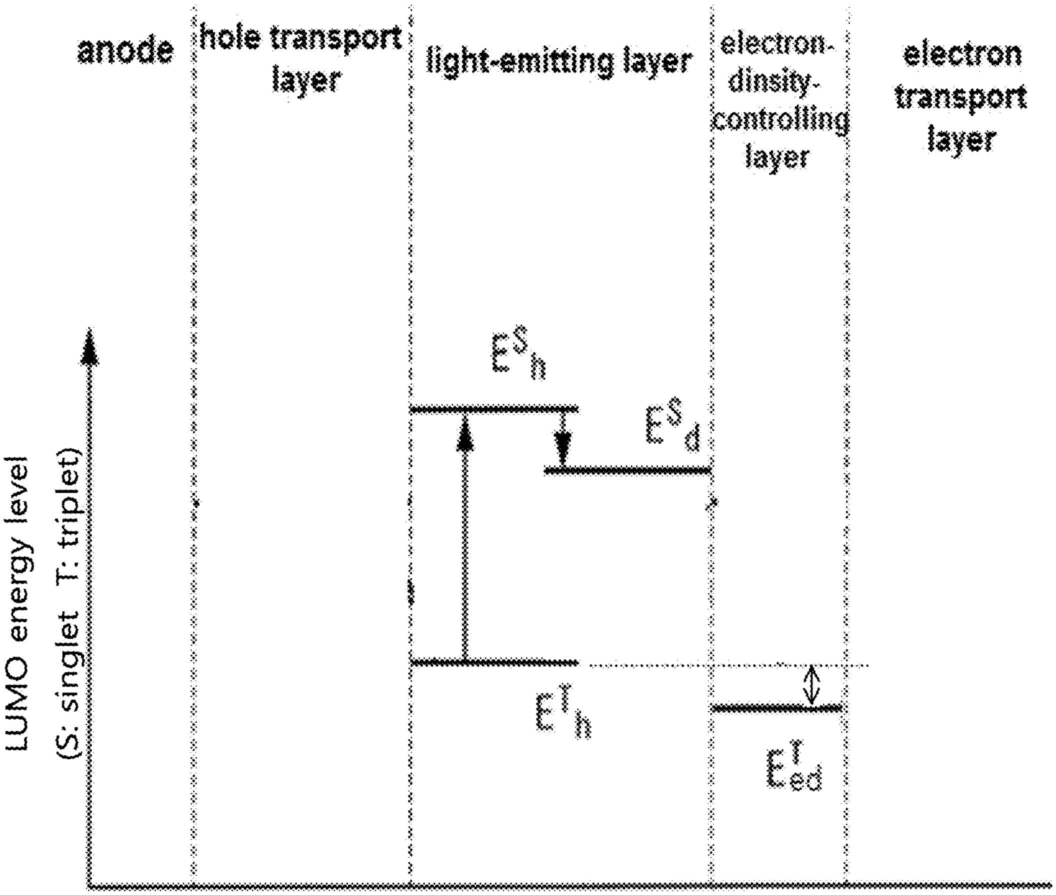
FIG. 4 is a diagram of the energy level structure of a light-emitting diode in which the triplet energy of an electron-density-controlling layer is lower than that of the host of a light-emitting layer in accordance with one embodiment of the present disclosure.

This advantage can be elucidated in detail with reference to FIG. 4. FIG. 4 is a diagram of the energy level structure of a light-emitting diode in which the triplet energy (ETed) of an electron-density-controlling layer is lower than that (ETh) of the host of a light-emitting layer in accordance with one embodiment of the present disclosure. As shown in FIG. 4, the material of the electron-density-controlling layer may be lower in triplet energy than that of the host of the light-emitting layer.

In one exemplary embodiment, the difference in triplet energy between the host of the light-emitting layer (ETh (eV)) and an anthracene derivative of the electron-density-controlling layer (ETed (eV)) may range from 0 to 0.4 (0.4 eV≥ETh−ETed≥0 eV), and more particularly from 0 to 0.3 ((0.3 eV≥ETh−ETed≥0 eV).

According to one embodiment of the present disclosure, the electron mobility of the anthracene derivative of the electron-density-controlling layer may be the same as or greater than that of the material of the electron transport layer. Since the electron-density-controlling layer is not smaller in electron mobility than the electron transport layer, the electrons supplied from the electron transport layer can move quickly toward the light-emitting layer without delay in the electron-density-controlling layer, thereby facilitating the elevation of exciton density in the light-emitting layer.

Figure 5:
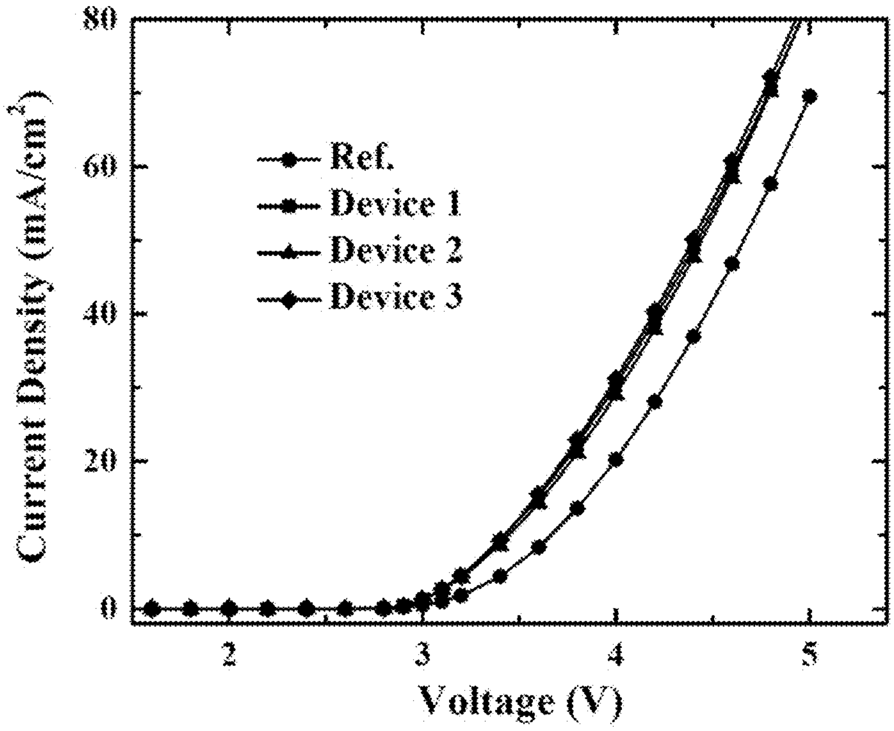
FIG. 5 shows changes in current efficiency with voltage in organic light-emitting diodes in which an electron-density-controlling layer is either present or absent.
Figure 5:
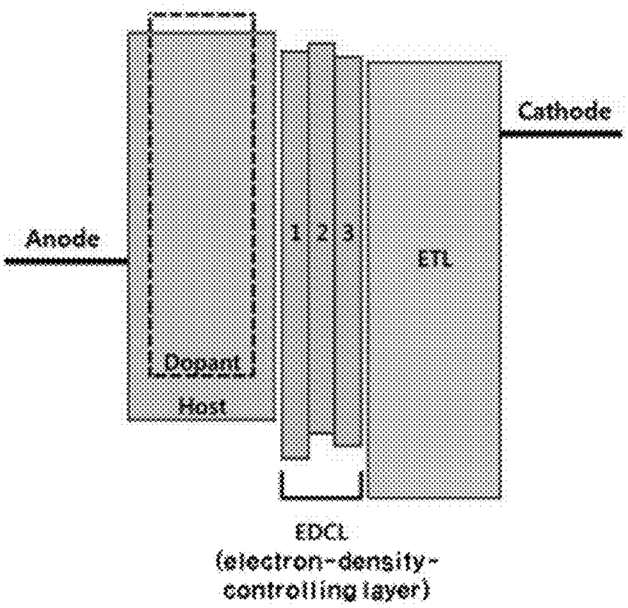

With regard to details of current density, reference may be made to FIG. 5.

FIG. 5 shows changes in current efficiency with voltage depending on the presence or absence of an electron-density-controlling layer in an organic light-emitting diode. In order to obtain the effect of the electron-density-controlling layer on electron mobility, an electron-only device (EOD), fabricated as shown in the lower panel of FIG. 5, was measured for current density while directly applying voltages thereto.

As can be understood from the upper diagram of FIG. 5, an electron-density-controlling layer helps increase the current density at the same voltage.

Thus, it has been discovered that the introduction of an electron-density-controlling layer enhances the electron injection properties of the device.

For more accurate arithmetic comparison, the electron mobility (ρ) in each device may be measured. In this regard, regardless of whether or not an electron-density-controlling layer is introduced thereinto, all of the devices to be tested were fabricated to have the same overall thickness so as to exclude an error factor in calculating electron mobility.

To calculate the electron mobility from the data measured in EOD devices, the following relationship between mobility and electric conductivity (σ) was used (G. Paasch et al. Synthetic Metals Vol. 132, pp. 97-104 (2002)).

First, the device was measured for resistance (R) from the current-voltage data, and for electric conductivity from the overall thickness (d) and pixel area (A) using the following Equation 1. Based on the electric conductivity, electron mobility was obtained according to the following Equation 2.

$$\sigma = \frac{1}{R} \times \frac{d}{A},\ R = \frac{V}{I} \qquad \text{Equation (1)}$$

$$\mu\ (\mathrm{cm}^2/Vs) = \sigma^{0.76}(S/\mathrm{cm}) \qquad \text{Equation (2)}$$

Figure 6:
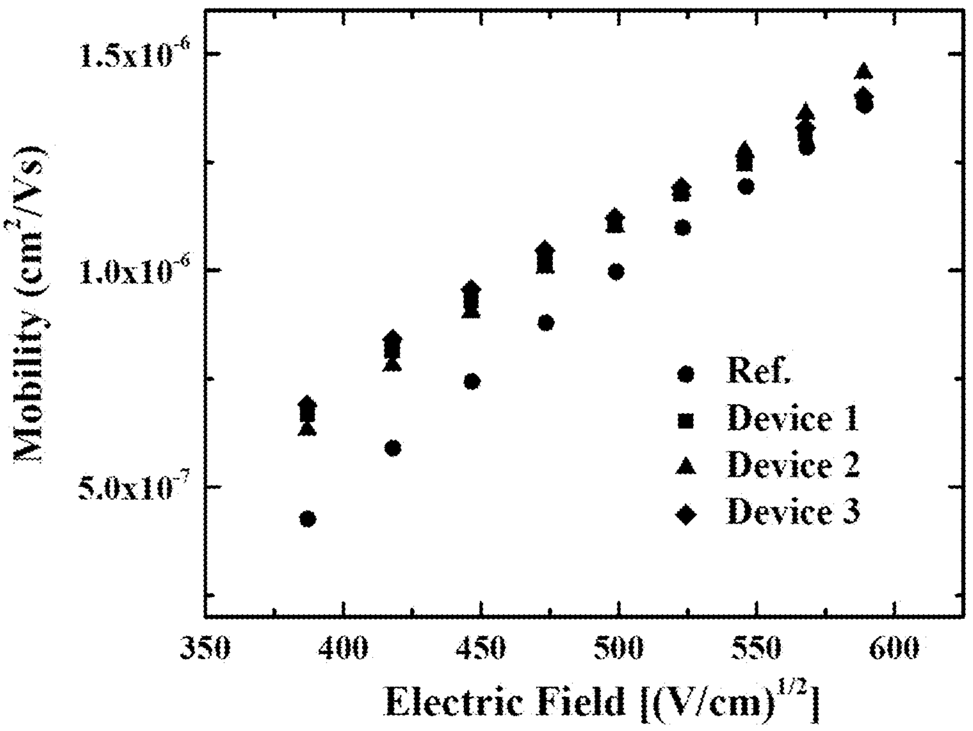
FIG. 6 is a diagram of electron mobility plotted against electric field for the organic light-emitting diodes in which an electron-density-controlling layer is present or absent.

FIG. 6 is a diagram of mobility plotted against electric field depending on the presence or absence of an electron-density-controlling layer in an organic light-emitting diode.

It is therefore understood from the data of FIG. 6 that when the electron-density-controlling layer is not lower in electron mobility than the electron transport layer, the electrons supplied from the electron transport layer can move quickly toward the light-emitting layer without a delay in the electron-density-controlling layer, thereby facilitating the increase of exciton density in the light-emitting layer.

According to exemplary embodiments of the present disclosure, the electron-density-controlling layer and the electron transport layer may have electron mobility of at least 10-6 cm2/Vs at an electronic field strength of 0.04 MV/cm to 0.5 MV/cm.

So long as it functions to stably transport the electrons from the cathode, any known material may be used for the electron transport layer. Examples of the known electron transport material include quinoline derivatives, particularly tris(8-quinolinolate)aluminum (Alq3), Liq, TAZ, Balq, beryllium bis(benzoquinolin-10-oate: Bebq2), ADN, compound 201, compound 202, BCP, and the oxadiazole derivatives PBD, BMD, and BND, but are not limited thereto.

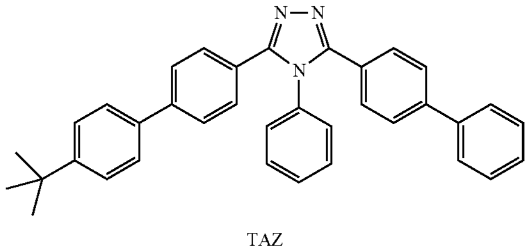

TAZ

-continued

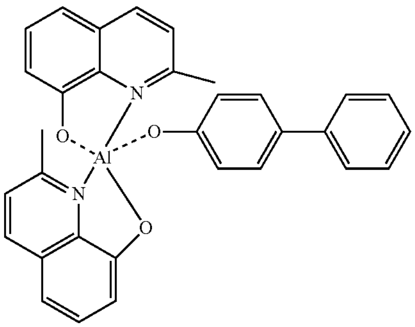

BAlq

<Cpd. 201>

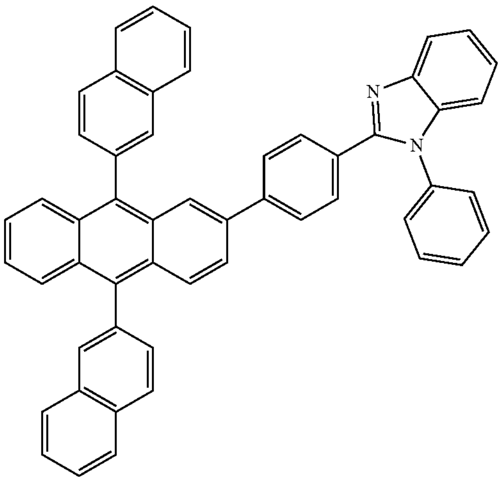

<Cpd. 202>

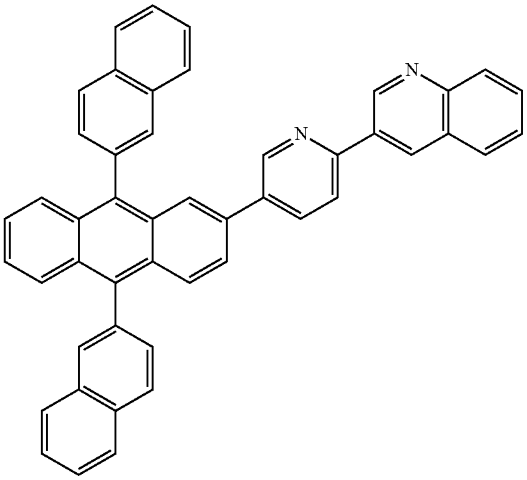

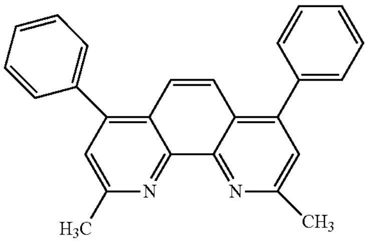

BCP

-continued

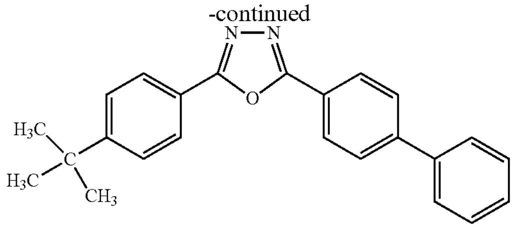

PBD

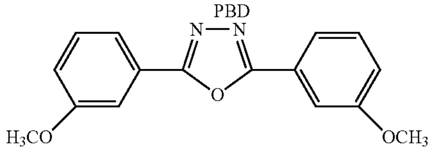

BMD

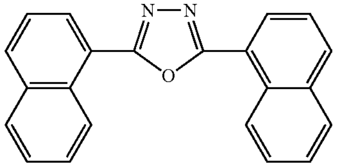

BND

As described above, an electron injection layer (EIL) is positioned on the electron transport layer in the organic light-emitting diode of the present invention. So long as it functions to facilitate the injection of electrons from the cathode, any known material may be available for forming the electron injection layer, without particular limitation.

By way of example, the material for the electron injection layer may be CsF, NaF, LiF, NaCl, Li2O, or BaO. The condition for depositing the electron injection layer is dependent on the compound that is employed, but may fall within the range of conditions for the formation of the hole injection layer.

The electron injection layer may range in thickness from about 1 Å to about 100 Å, and particularly from about 3 Å to about 90 Å. Given this thickness range, the electron injection layer can exhibit satisfactory electron injection properties without an actual increase in driving voltage.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be employed to form a transparent cathode for a top-emitting organic light-emitting diode.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting diode of the present disclosure may have a multilayer structure in which the additional blue, green, and/or red light-emitting layer may be made of a fluorescent or phosphorescent material.

Further, one or more layers selected from among the hole injection layer, the hole transport layer, the light-emitting layer, the electron-density-controlling layer, the electron transport layer, and the electron injection layer may be deposited using a single molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or white flat illumination devices, and monochrome or white flexible illumination devices.

A better understanding of the light-emitting diode according to the present disclosure may be obtained through the following examples which are set forth to illustrate, but are not to be construed as limiting the present disclosure.

EXAMPLES

Preparation of Host Compounds Useful for Light-Emitting Layer

Synthesis Example 1: Synthesis of Compound 76

Synthesis Example 1-(1): Synthesis of <Intermediate 1-a>

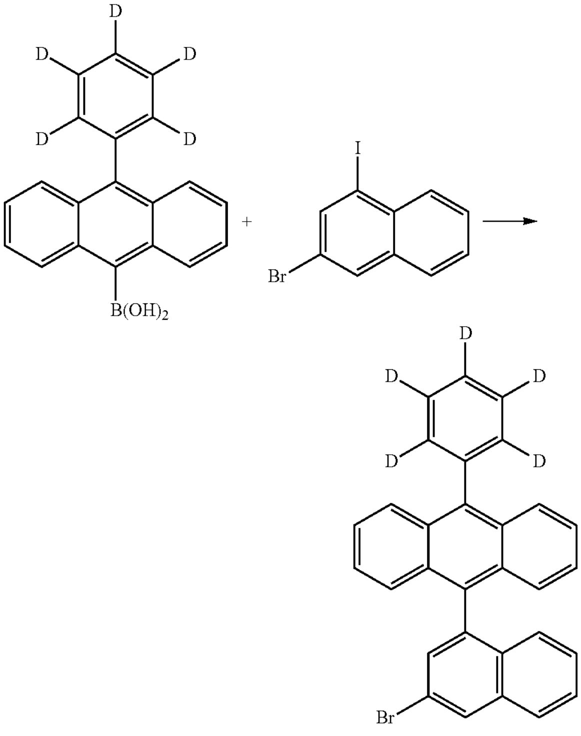

<Intermediate 1-a>

Into a 500-mL round-bottom flask reactor, (10-phenyl (d5)-anthracene-9-boronic acid (38.6 g, 127 mmol), 1-bromo-4-iodobenzoate (35.3 g, 106 mmol), tetrakis(triphenylphosphine)palladium (3.43 g, 3 mmol), and potassium carbonate (27.35 g, 197.9 mmol) were introduced, followed by adding toluene (150 mL), tetrahydrofuran (150 mL) and water (60 mL). The temperature of the reactor was elevated to 90° C., at which temperature the solution was stirred overnight. After completion of the reaction, the reaction mixture was cooled to room temperature and extracted with ethyl acetate. The organic layer thus formed was separated and concentrated in a vacuum. Purification of the concentrate by column chromatography afforded <Intermediate 1-a>. (34.1 g, 69.3%)

Synthesis Example 1-(2): Synthesis of <Intermediate 1-b>

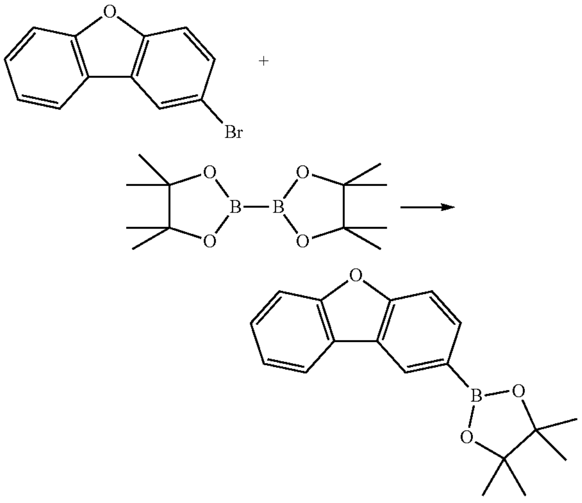

<Intermediate 1-b>

In a 2-L round-bottom flask reactor, 2-bromobenzofuran (70.0 g, 0.283 mol), bis(pinacolato)diboron (86.3 g, 0.340 mol), 1,1'-bis(diphenylphosphino)ferrocene-palladium (II) dichloride (4.6 g, 0.006 mol), potassium acetate (56.6 g, 0.567 mol), and 1,4-dioxane (700 ml) were stirred overnight under reflux. After completion of the reaction, filtration through a celite pad was conducted, and the filtrate was concentrated in a vacuum. Purification of the concentrate by column chromatography afforded <Intermediate 1-b>. (66.4 g, 79%)

Synthesis Example 1-(3): Synthesis of Compound 76

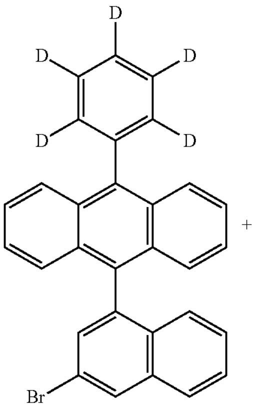

<Intermediate 1-a>

-continued

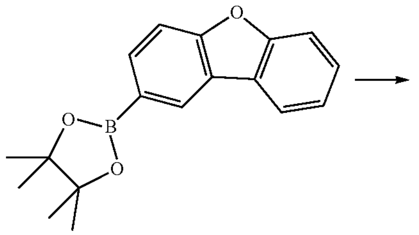

<Intermediate 1-b>

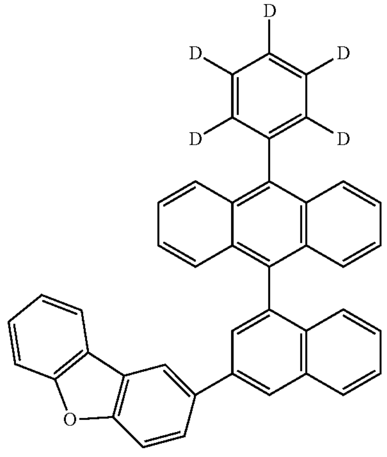

<Cpd. 76>

Into a 250-mL round-bottom flask reactor, <Intermediate 1-a> (6.0 g, 13 mmol), <Intermediate 1-b> (4.7 g, 16 mmol), tetrakis(triphenylphosphine)palladium (0.46 g, 3 mmol), and potassium carbonate (3.67 g, 26.5 mmol) were introduced, followed by adding toluene (30 mL), 1,4-dioxane (30 mL) and water (11 mL). The temperature of the reactor was elevated to 90° C., at which temperature the solution was stirred overnight. After completion of the reaction, the reaction mixture was cooled to room temperature and extracted with ethyl acetate. The organic layer thus formed was separated and concentrated in a vacuum. Purification of the concentrate by column chromatography afforded Compound 76. (3.4 g, 48%)

MS: m/z 551.23 [M+]

Synthesis Example 2: Synthesis of Compound 103

Synthesis Example 2-(1): Synthesis of Compound 103

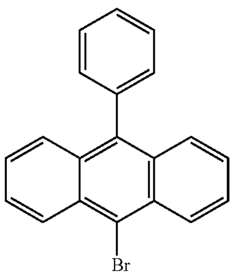

+

-continued

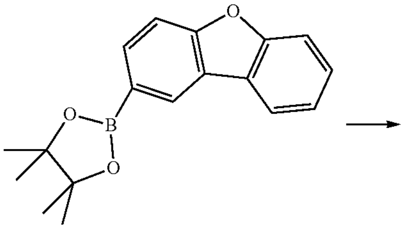

<Intermediate 1-b>

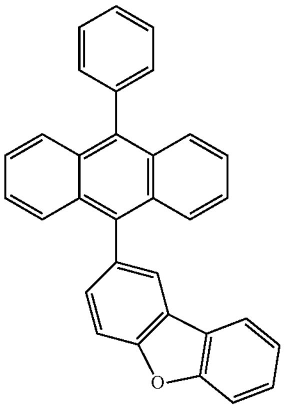

<Cpd. 103>

With the exception that 9-bromo-10-phenylanthracene was used instead of Intermediate 1-a, the same procedure as in Synthesis Example 1-(3) was carried out to afford Compound 103 (3.5 g, 57%).

MS: m/z 420.15 [M+]

Synthesis Example 3: Synthesis of Compound 140

Synthesis Example 3-(1): Synthesis of Intermediate 3-a

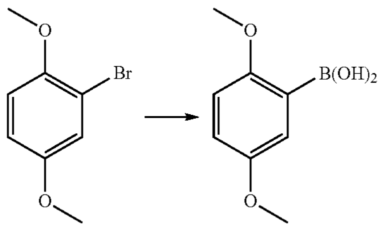

<Intermediate 3-a>

In a 1-L round-bottom flask reactor, 2-bromo-1,4-dimethoxybenzene (50 g, 230 mmol) and tetrahydrofuran (400 ml) were dissolved. After the mixture was cooled to −78° C., it was added with drops of N-butyl lithium (167 ml, 280 mmol). At the same temperature, the mixture was stirred for 2 hrs before the addition of trimethyl borate (36 ml, 320 mmol). Stirring was conducted overnight at room temperature. After completion of the reaction, 2 N HCl was dropwise added for acidification. Extraction with water and ethyl acetate gave an organic layer which was then dried over magnesium sulfate and concentrated in a vacuum. Recrystallization in heptane and toluene afforded <Intermediate 5-a>. (20.8 g, 50%)

Synthesis Example 3-(2): Synthesis of Intermediate 3-b

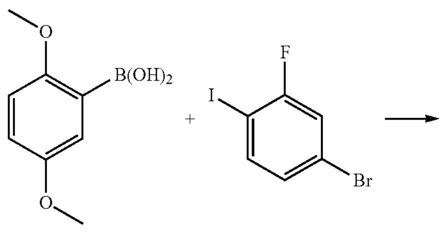

<Intermediate 3-a>

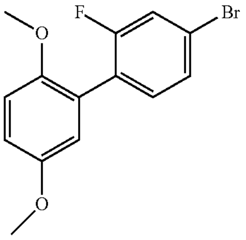

<Intermediate 3-b>

With the exception that 1-bromo-3-fluoro-4-iodo benzene and Intermediate 3-a were used instead of Intermediate 1-a and Intermediate 1-b, respectively, the same procedure as in Synthesis Example 1-(3) was carried out to afford Intermediate 3-b. (22.3 g, 63%)

Synthesis Example 3-(3): Synthesis of Intermediate 3-c

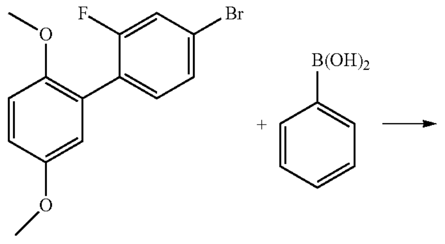

<Intermediate 3-b>

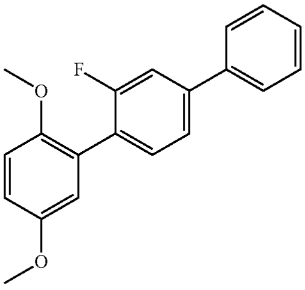

<Intermediate 3-c>

With the exception that Intermediate 3-b and phenyl borate were used instead of Intermediate 1-a and Intermediate 1-b, respectively, the same procedure as in Synthesis Example 1-(3) was carried out to afford Intermediate 3-c. (16.3 g, 74%)

Synthesis Example 3-(4): Synthesis of Intermediate 3-d

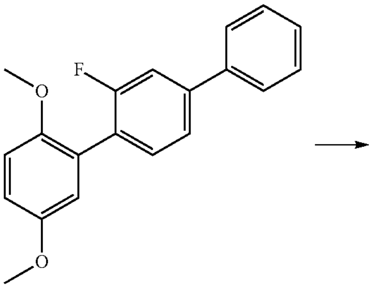

<Intermediate 3-c>

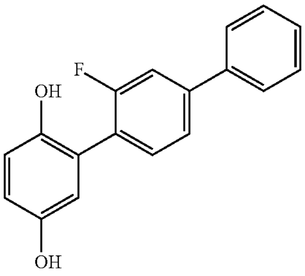

<Intermediate 3-d>

In a 500-ml round-bottom flask reactor, <Intermediate 3-c (16.3 g, 53 mmol), hydrobromic acid (48 ml, 260 mmol) and acetic acid (100 ml) were stirred together for 12 hrs. After completion of the reaction, the reaction mixture was cooled to room temperature, added with water, and stirred. Then, the reaction mixture was extracted with water and ethyl acetate. The organic layer thus formed was separated, concentrated in a vacuum, and recrystallized in heptane. Filtration and dehydration afforded <Intermediate 3-d>. (14 g, 95%)

Synthesis Example 3-(5): Synthesis of Intermediate 3-e

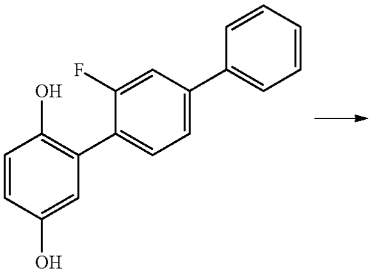

<Intermediate 3-d>

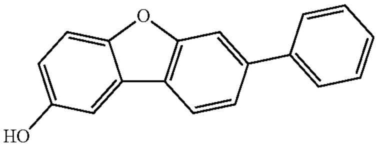

<Intermediate 3-e>

In a 500-ml round-bottom flask reactor, <Intermediate 3-d> (14 g, 50 mmol), potassium carbonate (20.7 g, 150 mmol) and N-methyl-2-pyrrolidone (112 ml) were stirred together for 12 hrs. After completion of the reaction, extraction with water and ethyl acetate gave an organic layer. The organic layer was separated and concentrated in a vacuum. Recrystallization in heptane afforded <Intermediate 3-e>. (10.5 g, 81%)

Synthesis Example 3-(6): Synthesis of Intermediate 3-f

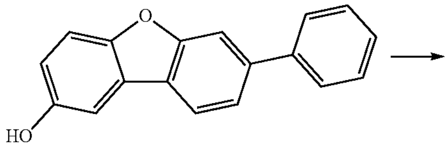

<Intermediate 3-e>

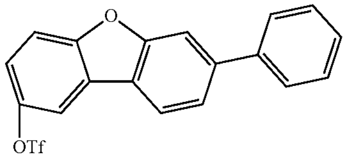

<Intermediate 3-f>

In a 500-ml round-bottom flask reactor, <Intermediate 3-e> (13.6 g, 52 mmol) was dissolved in dichloromethane (136 ml) under a nitrogen atmosphere. The reaction solution was cooled to 0° C., and pyridine (10 ml, 110 mmol) was added thereto. At the same temperature, trifluoromethane sulfonyl anhydride (12.7 g, 68 mmol) was dropwise added. The resulting reaction mixture was stirred at room temperature for 12 hrs and mixed with water (20 ml). Extraction with water and dichloromethane gave an organic layer which was then concentrated in a vacuum. Recrystallization in heptane afforded <Intermediate 3-f>. (7.5 g, 37%)

Synthesis Example 3-(7): Synthesis of Compound 140

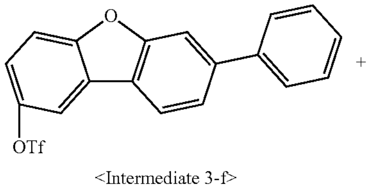

<Intermediate 3-f>

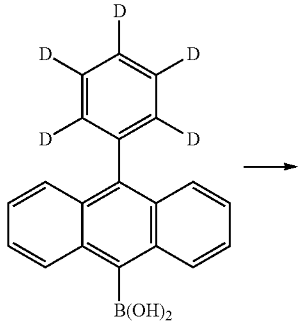

-continued

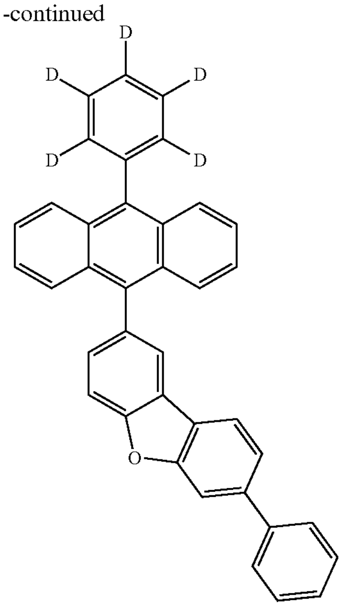

<Chemical Formula 140>

In a 250-ml round-bottom flask reactor, <Intermediate 3-f> (7.5 g, 19 mmol), 10-phenyl (d5)-anthracene-9-boronic acid (7 g, 23 mmol), tetrakis(triphenylphosphine)palladium (0.66 g, 0.6 mmol) and potassium carbonate (7.9 g, 57 mmol) were stirred together with toluene (53 ml), ethanol (23 ml) and water (23 ml) for 12 hrs. After completion of the reaction, the mixture was cooled to room temperature and further stirred together with methanol. The organic layer was separated and concentrated in a vacuum. Recrystallization in toluene and acetone afforded <Compound 140>. (6 g, 63%)

MS: m/z 501.21 [M+]

Synthesis Example 4: Synthesis of Compound 150

Synthesis Example 4-(1): Synthesis of Intermediate 4-a

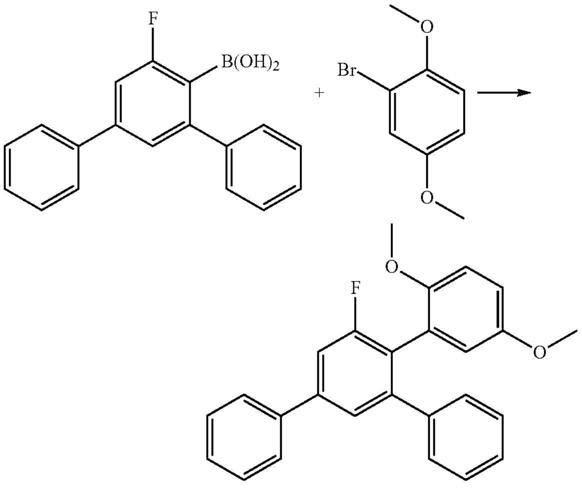

<Intermedaite 4-a>

With the exception that 2-bromo 1,4-dimethoxybenzene and 2-fluoro-(4,6-dipheneyl)-phenyl-1-boronic acid were used instead of <Intermediate 1-a> and <Intermediate 1-b>, respectively, the same procedure as in Synthesis Example 1-(3) was carried out to afford <Intermediate 4-a>. (22.6 g, 54%)

Synthesis Example 4-(2): Synthesis of Intermediate 4-b

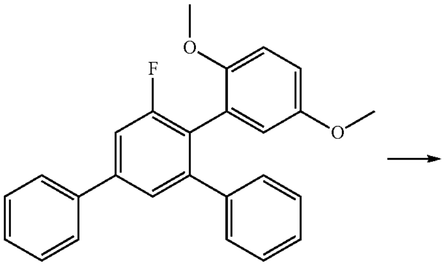

<Intermedaite 4-a>

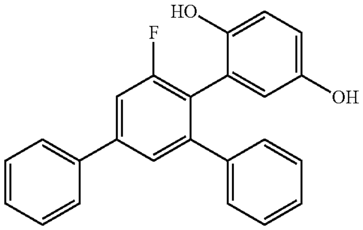

<Intermedaite 4-b>

With the exception that <Intermediate 4-a> was used instead of <Intermediate 3-c>, the same procedure as in Synthesis Example 3-(4) was carried out to afford <Intermediate 4-b>. (15.7 g, 75%)

Synthesis Example 4-(3): Synthesis of Intermediate 4-c

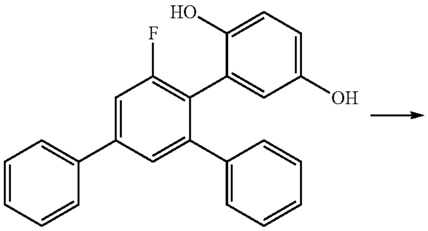

<Intermedaite 4-b>

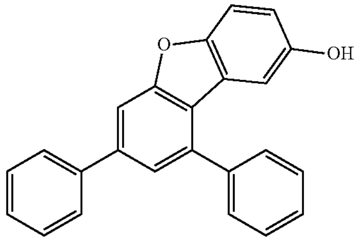

<Intermedaite 4-c>

With the exception that <Intermediate 4-b> was used instead of <Intermediate 3-d>, the same procedure as in Synthesis Example 3-(5) was carried out to afford <Intermediate 4-c>. (11.4 g, 77%)

Synthesis Example 4-(4): Synthesis of Intermediate 4-d

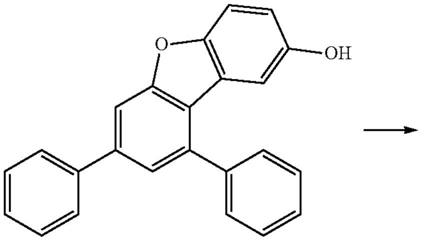

<Intermedaite 4-c>

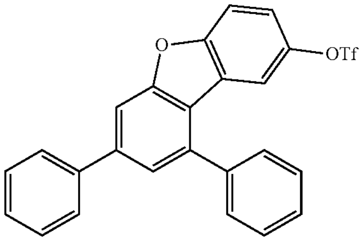

<Intermedaite 4-d>

With the exception that <Intermediate 4-c> was used instead of <Intermediate 3-e>, the same procedure as in Synthesis Example 3-(6) was carried out to afford <Intermediate 4-d>. (9.9 g, 62%)

Synthesis Example 4-(4): Synthesis of Compound 150

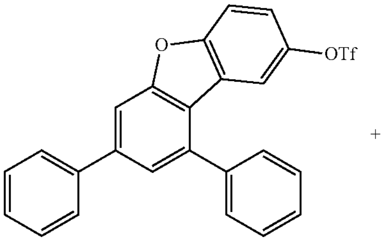

<Intermedaite 4-d>

+

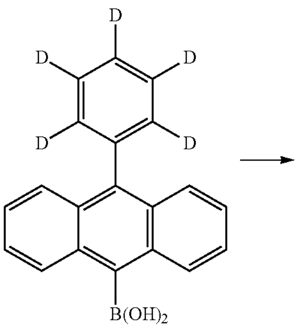

-continued

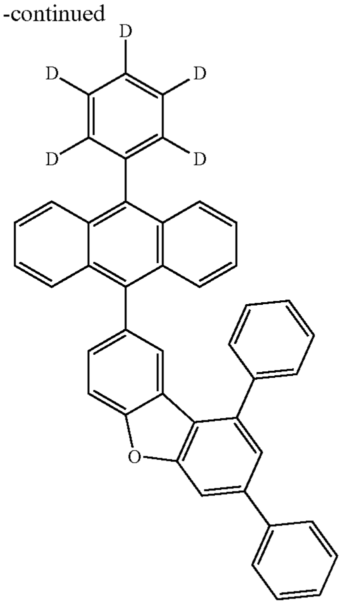

<Cpd. 150>

With the exception that <Intermediate 4-d> was used instead of <Intermediate 3-f>, the same procedure as in Synthesis Example 3-(7) was carried out to afford <Compound 150>. (7.6 g, 62%)

MS: m/z 577.25 [M+]

Synthesis Example 5: Synthesis of Compound 151

Synthesis Example 5-(1): Synthesis of Intermediate 5-a

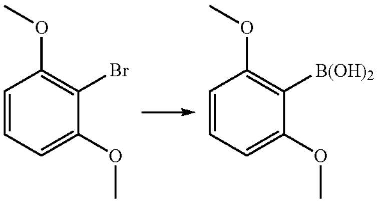

<Intermediate 5-a>

With the exception that 2-bromo-1,3-dimethoxybenzene was used instead of 2-bromo-1,4-dimethoxybenzene, the same procedure as in Synthesis Example 3-(1) was carried out to afford <Intermediate 5-a>. (23 g, 55%)

Synthesis Example 5-(2): Synthesis of Intermediate 5-b

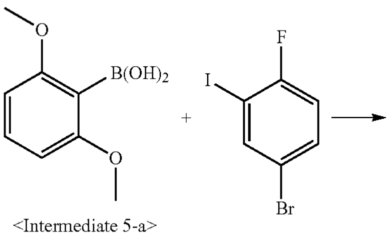

<Intermediate 5-a>

-continued

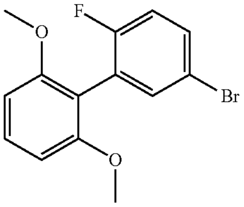

<Intermediate 7-b>

With the exception that 4-bromo 1-fluoro 2-iodobenzene was used instead of <Intermediate 1-a>, the same procedure as in Synthesis Example 1-(3) was carried out to afford <Intermediate 5-b>. (21.3 g, 54%)

Synthesis Example 5-(3): Synthesis of Intermediate 5-c

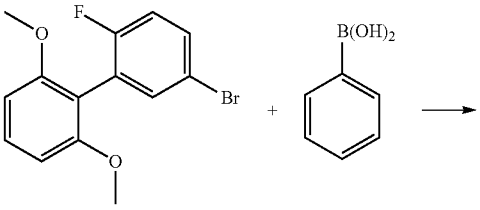

<Intermediate 5-b>

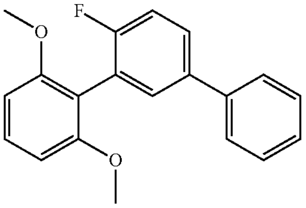

<Intermediate 5-c>

With the exception that <Intermediate 5-b> and phenyl borate were used instead of <Intermediate 1-a> and <Intermediate 1-b>, respectively, the same procedure as in Synthesis Example 1-(3) was carried out to afford <Intermediate 5-c>. (15.8 g, 75%)

Synthesis Example 5-(4): Synthesis of Intermediate 5-d

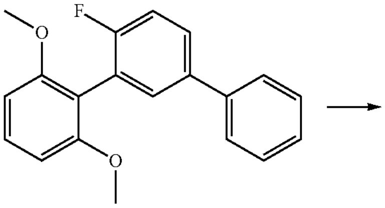

<Intermediate 5-c>

-continued

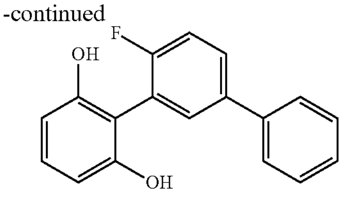

<Intermediate 5-d>

With the exception that <Intermediate 5-c> was used instead of <Intermediate 3-c>, the same procedure as in Synthesis Example 3-(4) was carried out to afford <Intermediate 5-d>. (11 g, 77%)

Synthesis Example 5-(5): Synthesis of Intermediate 5-e

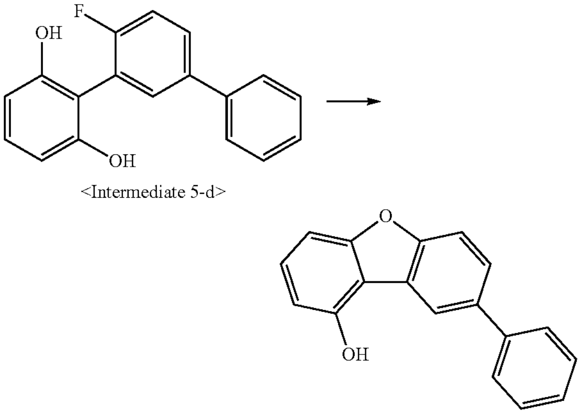

<Intermediate 5-d>

<Intermediate 5-e>

With the exception that <Intermediate 5-d> was used instead of <Intermediate 3-d>, the same procedure as in Synthesis Example 3-(5) was carried out to afford <Intermediate 5-e>. (9.3 g, 91%)

Synthesis Example 5-(6): Synthesis of Intermediate 5-f

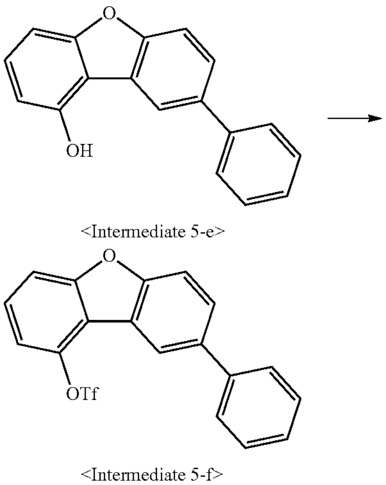

<Intermediate 5-e>

<Intermediate 5-f>

With the exception that <Intermediate 5-e> was used instead of <Intermediate 3-e>, the same procedure as in Synthesis Example 3-(6) was carried out to afford <Intermediate 5-f>. (7.9 g, 56%)

Synthesis Example 5-(7): Synthesis of Compound 151

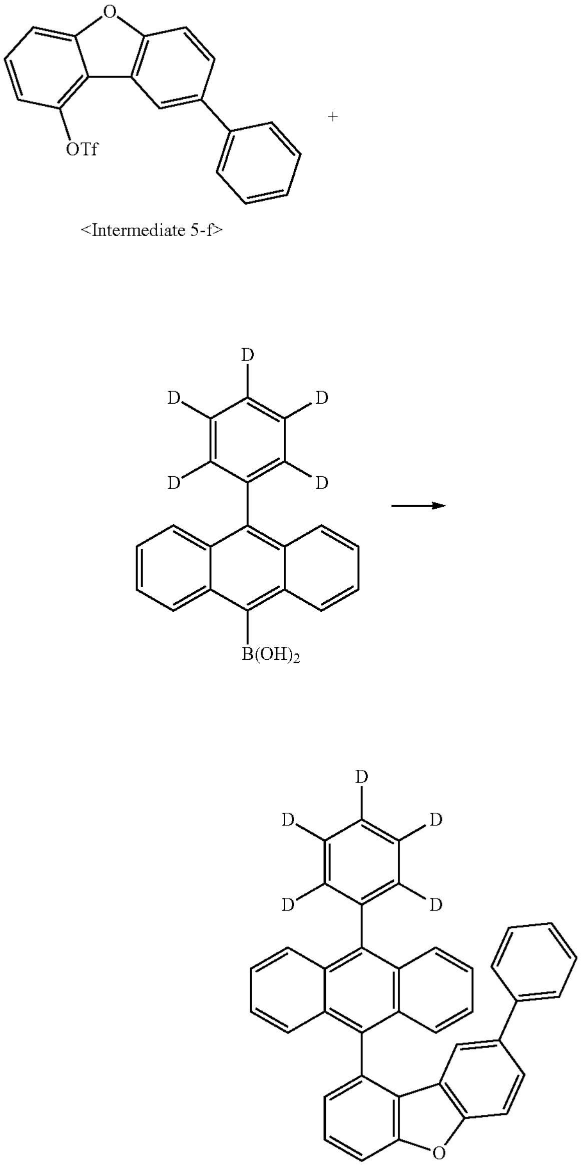

<Intermediate 5-f>

+

<Chemical Formula 151>

With the exception that <Intermediate 5-f> was used instead of <Intermediate 3-f>, the same procedure as in Synthesis Example 3-(7) was carried out to afford <Compound 151>. (7.1 g, 70%)

MS: m/z 501.21 [M+]

Preparation of Compounds for Electron-Density-Controlling Layer

Synthesis Example 6: Synthesis of Compound 203

Synthesis Example 6-(1): Synthesis of Intermediate 6-a

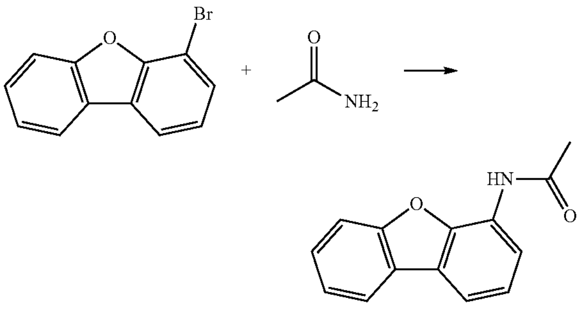

<Intermediate 6-a>

In a 2 L-round-bottom flask reactor, 4-bromodibenzofuran (150.0 g, 0.607 mol), acetamide (53.8 g, 0.911 mol), copper iodide (57.8 g, 0.30 mol), (±)trans-1,2-diaminocyclohexane (63.9 g, 0.60 mol), potassium carbonate (167.8 g, 1.21 mol), and toluene (1500 ml) were stirred overnight together under reflux. After completion of the reaction, filtration through a silica gel pad was carried out, and the filtrate was washed many times with hot toluene. The filtrate was concentrated in a vacuum, and the concentrate was crystallized in acetonitrile, followed by filtration to afford <Intermediate 6-a>. (70.0 g, 51%)

Synthesis Example 6-(2): Synthesis of Intermediate 3-b

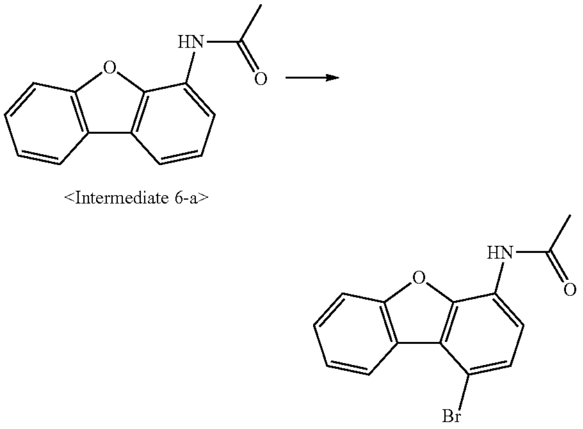

<Intermediate 6-a>

<Intermediate 6-b>

In a 2-L round-bottom flask reactor, <Intermediate 6-a> (70.0 g, 0.311 mol) was dissolved in acetic acid (630 ml). A mixture of bromine (49.7 g, 0.311 mol) and acetic acid (280 ml) was dropwise added into the reactor. At room temperature, the mixture was stirred for 2 hrs, and then water (100 ml) was added and the mixture was further stirred. The gray solid thus formed was slurried in ethanol (500 ml), stirred, and filtered. Dehydration of the filtrate afforded <Intermediate 6-b>. (86.0 g, 91%)

Synthesis Example 6-(3): Synthesis of Intermediate 6-c

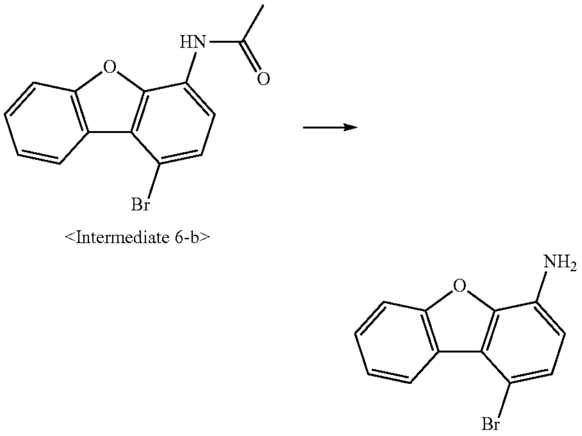

<Intermediate 6-b>

<Intermediate 6-c>

In a 2-L round-bottom flask reactor, <Intermediate 6-b> (86.0 g, 0.283 mol) was dissolved in ethanol (600 ml) and tetrahydrofuran (430 ml) and stirred. A solution of potassium hydroxide (47.6 g, 0.848 mol) in water (260 ml) was slowly added to the reactor, followed by stirring overnight under reflux. After completion of the reaction, the reaction mixture was cooled to room temperature. Extraction with ethyl acetate and water gave an organic layer which was then concentrated in a vacuum. The concentrate was stirred in excess ethanol and filtered. Recrystallization in methylene chloride and heptane afforded <Intermediate 6-c>. (73.0 g, 98%)

Synthesis Example 6-(4): Synthesis of Intermediate 6-d

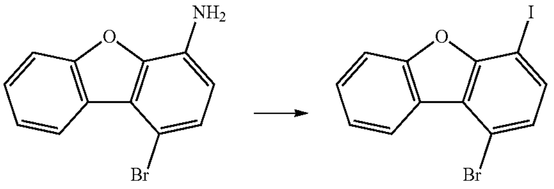

<Intermediate 6-c> <Intermediate 6-d>

In a 2-L round-bottom flask reaction, <Intermediate 6-c> (73.0 g, 0.279 mol), HCl (90 ml), and water (440 ml) were stirred together at 0° C. At the same temperature, an aqueous solution (90 ml) of sodium nitrite (25.0 g, 0.362 mol) was dropwise added to the reaction mixture and then stirred for 1 hr. An aqueous solution (90 ml) of potassium iodide (92.5 g, 0.557 mol) was dropwise added and stirred at room temperature. After completion of the reaction, the reaction mixture was extracted with ethyl acetate and water. The organic layer thus obtained was then washed with an aqueous sodium thiosulfate solution, separated, and concentrated in a vacuum. Purification through column chromatography gave <Intermediate 6-d>. (52.3 g, 50.3%).

Synthesis Example 6-(5): Synthesis of Intermediate 6-e

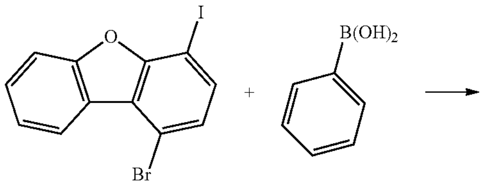

<Intermediate 6-d>

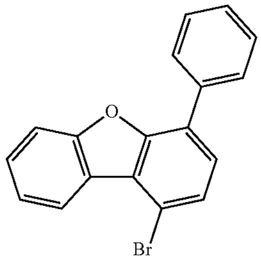

<Intermediate 6-e>

In a 2-L round-bottom flask reactor, <Intermediate 6-d> (15.0 g, 40 mmol), phenyl borate (5.4 g, 44 mmol), tetrakis (triphenylphosphine)palladium (0.9 g, 1 mmol), and potassium carbonate (11.1 g, 80 mmol) were stirred overnight together with toluene (100 mL), methanol (45 mL) and water (30 mL) under reflux. After completion of the reaction, the reaction mixture was cooled to room temperature and extracted with ethyl acetate. The organic layer was concentrated in a vacuum and separated by column chromatography. The solid was recrystallized in heptane to afford <Intermediate 6-e>. (7.0 g, 53.9%)

Synthesis Example 6-(6): Synthesis of Compound 203

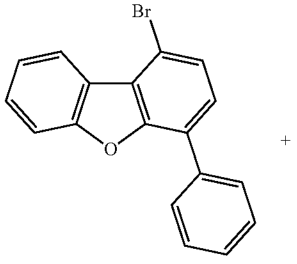

<Intermediate 6-e>

-continued

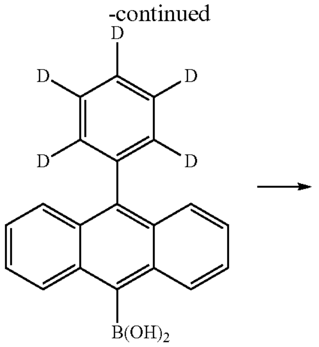

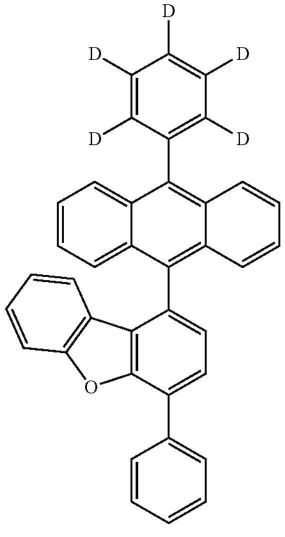

<Cpd. 203>

In a 250-mL round-bottom flask reactor, <Intermediate 6-e> (7.0 g, 22 mmol), (10-phenyl(d5)-anthracene-9-boronic acid (7.9 g, 26 mmol), tetrakis(triphenylphosphine) palladium (0.5 g, 1 mmol), and potassium carbonate (6.0 g, 43 mmol) were stirred overnight together with toluene (50 mL), ethanol (21 mL), and water (14 mL) at 90° C. After completion of the reaction, the reaction mixture was cooled to room temperature and then stirred together with methanol (50 ml). The solid thus formed was filtered and washed with methanol. The filtrate was recrystallized in toluene and acetone to afford <Compound 203>.

MS (MALDI-TOF): m/z 501.21 [M+]

Synthesis Example 7: Synthesis of Compound 209

Synthesis Example 7-(1): Synthesis of Intermediate 7-a

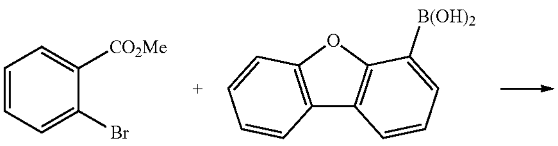

-continued

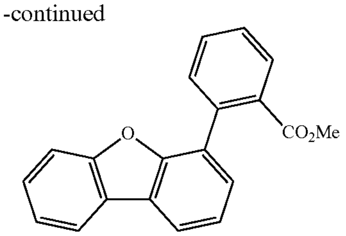

<Intermediate 7-a>

In a 500-mL round-bottom flask reactor, methyl 2-bromobenzoate (30.0 g, 0.140 mol), 4-dibenzoboronic acid (32.5 g, 0.153 mol), tetrakis(triphenylphosphine)palladium (3.2 g, 3 mmol), and potassium carbonate (38.6 g, 0.279 mol) were stirred overnight together with toluene (210 mL), methanol (90 mL) and water (60 mL). After completion of the reaction, the reaction mixture was cooled to room temperature and extracted with ethyl acetate. The organic layer thus formed was concentrated in a vacuum. Purification through column chromatography afforded Intermediate 7-a. (25.0 g, 59.1%)

Synthesis Example 7-(2): Synthesis of <Intermediate 7-b>

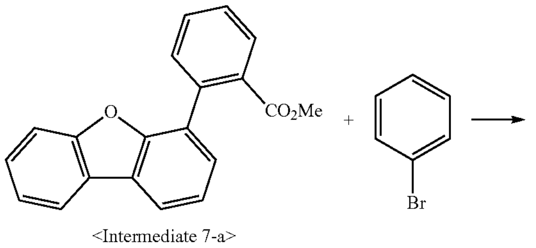

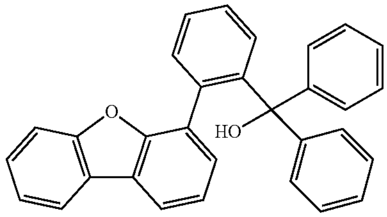

<Intermediate 7-b>

In a 500-ml round-bottom flask reactor, bromobenzene (28.6 g, 182 mmol) and tetrahydrofuran (220 ml) were cooled to −78° C. under a nitrogen atmosphere. At the same temperature, n-butyl lithium (104.6 ml, 167 mmol) was dropwise added to the chilled solution and stirred for 2 hrs. Then, <Intermediate 7-a> (22.0 g, 73 mmol) was added little by little at room temperature while stirring. After completion of the reaction, the reaction was stopped with H2O (50 ml), and extraction with ethyl acetate and water was conducted. The organic layer thus formed was concentrated in a vacuum to afford <Intermediate 7-b>. (28.0 g, 90%)

Synthesis Example 7-(3): Synthesis of Intermediate 7-c

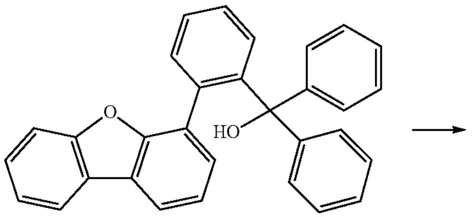

<Intermediate 7-b>

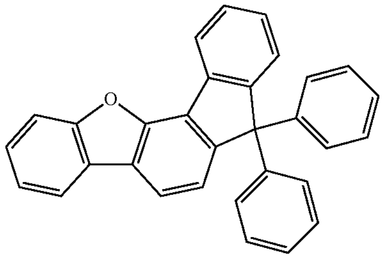

<Intermediate 7-c>

In a 500-ml round-bottom flask reactor, <Intermediate 7-b> (28.0 g, 66 mmol) acetic acid (310 ml) and HCl (2 ml) were stirred together for 1 hr under reflux. When a solid was formed, the completion of the reaction was confirmed by thin layer chromatography. After the reaction mixture was cooled to room temperature, the solid thus formed was filtered. The filtrate was washed with $H_2O$ and methanol and dried to afford <Intermediate 7-c>. (22.3 g, 83.2%>

Synthesis Example 7-(4): Synthesis of Intermediate 7-d

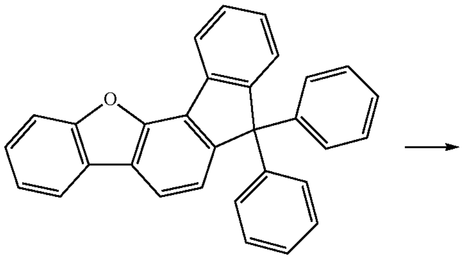

<Intermediate 7-c>

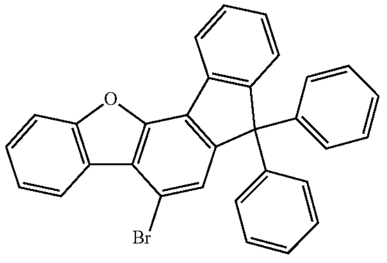

<Intermediate 7-d>

In a 2-L round-bottom flask reactor, <Intermediate 7-c> (22.3 g, 55 mmol) was dissolved in methylene chloride (500 ml). A mixture of bromine (8.72 g, 55 mmol) and methylene chloride (250 ml) was dropwise added to the reactor, followed by stirring at room temperature for 3 hrs. After completion of the reaction, the reaction mixture was washed with an aqueous sodium hydrogen carbonate solution. The solid thus formed was filtered and recrystallized in toluene and acetone to afford <Intermediate 7-d>. (25.0 g, 94%)

Synthesis Example 7-(5): Synthesis of Compound 209

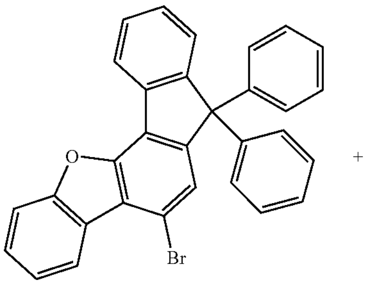

<Intermediate 7-d>

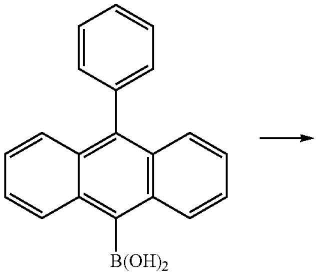

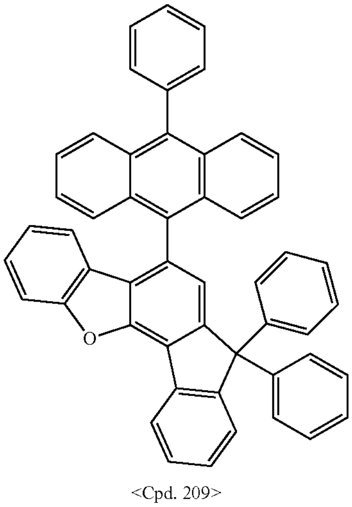

<Cpd. 209>

In a 250-mL round-bottom flask reactor, <Intermediate 7-d> (7.0 g, 14 mmol), (10-pheneyl-anthracene-9-boronic acid (5.1 g, 17 mmol), tetrakis(triphenylphosphine)palladium (0.3 g, 3 mmol), and potassium carbonate (4.0 g, 29 mmol) were stirred overnight together with toluene (49 mL), ethanol (21 mL), and water (14 mL) at 90° C. After completion of the reaction, the reaction mixture was cooled to room temperature and extracted with ethyl acetate. The organic layer thus formed was separated, concentrated in a vacuum, and purified by column chromatography. Recrystallization in methylene chloride and acetone afforded <Compound 209>.

MS (MALDI-TOF): m/z 660.25 [M+]

Synthesis Example 8: Synthesis of Compound 213

Synthesis Example 8-(1): Synthesis of Intermediate 8-a

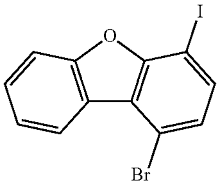

<Intermediate 6-d>

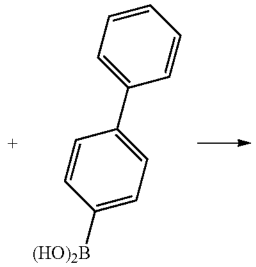

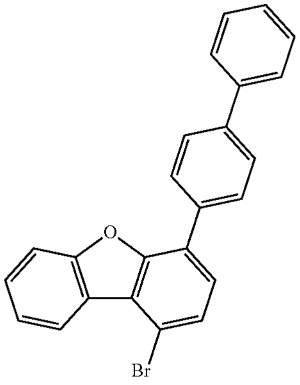

<Intermediate 8-a>

With the exception that 4-biphenyl boronic acid was used instead of phenyl boronic acid, the same procedure as in Synthesis Example 6-(5) was carried out to afford <Intermediate 8-a> (8.5 g, 55.9%).

Synthesis Example 8-(2): Synthesis of Compound 213

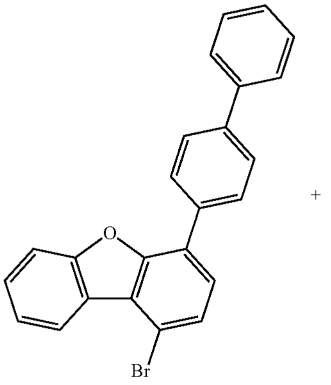

<Intermediate 8-a>

-continued

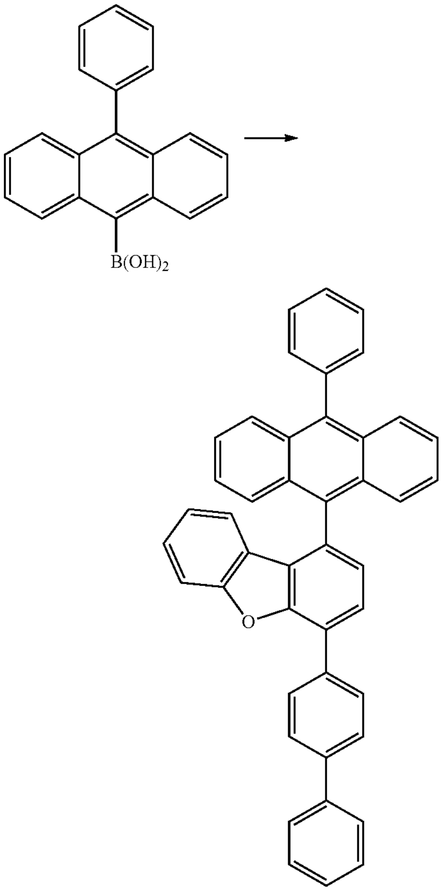

<Compound 213>

With the exception that <Intermediate 8-a> was used instead of <Intermediate 7-d>, the same procedure as in Synthesis Example 7-(5) was carried out to afford <Compound 213> (6.3 g, 51%).

MS (MALDI-TOF): m/z 572.21 [M+]

Synthesis Example 9: Synthesis of Compound 299

Synthesis Example 9-(1): Synthesis of Intermediate 9-a

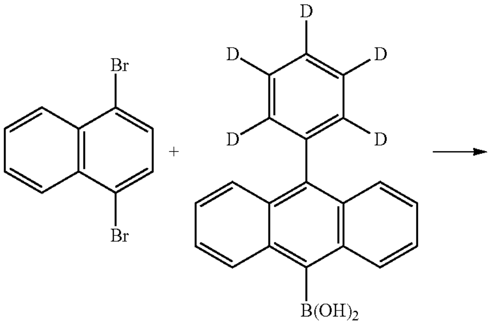

-continued

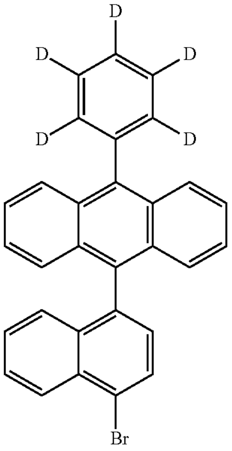

<Intermediate 9-a>

With the exception that 1,4-dibromonaphthalene was used instead of 1-bromo-4-iodobenzene, the same procedure as in Synthesis Example 1-(1) was carried out to afford <Intermediate 9-a> (29 g, 59.5%).

Synthesis Example 9-(2): Synthesis of Compound 299

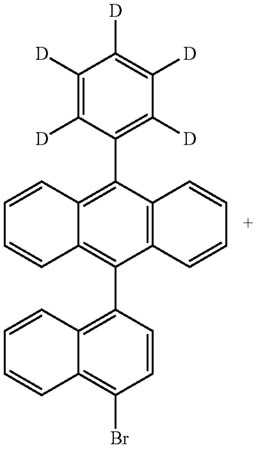

<Intermediate 9-a>

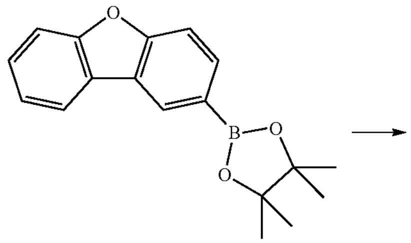

<Intermediate 1-b>

-continued

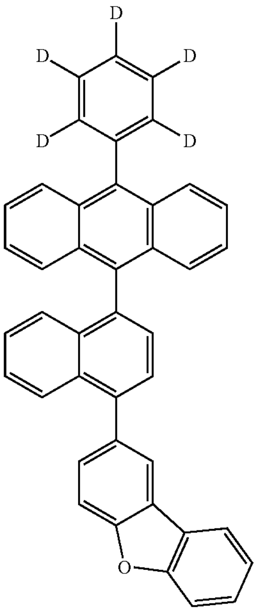

<Cpd. 299>

With the exception that <Intermediate 9-a> was used instead of <Intermediate 1-a>, the same procedure as in Synthesis Example 1-(3) was carried out to afford <Compound 299> (4.0 g, 67.4%).

MS: m/z 552.2 [M+]

Preparation of Dopant Compound

Synthesis Example 10: Synthesis of BD2

Synthesis Example 10-(1): Synthesis of [Intermediate 10-a]

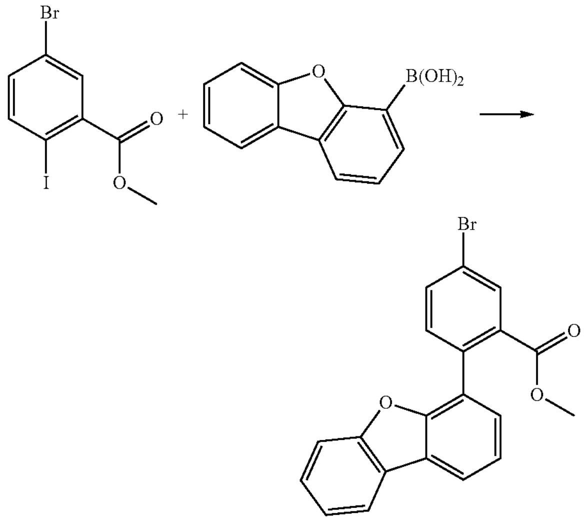

<Intermediate 10-a>

In a 500-mL round-bottom flask reactor, methyl 5-bromo-2-iodobenzoate (25.0 g, mmol), 4-dibenzofuran boronic acid (18.7 g, 88 mmol), tetrakis(triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 10-a>. (75.0 g, 60.1%).

Synthesis Example 10-(2): Synthesis of [Intermediate 10-b]

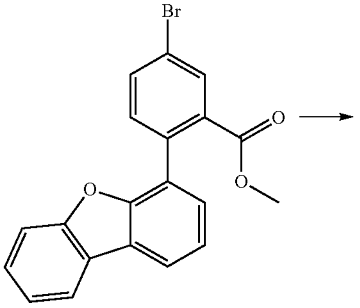

<Intermediate 10-a>

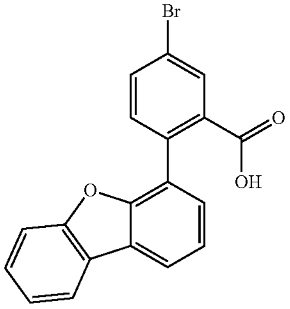

<Intermediate 10-b>

In a 500-mL round-bottom flask reactor, <Intermediate 10-a> (17.0 g, 45 mmol), sodium hydroxide (2.14 g, 54 mmol) and ethanol (170 ml) were stirred together for 48 hrs under reflux. After completion of the reaction was confirmed using thin layer chromatography, the reaction mixture was cooled to room temperature. The chilled solution was acidified with drops of 2-N HCl, followed by stirring for 30 min. The solid thus formed was filtered and recrystallized in dichloromethane and n-hexane to afford <Intermediate 10-b>. (14.5 g, 88.6%)

Synthesis Example 10-(3): Synthesis of [Intermediate 10-c]

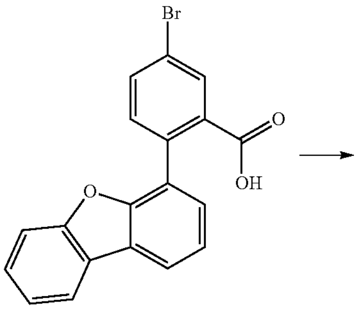

<Intermediate 10-b>

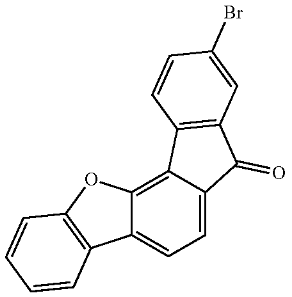

<Intermediate 10-c>

In a 250-mL round-bottom flask reactor, <Intermediate 10-b> (14.5 g, 39 mmol) and methanesulfonic acid (145 ml) were stirred together for 3 hrs at 80° C. After completion of the reaction was confirmed via thin layer chromatography, the reaction mixture was cooled to room temperature and dropwise added to ice water (150 ml). After stirring for 30 min, the solid thus formed was filtered and washed with water and methanol to afford <Intermediate 10-c>. (11.50 g, 83.4%)

Synthesis Example 10-(4): Synthesis of [Intermediate 10-d]

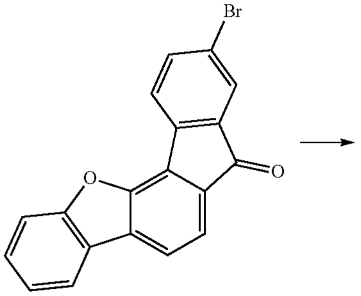

<Intermediate 10-c>

-continued

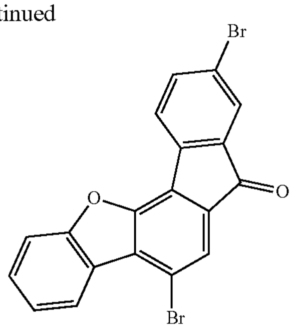

<Intermediate 10-d>

In a 1-L round-bottom flask reactor, <Intermediate 10-c> (11.5 g, 33 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 10-d>. (11.0 g, 78%)

Synthesis Example 10-(5): Synthesis of [Intermediate 10-e]

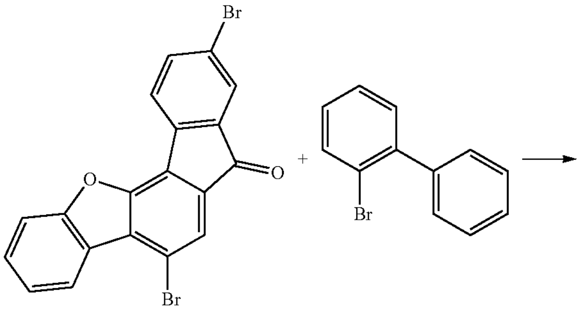

<Intermediate 10-d>

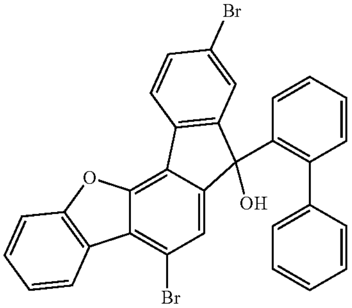

<Intermediate 10-e>

In a 250-ml round-bottom flask reactor, 2-bromobiphenyl (8.4 g, 0.036 mol) and tetrahydrofuran (110 ml) were frozen at −78° C. under a nitrogen atmosphere. At the same temperature, n-butyl lithium (19.3 ml, 0.031 mol) was dropwise added to the reaction solution, which was then stirred for 2 hrs. Thereafter, <Intermediate 7-d> (11.0 g, 0.026 mol) was added little by little to the reaction solution and stirred at room temperature. When the reaction mixture started to change color, the reaction was monitored via thin layer chromatography. After the reaction was stopped with $H_2O$ (50 ml), extraction was conducted with ethylacetate and water. The organic layer was separated, concentrated in a vacuum, and recrystallized in acetonitrile to afford <Intermediate 10-e> as a solid. (12.2 g, 81.5%)

Synthesis Example 10-(6): Synthesis of [Intermediate 10-f]

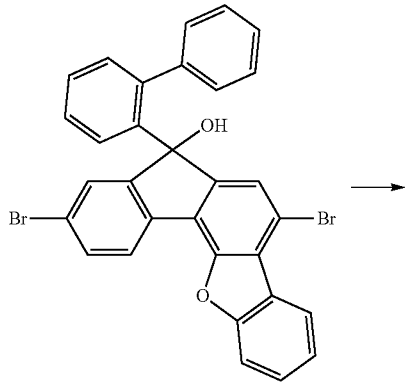

<Intermediate 10-e>

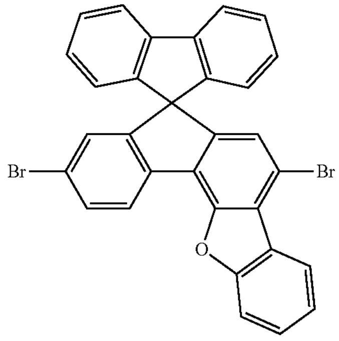

<Intermediate 10-f>

In a 250-ml round-bottom flask reactor, a mixture of <Intermediate 10-e> (12.0 g, 0.021 mol), acetic acid (120 ml), and sulfuric acid (2 ml) was stirred for 5 hrs under reflux. When a precipitate was formed, the completion of the reaction was monitored using thin layer chromatography. The reaction mixture was then cooled to room temperature and filtered. The filtrate was washed with H2O and methanol and dissolved in monochlorobenzene. Following silica gel chromatography, the fraction was concentrated and cooled to room temperature to give <Intermediate 10-f>. (10.7 g, 90%>

Synthesis Example 10-(7): Synthesis of [BD 2]

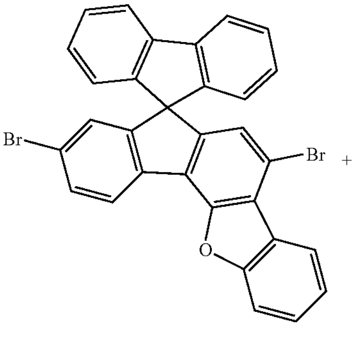

<Intermediate 10-f>

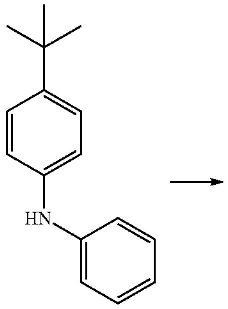

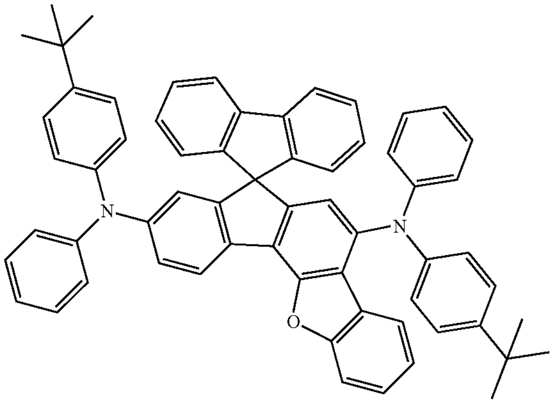

<BD 2>

In a 250-ml round-bottom flask reactor, a mixture of <Intermediate 10-f> (5.0 g, 0.009 mol), (4-tert-butylphenyl)-phenylamine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield <BD 2> as a solid (2.9 g, 38%).

MS (MALDI-TOF): m/z 852.41 [M+]

Example 1~6: Fabrication of Organic Light-Emitting Diode

An ITO glass substrate was patterned to have a luminescent area of 2 mm×2 mm and cleansed. The ITO glass was mounted in a vacuum chamber, which was then set to have a base pressure of 1×10-7 torr. On the ITO glass substrate, films of DNTPD (400 Å) and α-NPD (200 Å) were formed in that order. A light-emitting layer (200 Å) was formed of a mixture of one of the compounds listed in Table 1 as a host and BDI as a dopant (weight ratio 97:3). Then, the compounds shown in Table 1 were deposited to form an electron-density-controlling layer (50 Å thick), on which [Chemical Formula E-1] for an electron transport layer (250 Å), [Chemical Formula E-2] for an electron injection layer (5 Å), and Al (1000 Å) were deposited in that order to fabricate an organic light-emitting diode. The organic light-emitting diode thus obtained was measured at 10 mA/cm2 to determine the luminescence properties thereof.

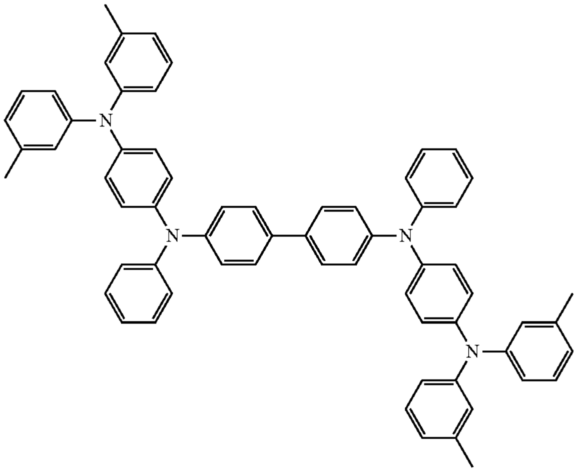

[DNTPD]

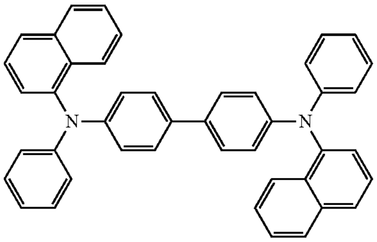

[α-NPD]

[BD1]

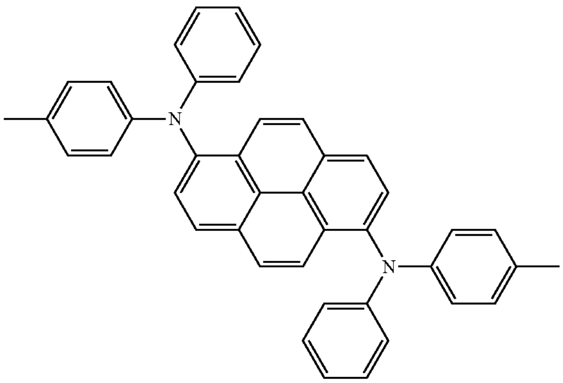

-continued

[Chemical Formula E-1]

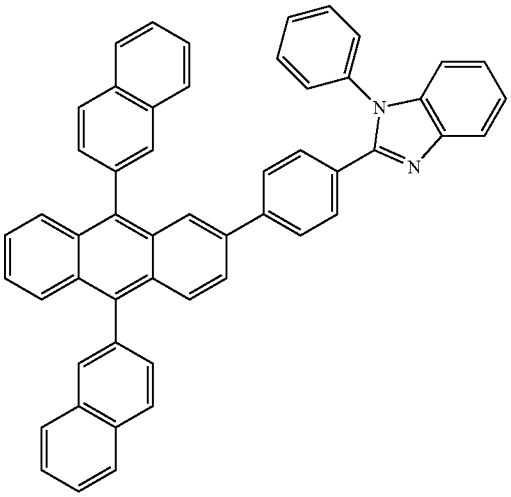

[Chemical Formula E-2]

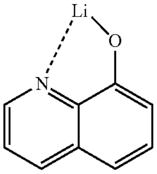

Examples 7 to 13: Fabrication of Organic Light-Emitting Diode

An organic light-emitting diode was fabricated in the same manner as in Examples 1 to 6, with the exception that [BD2] was used, instead of [BD1], as a dopant in the light-emitting layer. The organic light-emitting diode was measured at 10 mA/cm2 to determine the luminescence properties thereof. The structure of [BD2] is as follows:

[BD2]

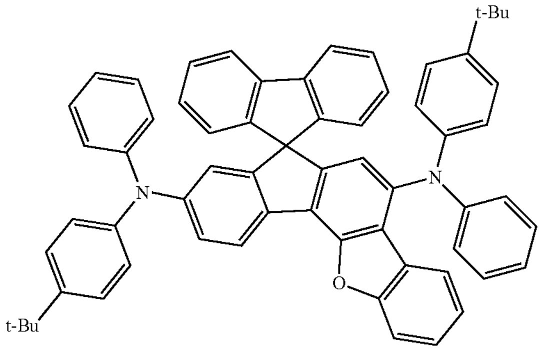

Comparative Example 1

An organic light-emitting diode was fabricated in the same manner as in Example 3, with the exception that [ET2] was used an electron-density-controlling layer. The organic light-emitting diode was measured at 10 mA/cm2 to determine the luminescence properties thereof.

[ET2]

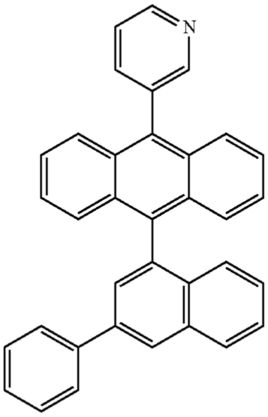

Comparative Examples 2 and 3: Fabrication of Organic Light-Emitting Diode

An organic light-emitting diode was fabricated in the same manner as in Examples 1 to 6, with the exception that [BH1] and [BH2] were used in combination as a host in a light-emitting layer. The organic light-emitting diode was measured at 10 mA/cm2 to determine the luminescence properties thereof. The structures of [BH1] and [BH2] are as follows:

[BH1]

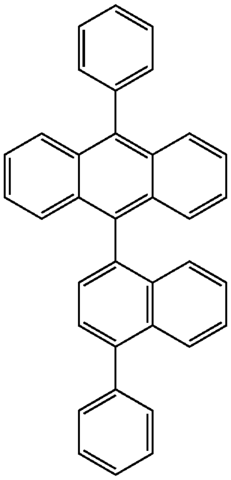

-continued

[BH2]

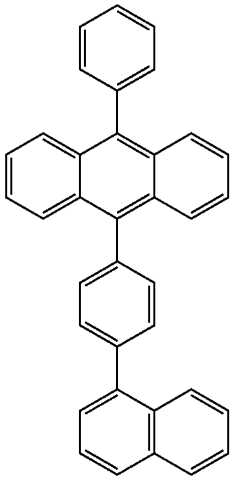

Comparative Examples 4 to 8

Organic light-emitting diodes were fabricated in the same manner as in Examples 1 to 6, with the exception that an electron-density-controlling layer was not formed.

TABLE 1

| | Host | Dopant | Electron-Density-Controlling Layer | V | CIEx | CIEy | EQE |
|---|---|---|---|---|---|---|---|
| Ex. 1 | Cpd. 76 | BD1 | Cpd. 203 | 3.47 | 0.138 | 0.111 | 12.21 |
| Ex. 2 | Cpd. 76 | BD1 | Cpd. 299 | 3.50 | 0.138 | 0.110 | 12.09 |
| Ex. 3 | Cpd. 103 | BD1 | Cpd. 203 | 3.43 | 0.138 | 0.107 | 12.31 |
| Ex. 4 | Cpd. 103 | BD1 | Cpd. 209 | 3.45 | 0.137 | 0.110 | 12.05 |
| Ex. 5 | Cpd. 103 | BD1 | Cpd. 213 | 3.42 | 0.138 | 0.105 | 12.12 |
| Ex. 6 | Cpd. 103 | BD1 | Cpd. 299 | 3.44 | 0.138 | 0.109 | 11.61 |
| Ex. 7 | Cpd. 76 | BD2 | Cpd. 299 | 3.54 | 0.138 | 0.109 | 11.91 |
| Ex. 8 | Cpd. 103 | BD2 | Cpd. 203 | 3.58 | 0.138 | 0.106 | 11.84 |
| Ex. 9 | Cpd. 103 | BD2 | Cpd. 209 | 3.62 | 0.138 | 0.104 | 11.99 |
| Ex. 10 | Cpd. 103 | BD2 | Cpd. 299 | 3.55 | 0.137 | 0.110 | 11.51 |
| Ex. 11 | Cpd. 140 | BD2 | Cpd. 299 | 3.46 | 0.137 | 0.110 | 11.95 |
| Ex. 12 | Cpd. 150 | BD2 | Cpd. 299 | 3.37 | 0.138 | 0.103 | 11.14 |
| Ex. 13 | Cpd. 151 | BD2 | Cpd. 299 | 3.31 | 0.138 | 0.111 | 11.88 |
| C. Ex. 1 | Cpd. 103 | BD1 | ET2 | 3.57 | 0.138 | 0.112 | 10.94 |
| C. Ex. 2 | BH1 | BD1 | Cpd. 299 | 3.69 | 0.137 | 0.110 | 10.96 |
| C. Ex. 3 | BH2 | BD1 | Cpd. 299 | 3.74 | 0.137 | 0.119 | 10.80 |
| C. Ex. 4 | Cpd. 103 | BD2 | — | 3.66 | 0.137 | 0.110 | 9.94 |
| C. Ex. 5 | Cpd. 103 | BD1 | — | 3.64 | 0.138 | 0.108 | 10.04 |
| C. Ex. 6 | Cpd. 140 | BD2 | — | 3.57 | 0.137 | 0.111 | 10.11 |
| C. Ex. 7 | Cpd. 150 | BD2 | — | 3.51 | 0.138 | 0.103 | 9.71 |
| C. Ex. 8 | Cpd. 151 | BD2 | — | 3.45 | 0.137 | 0.111 | 10.20 |

In FIG. 5, measurement results of Examples 3 to 5 (Devices 1 to 3) and Comparative Example 4 (Ref.) are depicted to show changes in current efficiency with voltage depending on the presence or absence of an electron-density-controlling layer in an organic light-emitting diode. In FIG. 6, measurement results of Examples 3 to 5 (Devices 1 to 3) and Comparative Example 4 (Ref.) are depicted to show the electron mobility plotted against electric field for the organic light-emitting diodes in which an electron-density-controlling layer is either present or absent.

Figure 7:
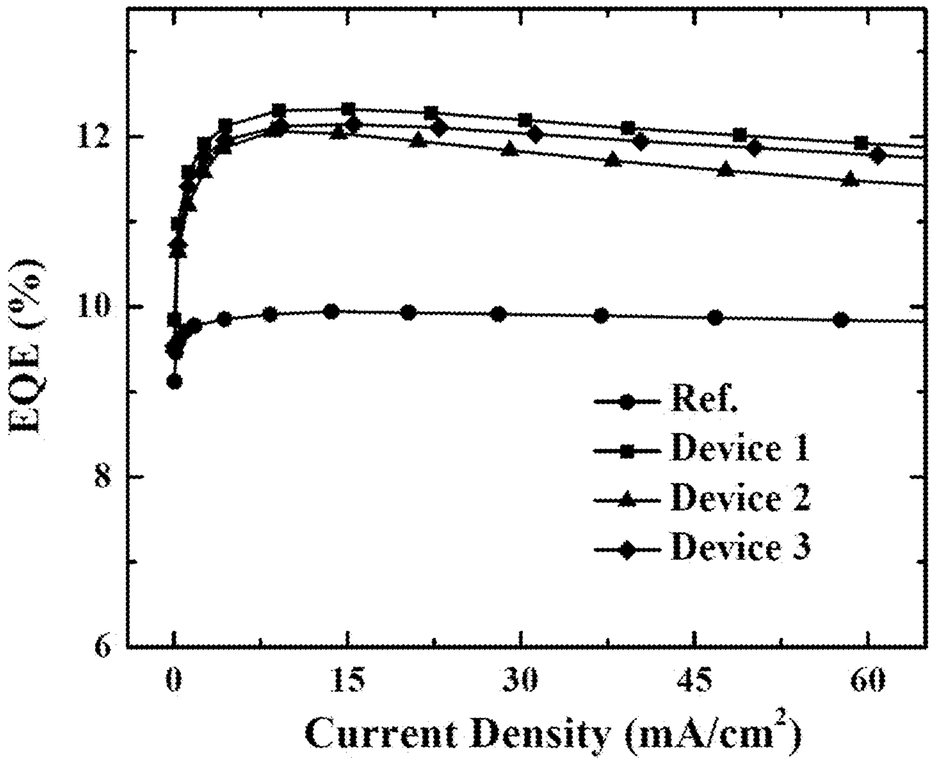
FIG. 7 shows changes in external quantum efficiency with current density in the organic light-emitting diodes in which an electron-density-controlling layer is present or absent.

Also, measurement results of Examples 3 to 5 (Devices 1 to 3) and Comparative Example 4 (Ref.) are depicted in FIG. 7 to show changes in external quantum efficiency with current density in the organic light-emitting diodes in which an electron-density-controlling layer is either present or absent.

As shown in Table 1 and FIG. 7, the organic light-emitting diodes of the present disclosure are superior in terms of low-voltage operation and external quantum efficiency to those of Comparative Examples 4 to 5, lacking the electron-density-controlling layer. Further, the organic light-emitting diodes of the present disclosure exhibited higher external quantum efficiency than those of Comparative Examples 2 and 3, which are provided with an electron-density-controlling layer but employ a host different from that used in the light-emitting layer of the present disclosure. Hence, organic light-emitting diodes of high efficiency can be fabricated according to the present disclosure.

Employing a specifically structured electron-density-controlling layer interposed between a light-emitting layer and an electron transport layer in combination with an anthracene derivative used for the light-emitting layer, the organic light-emitting diode of the present disclosure can exhibit higher luminance efficiency and more effective low-voltage operation than conventional diodes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An organic light-emitting diode, comprising:

a first electrode;

a second electrode opposite the first electrode; and a light-emitting layer, an electron-density-controlling layer, an electron transport layer and an electron injection layer in that order between the first electrode and the second electrode, wherein the light-emitting layer includes a host and a dopant, the electron-density-controlling layer is materially different from the electron transport layer; the electron transport layer is materially different from the electron injection layer; and the electron injection layer is materially different from the second electrode, an affinity of the host of the light-emitting layer (Ah), an affinity of the electron-density controlling layer (Aed), and an affinity of the electron transport layer (Ae) satisfy a relationship of Ah>Aed>Ae, the material of the electron-density-controlling layer is greater in electron mobility than that of the electron transport layer, the electron-density-controlling layer includes at least one selected from among compounds represented by the following Chemical Formulas A and C, and at least one anthracene compound represented by the following Chemical Formula H is used as the host:

[Chemical Formula A]

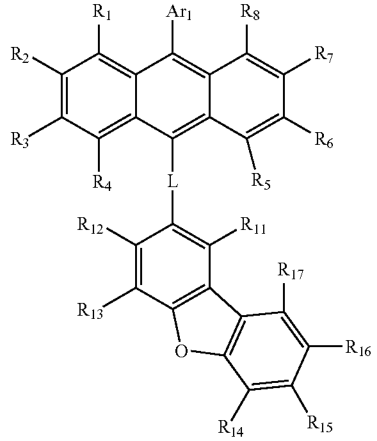

[Chemical Formula C]

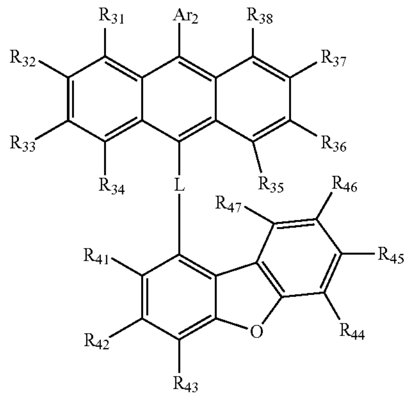

wherein, in Chemical Formula A and Chemical Formula C,

R1 to R8 and R31 to R38 may be the same or different, and are each independently any one selected from among a hydrogen atom and a deuterium atom, R11 to R17 and R41 to R47 may be the same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, and a substituted or unsubstituted heteroaryl of 2 to 50 carbon atoms containing O, N or S as a hetero atom, Ar1 and Ar2 may be the same or different, and are each independently a deuterium substituted phenyl, and a linker L is an unsubstituted naphthylene of 10 carbon atoms,

[Chemical Formula H]

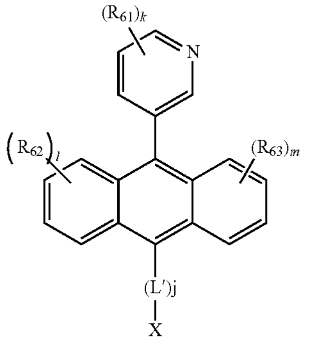

X = 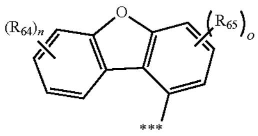 or 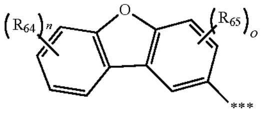

wherein, the substituents R61 to R65 may be the same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted heteroaryl of 2 to 50 carbon atoms containing O, N or S as a hetero atom, with the proviso that a hydrogen atom is positioned on each of the aromatic ring carbon atoms to which none of the substituents R61 to R65 are bonded, the linker L' is a single bond, j is 1, k is an integer of 1 to 5, l to n may be the same or different, and are each independently an integer of 1 to 4, o is an integer of 1 to 3, with the proviso that when each of k to o is 2 or greater, corresponding R61's to R65's may be the same or different, '***' for moiety X denotes a bonding site for bonding L', with the proviso that the anthracene compound of Chemical Formula H used in the light-emitting layer is different from the compounds of [Chemical Formula A] and [Chemical Formula C] used in the electron-density-controlling layer, wherein the term 'substituted' in the expression 'substituted or unsubstituted' means having at least one substituent selected from the group consisting of a deuterium atom, an alkyl of 1 to 24 carbon atoms, an aryl of 6 to 24 carbon atoms, and a heteroaryl of 2 to 24 carbon atoms.

2. The organic light-emitting diode of claim 1, wherein the first electrode is an anode and the second electrode is a cathode, with a hole transport layer interposed between the anode and the light-emitting layer.

3. The organic light-emitting diode of claim 1, wherein the compound represented by Chemical Formula H is selected from among the following Compounds 100 to 108, 130 to 132, 139 to 156:

<Cpd. 100>

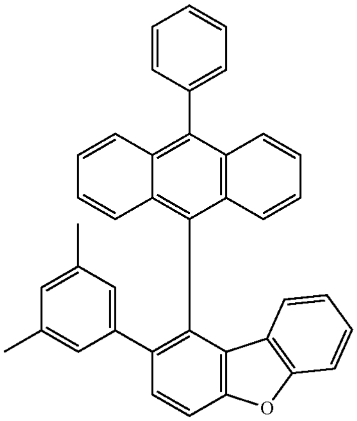

<Cpd. 101>

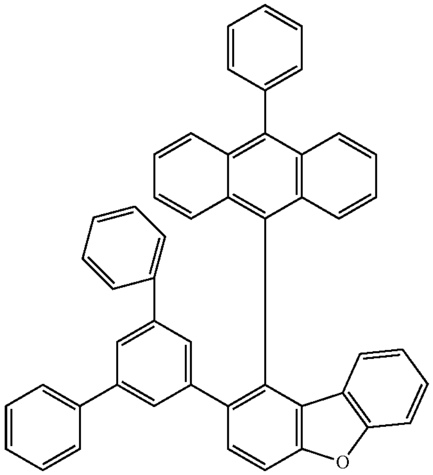

<Cpd. 102>

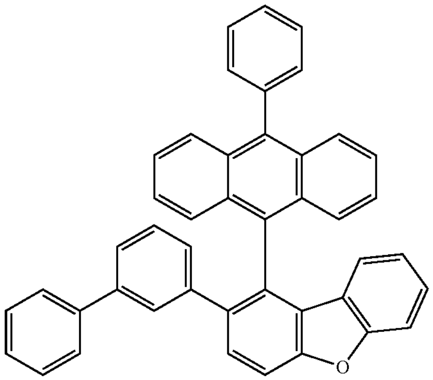

-continued
(Cpd. 103>
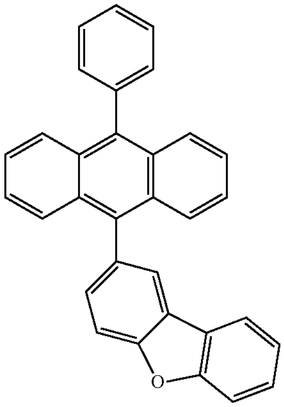
<Cpd.104>
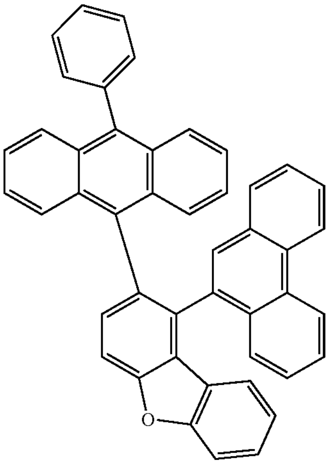
<Cpd.105>
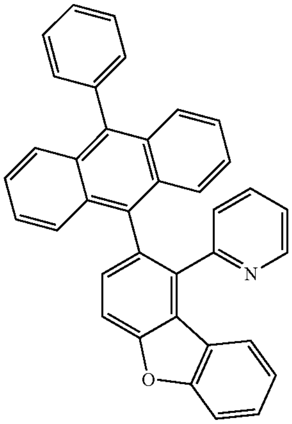
-continued
<Cpd. 106>
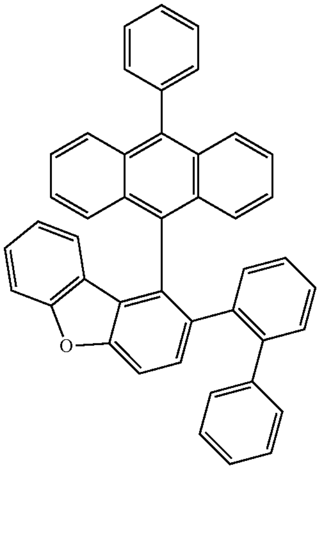
<Cpd. 107>
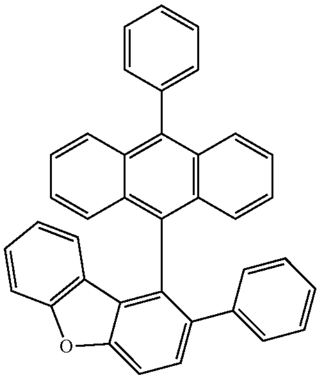
<Cpd. 108>
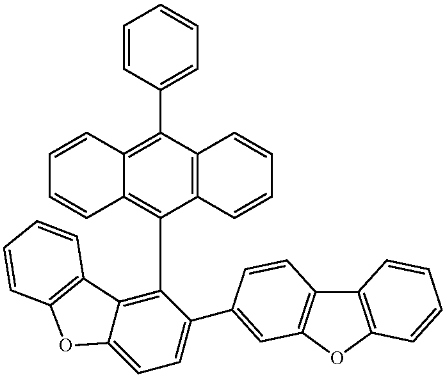

-continued
<Cpd. 130>
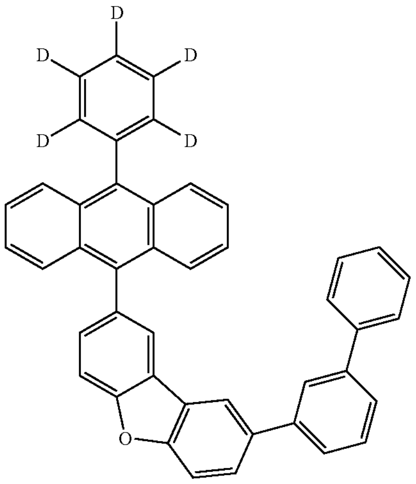
<Cpd. 131>
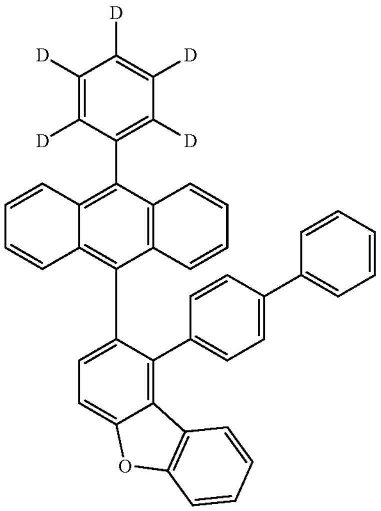
<Cpd. 132>
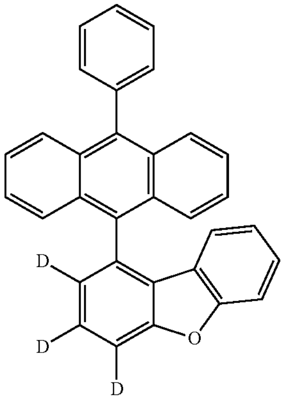
-continued
<Cpd. 139>
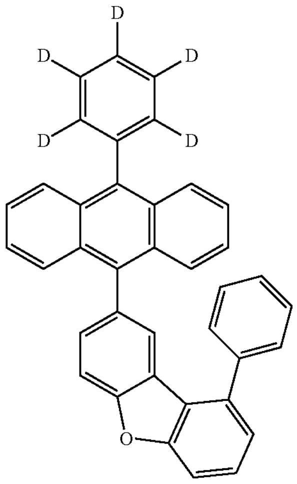
<Cpd. 140>
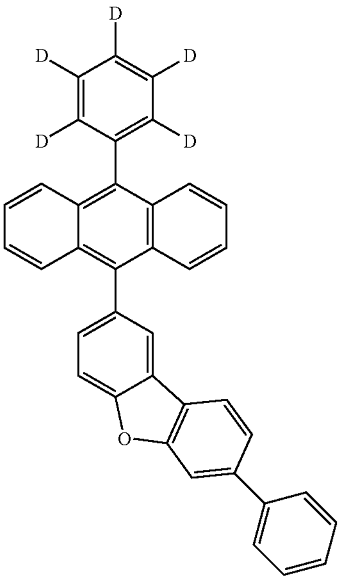
<Cpd. 141>
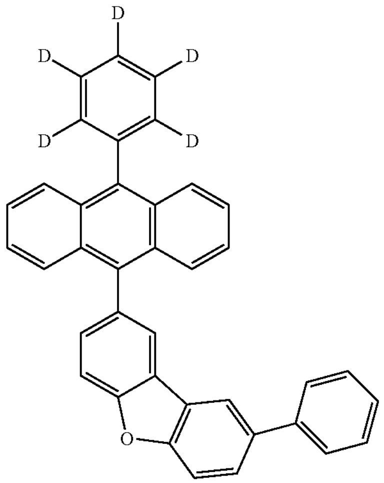

-continued
<Cpd. 142>
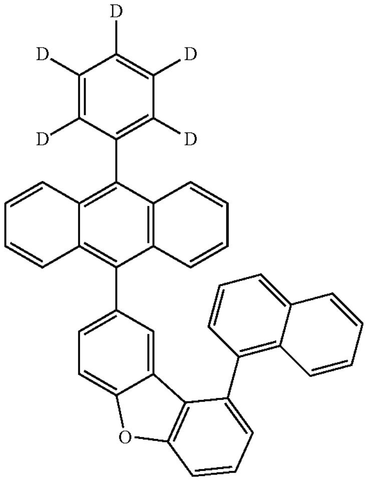
<Cpd. 143>
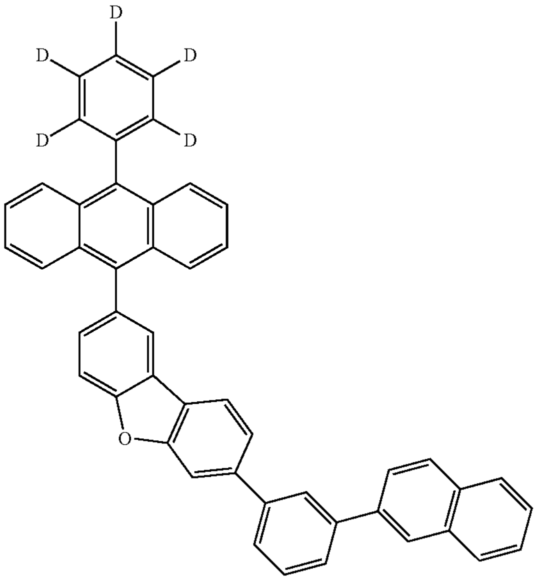
<Cpd. 144>
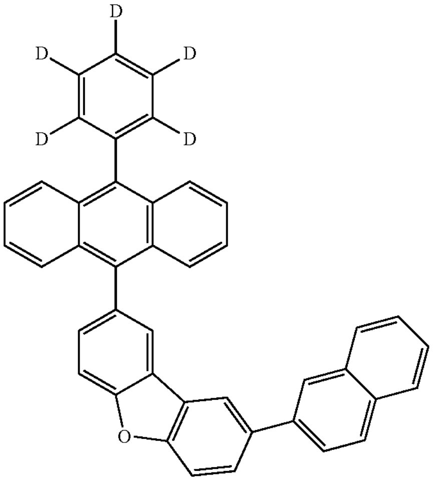
-continued
<Cpd. 145>
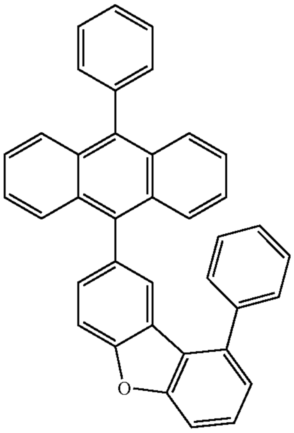
<Cpd. 146>
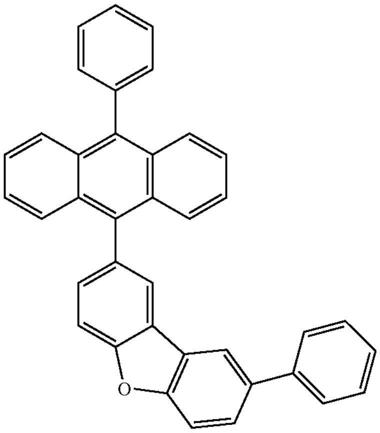
<Cpd. 147>
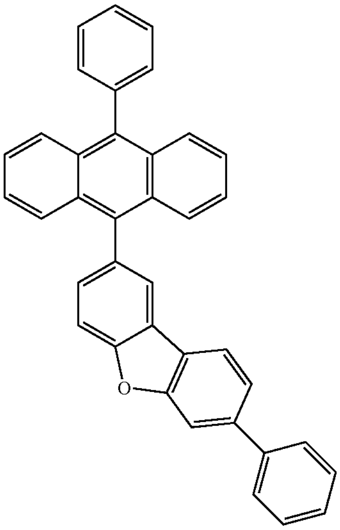

-continued
<Cpd. 148>
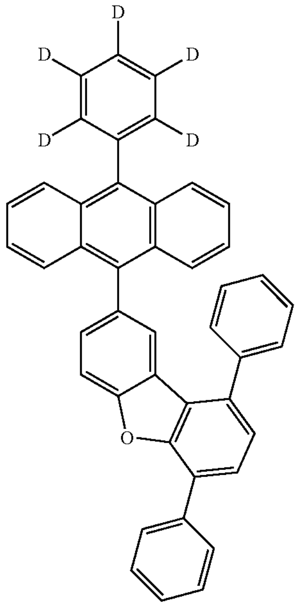
<Cpd. 149>
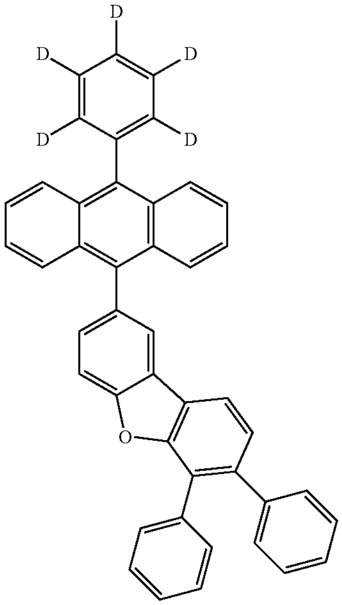
-continued
<Cpd. 150>
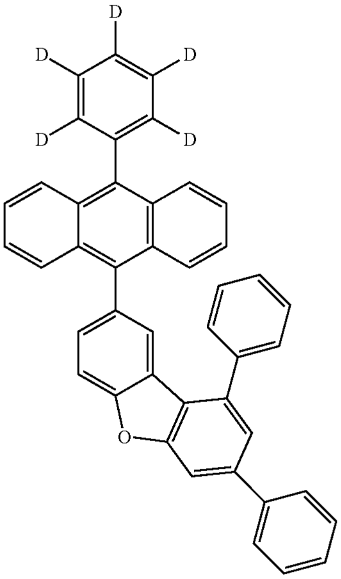
<Cpd. 151>
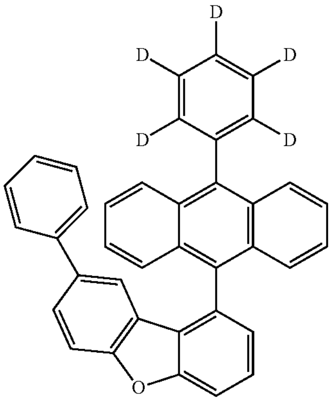
<Cpd. 152>
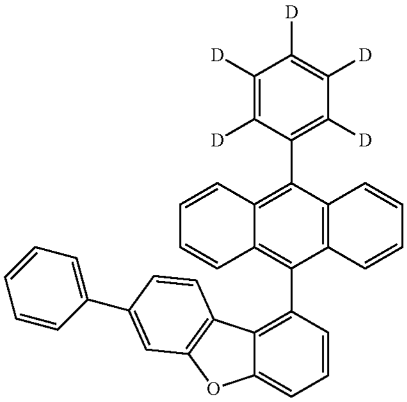

-continued
<Cpd. 153>
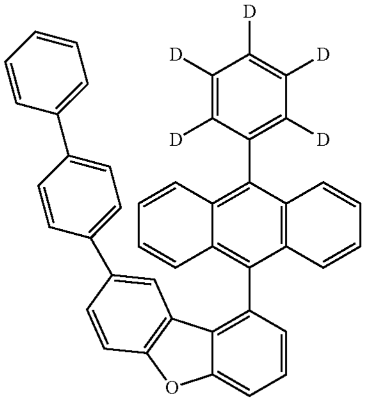
<Cpd. 154>
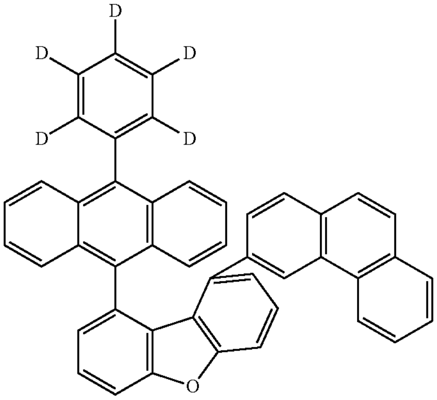
<Cpd. 155>
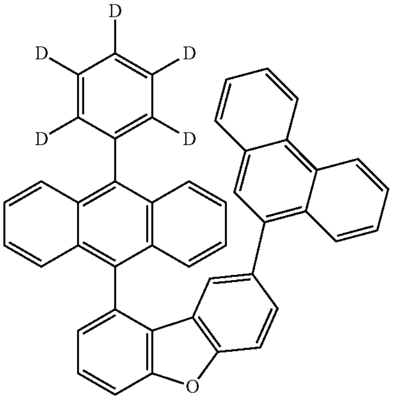
<Cpd. 156>
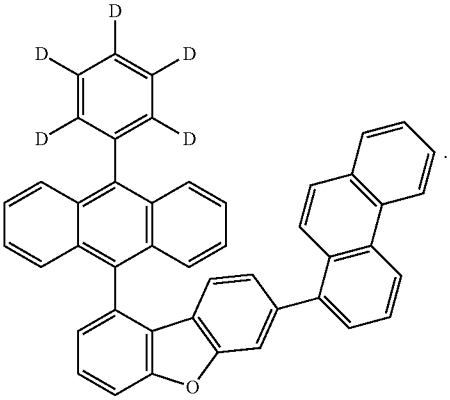
4. The organic light-emitting diode of claim 1, wherein the electron-density-controlling layer includes at least one selected from among Cpd. 283, Cpd. 284, and Cpd. 299:
<Cpd. 283>
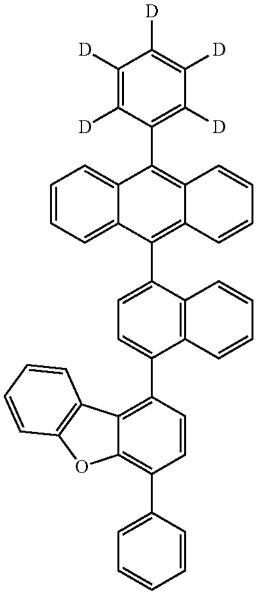
<Cpd. 284>
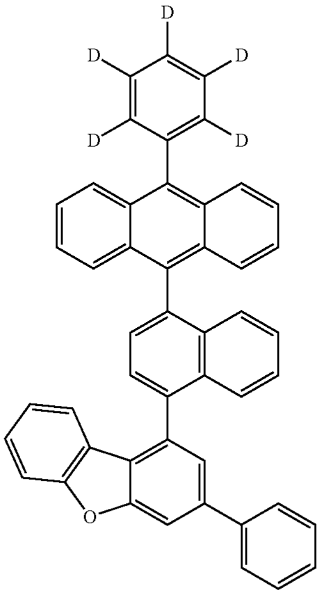

-continued

<Cpd. 299>

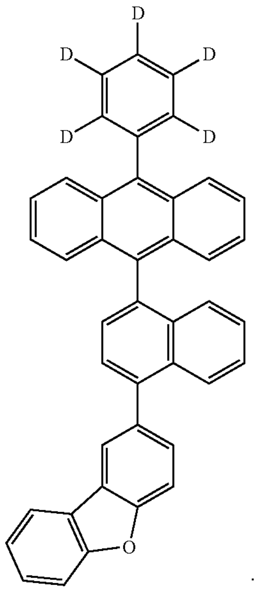

5. The organic light-emitting diode of claim 1, wherein the compounds represented by [Chemical Formula A] or [Chemical Formula C], or the compound represented by [Chemical Formula H], contain a deuterium atom.

6. The organic light-emitting diode of claim 2, wherein a hole injection layer is introduced between the anode and the hole transport layer.

7. The organic light-emitting diode of claim 6, wherein at least one of the layers is formed using a deposition process or a solution process.

8. The organic light-emitting diode of claim 1, wherein the organic light-emitting diode is used for a device selected from among a flat display device, a flexible display device, a monochrome or white flat illumination device, and a monochrome or white flexible illumination device.

9. An organic light-emitting diode, comprising:

a first electrode;

a second electrode opposite the first electrode; and a light-emitting layer, an electron-density-controlling layer, an electron transport layer and an electron injection layer in that order between the first electrode and the second electrode, wherein the light-emitting layer includes a host and a dopant, the electron-density-controlling layer is materially different from the electron transport layer; the electron transport layer is materially different from the electron injection layer; and the electron injection layer is materially different from the second electrode, an affinity of the host of the light-emitting layer (Ah), an affinity of the electron-density controlling layer (Aed), and an affinity of the electron transport layer (Ae) satisfy a relationship of Ah>Aed>Ae, the material of the electron-density-controlling layer is greater in electron mobility than that of the electron transport layer, the electron-density-controlling layer includes at least a compound represented by the following Cpd. 298, and at least one anthracene compound represented by the following Chemical Formula H is used as the host:

<Cpd. 298>

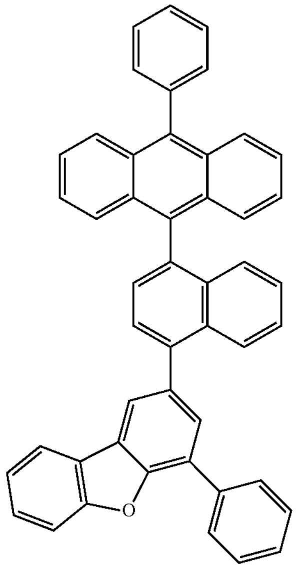

wherein, the substituents R61 to R65 may be the same or different, and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted heteroaryl of 2 to 50 carbon atoms containing O, N or S as a hetero atom, with the proviso that a hydrogen atom is positioned on each of the aromatic ring carbon atoms to which none of the substituents R61 to R65 are bonded, the linker L' is a single bond, j is 1, k is an integer of 1 to 5, l to n may be the same or different, and are each independently an integer of 1 to 4, o is an integer of 1 to 3, with the proviso that when each of k to o is 2 or greater, corresponding R61's to R65's may be the same or different, '***' for moiety X denotes a bonding site for bonding L', with the proviso that the anthracene compound of Chemical Formula H used in the light-emitting layer is different from Cpd. 298 used in the electron-density-controlling layer, wherein the term 'substituted' in the expression 'substituted or unsubstituted' means having at least one substituent selected from the group consisting of a deuterium atom, an alkyl of 1 to 24 carbon atoms, an aryl of 6 to 24 carbon atoms, and a heteroaryl of 2 to 24 carbon atoms.

* * * * *